United States Patent
Lowe, III et al.

(10) Patent No.: US 6,235,747 B1
(45) Date of Patent: *May 22, 2001

(54) 6-PHENYL-PYRIDIN-2-YLAMINE DERIVATIVES

(75) Inventors: John A. Lowe, III, Stonington, CT (US); Peter J. Whittle, Sandwich (GB)

(73) Assignee: Pfizer Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/816,235

(22) Filed: Mar. 13, 1997

Related U.S. Application Data

(60) Provisional application No. 60/014,343, filed on Mar. 29, 1996.

(51) Int. Cl.$^7$ ............... A61K 31/444; A61K 31/4427; A61K 31/46; C07D 401/12; C07D 498/08
(52) U.S. Cl. ............... 514/278; 514/230.5; 514/183; 514/216; 514/249; 514/278; 514/299; 514/339; 514/304; 540/349; 540/477; 540/582; 544/105; 546/16; 546/20; 546/112; 546/125; 546/276.7
(58) Field of Search ............... 546/276.7, 16, 546/20, 125, 112; 514/339, 278, 230.5, 304, 299, 183, 216, 249; 544/105, 349; 540/477, 582

(56) References Cited

U.S. PATENT DOCUMENTS 5,629,322 * 5/1997 Guthikonda ............... 514/313

OTHER PUBLICATIONS

Parkash L et al. Curr. Sci. 58(17), 967–70, 1989.*
Verma SS et al. J. Indian Chem. Soc. 65(11), 789–9, 1988.*

* cited by examiner

*Primary Examiner*—Evelyn Mei Huang
(74) *Attorney, Agent, or Firm*—Peter C. Richardson; Paul H. Ginsburg; Karen DeBenedictis

(57) ABSTRACT

The present invention relates to certain 6-phenyl-pyridin-2-ylamine derivatives that exhibit activity as nitric oxide synthase (NOS) inhibitors, to pharmaceutical compositions containing them and to their use in the treatment and prevention of central nervous system disorders.

9 Claims, No Drawings

6-PHENYL-PYRIDIN-2-YLAMINE DERIVATIVES

This application claims the benefit of provisional application No. 60/014,343, filed on Mar. 29, 1996.

The present invention relates to certain 6-phenylpyridyl-2-amine derivatives that exhibit activity as nitric oxide synthase (NOS) inhibitors, to pharmaceutical compositions containing them and to their use in the treatment and prevention of central nervous system disorders, inflammatory disorders, septic shock and other disorders.

There are three known isoforms of NOS—an inducible form (I-NOS) and two constitutive forms referred to as, respectively, neuronal NOS (N-NOS) and endothelial NOS (E-NOS). Each of these enzymes carries out the conversion of arginine to citrulline while producing a molecule of nitric oxide (NO) in response to various stimuli. It is believed that excess nitric oxide (NO) production by NOS plays a role in the pathology of a number of disorders and conditions in mammals. For example, NO produced by I-NOS is thought to play a role in diseases that involve systemic hypotension such as toxic shock and therapy with certain cytokines. It has been shown that cancer patients treated with cytokines such as interleukin 1 (IL-1), interleukin 2 (IL-2) or tumor necrosis factor (TNF) suffer cytokine-induced shock and hypotension due to NO produced from macrophages, i.e., inducible NOS (I-NOS), see *Chemical & Engineering News*, December 20, p. 33, (1993). I-NOS inhibitors can reverse this. It is also believed that I-NOS plays a role in the pathology of diseases of the central nervous system such as ischemia. For example, inhibition of I-NOS has been shown to ameliorate cerebral ischemic damage in rats, see *Am. J. Physiol.*, 268, p. R286 (1995)). Suppression of adjuvant induced arthritis by selective inhibition of I-NOS is reported in *Eur. J. Pharmacol.*, 273, p. 15–24 (1995).

NO produced by N-NOS is thought to play a role in diseases such as cerebral ischemia, pain, and opiate tolerance. For example, inhibition of N-NOS decreases infarct volume after proximal middle cerebral artery occlusion in the rat, see *J. Cerebr. Blood Flow Metab.*, 14, p. 924–929 (1994). N-NOS inhibition has also been shown to be effective in antinociception, as evidenced by activity in the late phase of the formalin-induced hindpaw licking and acetic acid-induced abdominal constriction assays, see *Br. J. Pharmacol.*, 110, p. 219–224 (1993). Finally, opioid withdrawal in rodents has beer reported to be reduced by N-NOS inhibition, see *Neuropsychopharmacol.*, 13, p. 269–293 (1995).

SUMMARY OF THE INVENTION

This invention relates to compounds of the formula

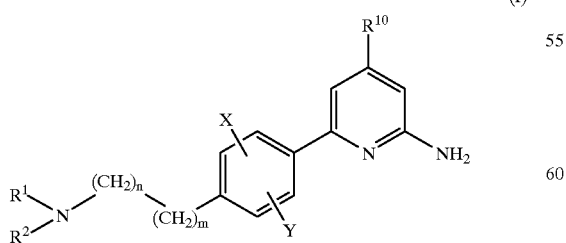

and the pharmaceutically acceptable salts thereof, wherein $R^1$ and $R^2$ are selected, independently, from $(C_1-C_6)$ alkyl, tetrahydronaphthalene and aralkyl, wherein the aryl moiety of said aralkyl is phenyl or naphthyl and the alkyl moiety i:s straight or branched and contains from 1 to 6 carbon atoms, and wherein said $(C_1-C_6)$ alkyl and said tetrahydronaphthalene and the aryl moiety of said aralkyl may optionally be substituted with from one to three substituents, preferably from zero to two substituents, that are selected, independently, from halo (e.g., chloro, fluoro, bromo, iodo), nitro, hydroxy, cyano, amino, $(C_1-C_4)$ alkoxy, and $(C_1-C_4)$ alkylamino;

or $R^1$ and $R^2$ form, together with the nitrogen to which they are attached, a piperazine, piperidine or pyrrolidine ring or an azabicyclic ring containing from 6 to 14 ring members, from 1 to 3 of which are nitrogen and the rest of which are carbon, wherein examples of said azabicyclic rings are the following

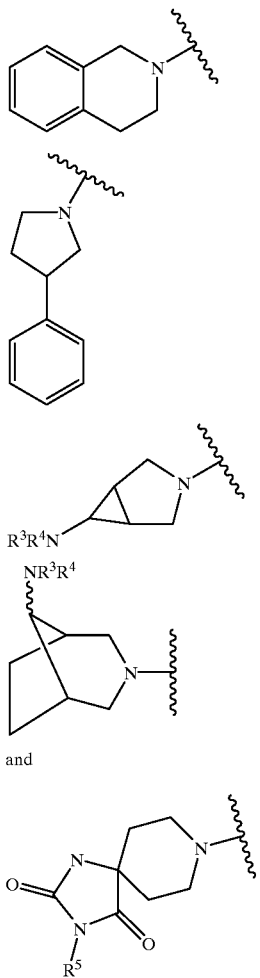

and wherein $R^3$ and $R^4$ are selected from hydrogen, $(C_1-C_6)$alkyl, phenyl, naphthyl, $(C_1-C_6)$alkyl-C(=O)—, HC(=O)—, $(C_1-C_6)$alkoxy-(C=O)—, phenyl-C(=O)—, naphthyl-C(=O)—, and —$(R^7)_2$NC(=O)— wherein each $R^7$ is selected, independently, from hydrogen and $(C_1-C_6)$alkyl;

$R^5$ is selected from hydrogen, $(C_1-C_6)$alkyl, phenyl, naphthyl, phenyl-$(C_1-C_6)$alkyl- and naphthyl $(C_1-C_6)$alkyl-;

and wherein said piperazine, piperidine and pyrrolidine rings may optionally be substituted with one or more substituents, preferably with from zero to two substituents that are selected, independently, from (C₁–C₆)alkyl, amino, (C₁–C₆) alkylamino, [di-(C₁–C₆)alkyl]amino, phenyl substituted 5 to 6 membered heterocyclic rings containing from 1 to 4 rings nitrogen atoms, benzoyl, benzoylmethyl, benzylcarbonyl, phenylaminocarbonyl, phenylethyl and phenoxycarbonyl, and wherein the phenyl moieties of any of the foregoing substituents may optionally be substituted with one or more substituents, preferably with from zero to two substituents, that are selected, independently, from halo, $(C_1–C_3)$alkyl, $(C_1–C_3)$alkoxy, nitro, amino, cyano, $CF_3$ and $OCF_3$;

n is 0,1 or 2; and each carbon of said $(CH_2)_n$ can optionally be substituted with a substituent $R^8$;

m is 0,1, or 2; and each carbon of said $(CH_2)_m$ can optionally be substituted with a substituent $R^9$;

each $R^8$ and each $R^9$ is selected, independently, from $(C_1–C_4)$alkyl, aryl-$(C_1–C_4)$alkyl wherein said aryl is selected from phenyl and naphthyl; allyl and phenallyl;

X and Y are selected, independently, from methyl, methoxy, hydroxy and hydrogen; and $R^{10}$ is $H(C_1–C_6)$ alkyl;

with the proviso that $R^8$ is absent when n is zero and $R^9$ is absent when m is zero.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1-methylene-bis-(2-hydroxy-3-naphthoate)] salts.

The term "alkyl", as used herein, unless otherwise indicated, includes saturated monovalent hydrocarbon radicals having straight, branched or cyclic moieties or combinations thereof.

The term "one or more substituents", as used herein, refers to a number of substituents that equals from one to the maximum number of substituents possible based on the number of available bonding sites.

The term "halo", as used herein, unless otherwise indicated, includes chloro, fluoro, bromo and iodo.

Examples of preferred compounds of this invention are compounds of the formula I, and their pharmaceutically acceptable salts, wherein $NR^1R^2$ is:

4-phenoxycarbonylpiperazin-1-yl;
4-(4-fluorophenylacetyl)piperazin-1-yl;
4-phenylethylpiperazin-1-yl;
4-phenoxymethylcarbonylpiperazin-1-yl;
4-phenylaminocarbonylpiperazin-1-yl;
4-benzoylmethylpiperazin-1-yl; or
4-benzylcarbonylpiperazin-1-yl.

Other preferred compounds of this invention are compounds of the formula I, and their pharmaceutically acceptable salts, wherein $NR^1R^2$ is a group of the formula

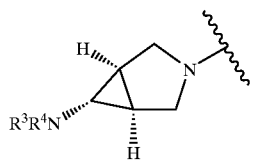

wherein $NR^3R^4$ is $NH_2$.

Other preferred compounds of this invention are compounds of the formula I, and their pharmaceutically acceptable salts, wherein $NR^1R^2$ is a group of the formula

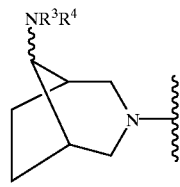

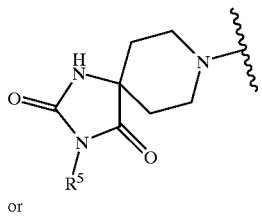

or

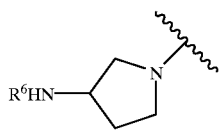

wherein $R^5$ is aralkyl, e.g., benzyl, and $R^6$ is (4-fluoro) phenylacetyl.

Specific preferred compounds of the present invention include the following:

1-4-{2-[4-(6-Amino-pyridin-2-yl)-phenyl]-ethyl}-piperazin-1-yl)-ethanone;

1-(4-{2-[4-(6-Amino-pyridin-2-yl)-phenyl]-ethyl}-piperazin-1-yl)-2-methoxy-ethanone;

1-(4-{2-[4-(6-Amino-pyridin-2-yl)-phenyl]-ethyl}-piperazin-1-yl)-2-phenoxy-ethanone;

(4-{2-[4-(6-Amino-pyridin-2-yl)-phenyl]-ethyl}-piperazin-1-yl)-cyclopentyl-methanone;

1-(4-{2-[4-(6-Amino-pyridin-2-yl)-phenyl]-ethyl}-piperazin-1-yl)-2-phenyl-ethanone;

3-{2-[4-(6-Amino-pyridin-2-yl)-phenyl]-ethyl}-3-aza-bicyclo[3.1.0]hex-6-ylamine;

2-(4-{2-[4-(6-Amino-pyridin-2-yl)-phenyl]-ethyl}-piperazin-1-yl)-1-phenyl-ethanone;

1-(4-{2-[4-(6-Amino-pyridin-2-yl)-phenyl]-ethyl}-piperazin-1-yl)-2-(4-fluoro-phenyl)-ethanone;

6-{4-[2-(4-Phenethyl-pipereizin-1-yl)-ethyl]-phenyl}-pyridin-2-ylamine;

2-(4-{2-[4-(6-Amino-pyridin-2-yl)-phenyl]-ethyl}-piperazin-1-yl)-1-phenyl-ethanol;

{2-[4-(6-Amino-pyridin-2-yl)-phenyl]-ethyl}-(3-oxa-9-aza-bicyclo[3.3.1]non-7-yl)-amine;

6-(4-{2-[4-(2-Amino-2-phenyl-ethyl)-piperazin-1-yl]-ethyl}-phenyl)-pyridin-2-ylamine;

6-{4-[2-(4-Amino-2,6-dimethyl-piperidin-1-yl)-ethyl]-phenyl}-pyridin-2-ylamine;
6-{4-[2-(4-Methyl-piperazin-1-yl)-ethyl]-phenyl}-pyridin-2-ylamine;
(3-{2-[4-(6-Amino-pyridin-2-yl)-phenyl]-ethyl}-3-aza-bicyclo[3.1.0]hex-6-yl)-dimethyl-amine;
6-[4-(2-Amino-ethyl)-phenyl]-pyridin-2-ylamine;
6-{4-[2-(8-Aza-spiro[4.5]dec-8-yl)-ethyl]-phenyl}-pyridin-2-ylamine;
6-{4-[2-(4-Isobutyl-piperazin-1-yl)-ethyl]-phenyl}-pyridin-2-ylamine;
2-(4-{2-[4-(6-Amino-pyridin-2-yl)-phenyl]-ethyl}-piperazin-1-yl)-N-isopropyl-acetamide;
4-{2-[4-(6-Amino-pyridin-2-yl)-phenyl]-ethyl}-piperazine-1-carboxylic acid p-tolyl-amide;
6-(4-{2-[4-(3-Phenyl-propyl)-piperazin-1-yl]-ethyl}-phenyl)-pyridin-2-ylamine;
1-(4-{2-[4-(6-Amino-pyridin-2-yl)-phenyl]-ethyl}-piperazin-1-yl)-2-(4-chloro-phenyl)-ethanone;
8-{2-[4-(6-Amino-pyridin-2-yl)-phenyl]-ethyl}-3-benzyl-1,3,8-triaza-spiro[4.5]decane-2,4-dione;
N-(1-{2-[4-(6-Amino-pyridin-2-yl)-phenyl]-ethyl}-pyrrolidin-3-yl)-2-(4-fluoro-phenyl)-acetamide;
8-{2-[4-(6-Amino-pyridin-2-yl)-phenyl]-ethyl}-8-aza-bicyclo[3.2.1]oct-3-ylamine;
3-{2-[4-(6-Amino-pyridin-2-yl)-phenyl]-ethyl}-3-aza-bicyclo[3.2.1]oct-8-ylamine;
2-Amino-1-(4-{2-[4-(6-amino-pyridin-2-yl)-phenyl]-ethyl}-piperazin-1-yl)-3-phenyl-propan-1-one;
6-{4-[2-(4-Amino-piperidin-1-yl)-ethyl]-phenyl}-pyridin-2-ylamine;
6-{4-[2-(4-Benzhydryl-piperiazin-1-yl)-ethyl]-phenyl}-pyridin-2-ylamine;
6-{4-[2-(4-Benzhydryl-piperidin-1-yl)-ethyl]-phenyl}-pyridin-2-ylamine;
6-{4-[(Cyclohexyl-methyl-amino)-methyl]-phenyl}-pyridin-2-ylamine;
6-{4-[(Cyclohexyl-methyl-amino)-methyl]-2-methoxy-phenyl}-pyridin-2-ylamine;
6-[4-(Phenethylamino-methyl)-phenyl]-pyridin-2-ylamine;
6-[2-Methoxy-4-(phenethylamino-methyl)-phenyl]-pyridin-2-ylamine;
6-[4-(4-Amino-piperidin-1-ylmethyl)-phenyl]-pyridin-2-ylamine;
6-{4-[(Cyclohexyl-methyl-amino)-methyl]-2-fluoro-phenyl}-pyridin-2-ylamine;
Other compounds of the formula I include:
1-(4-{2-[4-(6-Amino-pyridin-2-yl)-2-methoxy-phenyl]-ethyl}-piperazin-1-yl)-2-phenyl-ethanone;
6-{4-[2-(4-Isobutyl-piperazin-1-yl)-ethyl]-2-methoxy-phenyl}-pyridin-2-ylamine;
3-{2-[4-(6-Amino-pyridin-2-yl)-2-methoxy-phenyl]-ethyl}-3-aza-bicyclo[3.1.0]hex-6-ylamine;
{2-[4-(6-Amino-pyridin-2-yl)-2-methoxy-phenyl]-ethyl}-(3-oxa-9-aza-bicyclo[3.3.1]non-7-yl)-amine;
6-(4-{2-[4-(2-Amino-2-phenyl-ethyl)-piperazin-1-yl]-ethyl}-2-methoxy-phenyl)-pyridin-2-ylamine;
6-{4-[2-(4-Amino-2-methoxy-piperidin-1-yl)-ethyl]-2-methoxy-phenyl}-pyridin-2-ylamine;
2-(4-{2-[4-(6-Amino-pyridin-2-yl)-2-methoxy-phenyl]-ethyl}-piperazin-1-yl)-N-isopropyl-acetamide;
6-[4-(4-Amino-piperidin-1-ylmethyl)-2-methoxy-phenyl]-pyridin-2-ylamine;
1-(4-{2-[4-(6-Amino-pyridin-2-yl)-2-methyl-phenyl]-ethyl}-piperazin-1-yl)-2-phenyl-ethanone;
6-{4-[2-(4-Isobutyl-piperazin-1-yl)-ethyl]-2-methyl-phenyl}-pyridin-2-ylamine;
3-{2-[4-(6-Amino-pyridin-2-yl)-2-methyl-phenyl]-ethyl}-3-aza-bicyclo[3.1.0]hex-6-ylamine;
2-(4-{2-[4-(6-Amino-pyridin-2-yl)-2-methyl-phenyl]-ethyl}-piperazin-1-yl)-phenyl-ethanone;
1-(4-{2-[4-(6-Amino-pyridin-2-yl)-2-methyl-phenyl]-ethyl}-piperazin-1-yl)-2-(4-fluoro-phenyl)-ethanone;
6-{4-[2-(4-Phenethyl-pipereizin-1-yl)-ethyl]-2-methyl-phenyl}-pyridin-2-ylamine;
2-(4-{2-[4-(6-Amino-pyridin-2-yl)-2-methyl-phenyl]-ethyl}-piperazin-1-yl)-1-phenyl-ethanol;
{2-[4-(6-Amino-pyridin-2-yl)-2-methyl-phenyl]-ethyl}-(3-oxa-9-aza-bicyclo[3.3.1]non-7-yl)-amine;
6-(4-{2-[4-(2-Amino-2-phenyl-ethyl)-piperazin-1-yl]-ethyl}-2-methyl-phenyl)-pyridin-2-ylamine;
6-{4-[2-(4-Amino-2,6-dimethyl-piperidin-1-yl)-ethyl]-2-methyl-phenyl}-pyridin-2-ylamine;
2-(4-{2-[4-(6-Amino-pyridin-2-yl)-2-methyl-phenyl]-ethyl}-piperazin-1-yl)-N-isopropyl-acetamide;
6-[4-(4-Amino-piperidin-1-ylmethyl)-2-methyl-phenyl]-pyridin-2-ylamine;
N-(1-{2-[4-(6-Amino-pyridin-2-yl)-phenyl]-ethyl}-pyrrolidin-3-yl)-2-phenyl-acetamide;
N-(1-{2-[4-(6-Amino-pyridin-2-yl)-phenyl]-ethyl}-pyrrolidin-3-yl)-2-(3-trifluoromethylphenyl)-acetamide;
N-(1-{2-[4-(6-Amino-pyridin-2-yl)-phenyl]-ethyl}-pyrrolidin-3-yl)-2-(4-tolyl)-acetamide;
N-(1-{2-[4-(6-Amino-pyridin-2-yl)-phenyl]-ethyl}-pyrrolidin-3-yl)-2-(4-methoxyphenyl)-acetamide;
2-(4-{2-[4-(6-Amino-pyridin-2-yl)-2-methoxy-phenyl]-ethyl}-piperazin-1-yl)-1-phenyl-ethanone;
1-(4-{2-[4-(6-Amino-pyridin-2-yl)-2-methoxy-phenyl]-ethyl}-piperazin-1-yl)-2-(4-fluoro-phenyl)-ethanone;
N-(1-{2-[4-(6-Amino-pyridin-2-yl)-phenyl]-ethyl}-pyrrolidin-3-yl)-2-cyclohexyl-acetamide;
2-(4-{2-[4-(6-Amino-pyridin-2-yl)-phenyl]-ethyl}-piperazin-1-yl)-1-(4-tolyl)-ethanone;
2-(4-{2-[4-(6-Amino-pyridin-2-yl)-phenyl]-ethyl}-piperazin-1-yl)-1-(4-methoxyphenyl)-ethanone;
2-(4-{2-[4-(6-Amino-pyridin-2-yl)-phenyl]-ethyl}-piperazin-1-yl)-1-(4-chlorophenyl)-ethanone;
2-(4-{2-[4-(6-Amino-pyridin-2-yl)-phenyl]-ethyl}-piperazin-1-yl)-1-(4-fluorophenyl)-ethanone;
2-(4-{2-[4-(6-Amino-pyridin-2-yl)-phenyl]-ethyl}-piperazin-1-yl)-1-cyclohexyl-ethanone;
1-(4-{2-[4-(6-Amino-pyridin-2-yl)-2-fluoro-phenyl]-ethyl}-piperazin-1-yl)-2-phenyl-ethanone;
6-{4-[2-(4-Isobutyl-piperazin-1-yl)-ethyl]-2-fluoro-phenyl}-pyridin-2-ylamine;
3-{2-[4-(6-Amino-pyridin-2-yl)-2-fluoro-phenyl]-ethyl}-3-aza-bicyclo[3.1.0]hex-6-ylamine;
2-(4-{2-[4-(6-Amino-pyridin-2-yl)-2-fluoro-phenyl]-ethyl}-piperazin-1-yl)-1-phenyl-ethanone;
1-(4-{2-[4-(6-Amino-pyridin-2-yl)-2-fluoro-phenyl]-ethyl}-piperazin-1-yl)-2-(4-fluoro-phenyl)-ethanone;
6-{4-[2-(4-Phenethyl-piperazin-1-yl)-ethyl]-2-fluoro-phenyl}-pyridin-2-ylamine;

2-(4-{2-[4-(6-Amino-pyridin-2-yl)-2-fluoro-phenyl]-ethyl}-piperazin-1-yl)-1-phenyl-ethanol;

{2-[4-(6-Amino-pyridin-2-yl)-2-fluoro-phenyl]-ethyl}-(3-oxa-9-aza-bicyclo[3.3.1]non-7-yl)-amine;

6-(4-{2-[4-(2-Amino-2-phenyl-ethyl)-piperazin-1-yl]-ethyl}-2-fluoro-phenyl)-pyridin-2-ylamine;

6-{4-[2-(4-Amino-2-fluoro-piperidin-1-yl)-ethyl]-2-fluoro-phenyl}-pyridin-2-ylamine;

2-(4-{2-[4-(6-Amino-pyridin-2-yl)-2-fuoro-phenyl]-ethyl}-piperazin-1-yl)-N-isopropyl-acetamide;

6-[4-(4-Amino-piperidin-1-ylmethyl)-2-fluoro-phenyl}-pyridin-2-ylamine;

6-{4-[2-(4-Amino-2,6-diethyl-piperidin-1-yl)-ethyl]-phenyl}-pyridin-2-ylamine;

6-{4-[2-(4-Amino-2,6-dibenzyl-piperidin-1-yl)-ethyl]-phenyl}-pyridin-2-ylamine;

{2-[4-(6-Amino-pyridin-2-yl)-phenyl]-ethyl}-(9-(4-fluoro)-benzyl-3-oxa-9-aza-bicyclo[3.3.1]non-7-yl)-amine;

{2-[4-(6-Amino-pyridin-2-yl)-phenyl]-ethyl}-(9-(4-chloro)-benzyl-3-oxa-9-aza-bicyclo[3.3.1]non-7-yl)-amine;

{2-[4-(6-Amino-pyridin-2-yl)-phenyl]-ethyl}-(9-(4-methyl)-benzyl-3-oxa-9-aza-bicyclo[3.3.1]non-7-yl)-amine; and {2-[4-(6-Amino-pyridin-2-yl)-phenyl]-ethyl}-(9-(4-methoxy)-benzyl-3-oxa-9-aza-bicyclo[3.3.1]non-7-yl)-amine.

The present invention also relates to a pharmaceutical composition for treating or preventing a condition selected from the group consisting of migraine inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's diseaise, chemical dependencies and addiction (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer in a mammal, including a human, comprising an amount of a compound of the formula I, or a pharmaceutically acceptable salt thereof that is effective in treating or preventing such condition, and a pharmaceutically acceptable carrier.

The present invention also relates to a method of treating or preventing a condition selected from the group consisting of migraine inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurode-generative diseases, neuron toxicity, Alzheimer's disease, chemical dependencies and addictions (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer in a mammal, including a human, comprising administering to said mammal an amount of a compound of the formula I, or a pharmaceutically acceptable salt thereof, that is effective in treating or preventing such condition.

The present invention also relates to a pharmaceutical composition for inhibiting nitric oxide synthase (NOS) in a mammal, including a human, comprising an NOS inhibiting effective amount of a compound of the formula I, or a pharmaceutically acceptable salt thereof and a pharmaceutically acceptable carrier.

The present invention also relates to a method of inhibiting NOS in a mammal, including a human, comprising administering to said mammal a NOS inhibiting effective amount of a compound of the formula I, or a pharmaceutically acceptable salt thereof.

The present invention also relates to a pharmaceutical composition for treating or preventing a condition selected from the group consisting of migraine, inflammatory diseases (e.g., asthma), stroke, acute and chronic pain, hypovolemic shock, traumatic shock, reperfusiori injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis ovulation, dilated cardiomyopathy, acute spinal cord injury, Huntington's disease, Parkinson's disease, glaucoma, macular degeneration, diabetic neuropathy, diabetic nephropathy and cancer in a mammal, including a human, comprising a NOS inhibiting effective amount of a compound of the formula I, or a pharmaceutically acceptable salt thereof and a pharmaceutically acceptable carrier.

The present invention also relates to a method of treating or preventing a condition selected from the group consisting of migraine, inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol or nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer in a mammal, including a human, comprising administering to said mammal a NOS inhibiting effective amount of a compound of the formula II, or a pharmaceutically acceptable salt thereof.

Compounds of formula I have chiral centers and therefore may exist in different enantiomeric and diasterilomic forms. This invention relates to all optical isomers and all stereoisomers of compounds of the formula I and mixtures thereof, and to all pharmaceutical compositions and methods of treatment defined above that contain or employ them, respectively.

Formulae I and II above include compounds identical to those depicted but for the fact that one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION
The compounds of the formula I may be prepared as described in the following reaction schemes and discussion. Unless otherwise indicated, $R^1$, $R^2$, $R^3$, $R^4$, $R^5$, $R^6$, $R^7$, $R^8$, $R^9$ and $R^{10}$ and structural formula I in the reaction schemes and discussion that follow are defined as above.
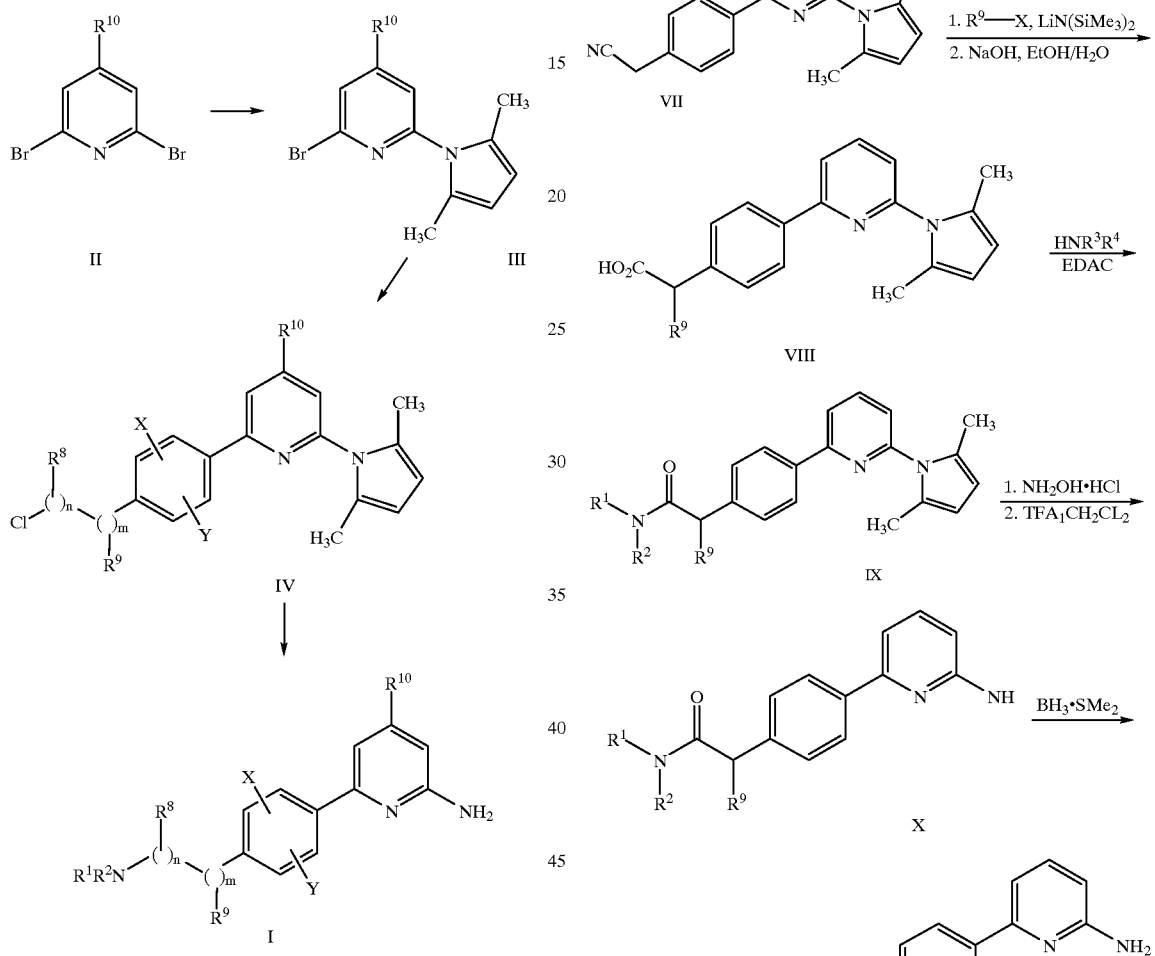
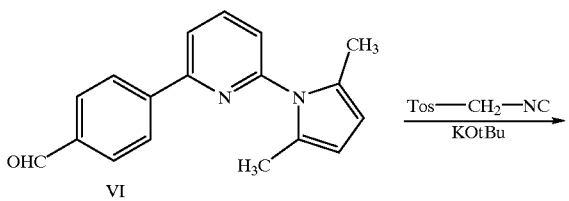
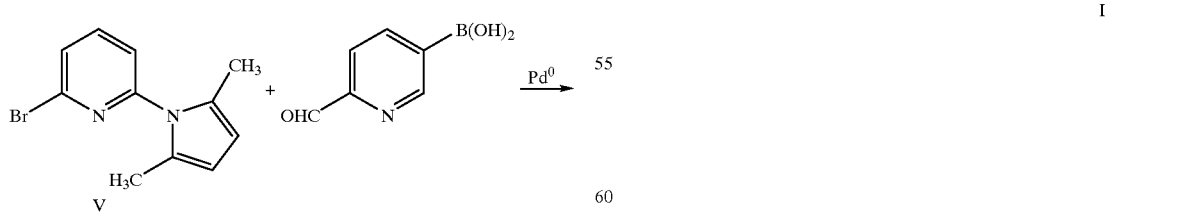

SCHEME 3
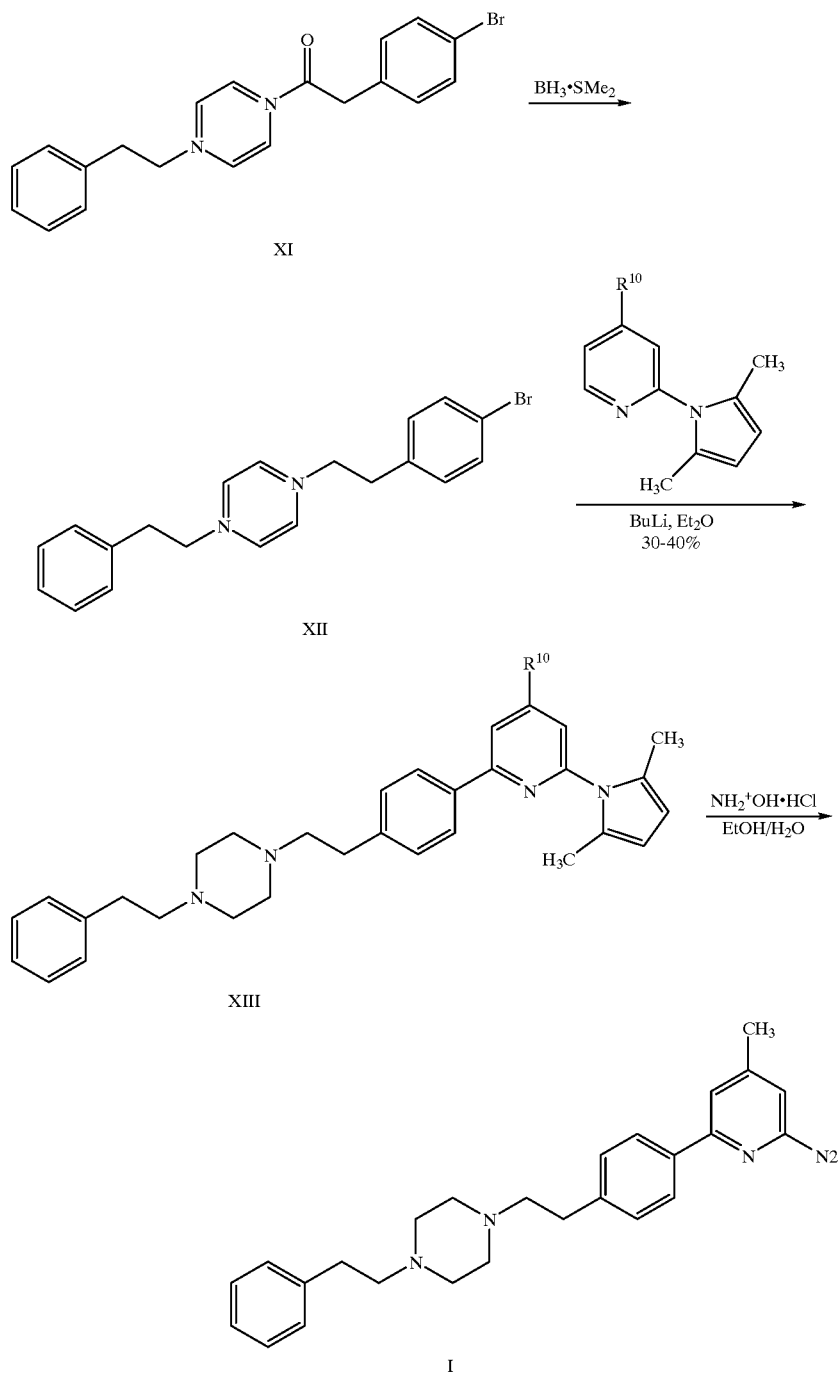

SCHEME 4
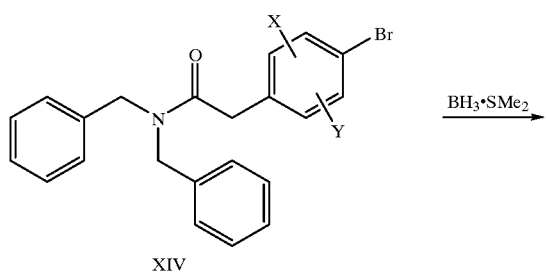
XIV
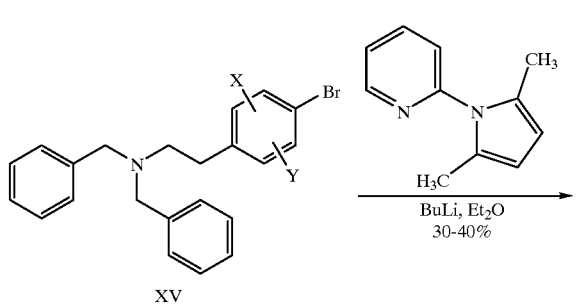
XV
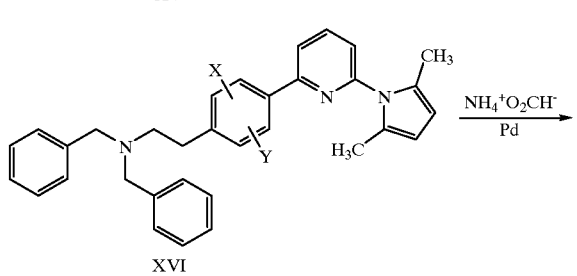
XVI
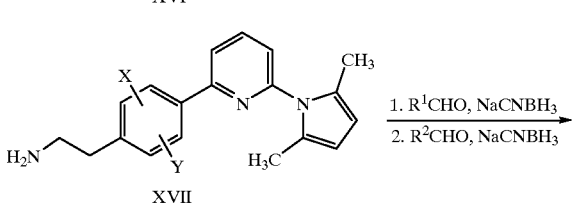
XVII
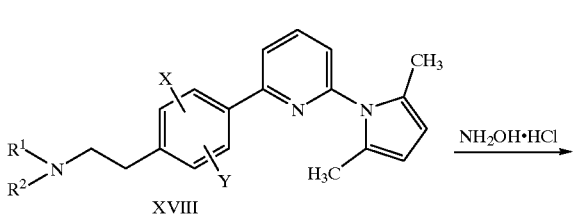
XVIII
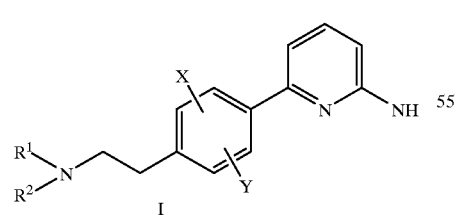
I
SCHEME 5
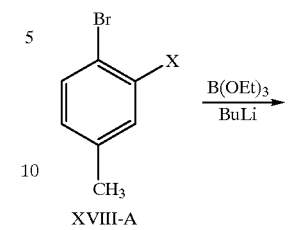
XVIII-A
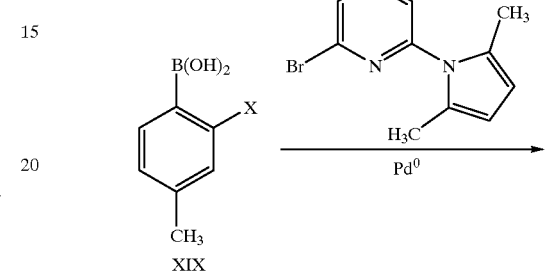
XIX
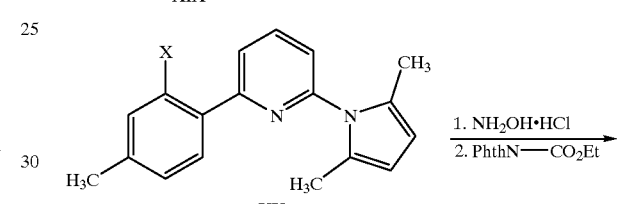
XX
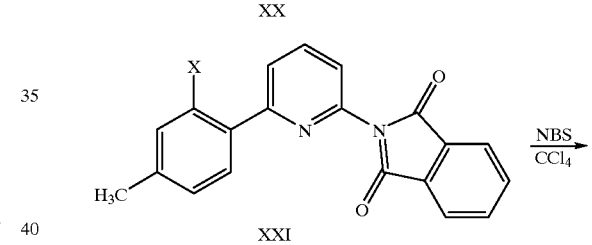
XXI
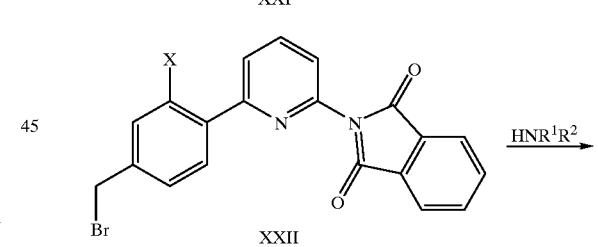
XXII
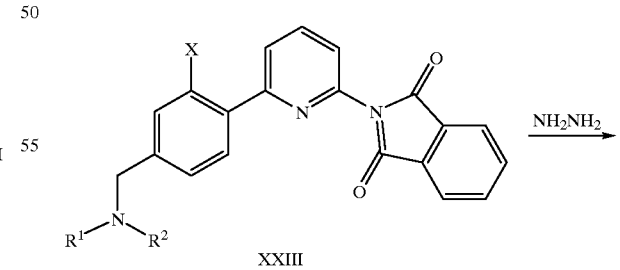
XXIII -continued

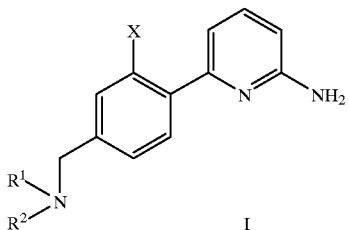

I

The starting materials used in the procedure of Scheme 1 are either commercially available, known in the art or readily obtainable form known compounds by methods that will be apparent to those skilled in the art. Referring to Scheme 1, the conversion of the compound of formula II into the compound of formula III may be carried out by first converting the compound of formula II into the corresponding 2-amino compound by reacting it with ammonia in a polar hydroxylic or polar nonhydroxylic solvent at a temperature of about 100° C. to about 250° C. and a pressure of about 50 to about 500 p.s.i. for about 1 to 24 hours, preferably using a stainless steel bomb. The pyrrolyl group is then added using hexane-2,5-dione, either neat or in a non-polar solvent such as toluene, in the presence of an acidic catalyst such as acetic acid or hydrochloric acid, at a temperature from about room temperature to about the reflux temperature, generally the latter, for about 1 to 72 hours.

The conversion of the compound of formula III formed in the above reaction into the compound of formula IV is carried out using a transition metal mediated coupling reaction with a suitably substituted aryl iodide or bromide. More specifically, the lithium derivative of the compound of formula III is generated in an ethereal or hydrocarbon solvent at a temperature from about −100° C. to about room temperature, preferably at about −78° C., using an alkyl lithium such as butyl lithium, for about 10 to 120 minutes, followed by addition of a catalytic metal reagent such as zinc chloride and warming to room temperature to effect transmetalation. This is followed by addition of the aryl iodide (e.g., 1-iodo-4-(2-chloroethyl)benzene) or bromide and a transition mietal, such as palladium in the form of tetrakistriphenylphosphine palladium, followed by heating to a temperature of about 30° C. to about 100° C., typically to about the reflux temperature of the solvent, for about 1 to 24 hours.

The conversion of the compound of formula IV to the desired compound of formula I is accomplished by first removing the pyrrolyl protecting group using, typically, hydroxylamine or hydroxylamine hydrochloride in a polar, protic solvent such as an alcohol, at a temperature of from about room temperature to about 150° C., generally at about the reflux temperature of the solvent, for about 1 to 72 hours. This is followed by addition of the appropriate $NR^1R^2$ group by displacement of the chloro group with an amine of the formula $HNR^1R^2$ using a polar, aprotic or a polar, protic solvent such as an alcohol, dimethylformamide (DMF), methylisobutylketone or N-methylpyrrolidone (NMP), optionally in the presence of a catalyst such as sodium iodide, at ia temperature of from about room temperature to about 200° C., typically at about the reflux temperature of the solvent, or at about 140° C. in the cases of dimethylformamide and N-methylpyrrolidone, for about 100 hours, generally from about 12 to 24 hours.

Referring to Scheme 2, ciompound VI is prepared by reacting V with p-formylbenzeneboronic acid in a solvent consisting of an alcohol, preferably ethanol, optionally mixed with water of a halogenated hydrocarbon, at a temperature from 25° C. to 150° C., for a time from 1 to 24 hours, using a palladium-based catalyst, either palladium-zero or palladium-two oxidation state, typically with phosphine ligands, preferably tetrakis-triphenylphosphine palladium. Compound VII is prepared by reacting VI with tosylmethylisocyanide in the presence of potassium t-butoxide and ethanol, in an ethereal solvent such as 1,2-dimethoxyethane, at a temperature from −100° C. to 100° C., for a time from 1 to 24 hours. Compound VIII is prepared from VII by basic hydrolysis of the nitrile using an alkali metal hydroxide in an aqueous alcohol-based solvent, such as aqueous ethanol, at a temperature from 25° C. to 125° C., for a time from 30 minutes to 48 hours. Compound IX is prepared from VIII by dehydrative coupling with ammonia, a primary amine, or a secondary amine effected by a dehydrating agent such as a carbodiimide, for example, N-ethyl-N-(dimethylaminopropyl)-carbodiimide, in a solvent from a halogenated hydrocarbon or N,N-dialkylamide, such as dirriethylformamide, at a temperature from 0° C. to 100° C., for a time from 1 to 48 hours. Compound X is prepared from IX by deblocking using hydroxylamine hydrochloride in an aqueous or alcoholic solvent, preferably aqueous ethanol, at a temperature from 25° C. to 100° C., for a time from 1 to 48 hours, and may include deblocking a protecting group such a the t-butoxycarbonyl group, by reaction with trifluoroacetic acid, or a related polyhalogenated acetic acid, or a gaseous hydrogen halide, such as HCl, in a halogenated hydrocarbon, ethereal solvent or ethyl acetate, at a temperature from −70° C. to 100° C., for a time from 10 minutes to 24 hours. The final compound in Scheme 2, I, is prepared by reduction of X with borane, a trialkyl borane, alane, or lithium aluminum hydride in an ethereal solvent, such as ethyl ether or tetrahydrofuran, at a temperature from −100° C. to 100° C., for a time from 30 minutes to 24 hours, and optionally using cesium fluoride and an alkali metal or alkaline earth carbonate in an aqueous alcoholic solvent, at a temperature from 25° C. to 125° C. for a time from 1 to 72 hours.

Referring to Scheme 3, compound XI is prepared by dehydrative coupling of N-phenethylpiperazine with 4-bromophenylacetic acid using a carbodiimide-based dehydrating reagent, such as N-ethyl, N-(dimethylaminopropyl)-carbodiimide, in a solvent such as a halogenated hydrocarbon or dialkylamide-based solvent, such as dimethylformamide, at a temperature from 0° C. to 100° C. in a time from 1 to 48 hours. Compound XI was converted to compound XII by reduction with borane, a trialkyl borane, alane, or lithium aluminum hydride in an ethereal solvent, such as ethyl ether or tetrahydrofuran, at i temperature from −100° C. to 100° C., for a time from 30 minutes to 24 hours, and optionally using cesium fluoride and an alkali metal or alkaline earth carbonate in an aqueous alcoholic solvent, at a temperature from 25° C. to 125° C. for a time from 1 to 72 hours. Compound XII is then converted to the organolithium derivative in the presence of an organolithium reagent, such as butyl lithium, and added to 4-methyl-2-(2,5-dimethylpyrrolyl)-pyridine in an ethereal solvent, such as ethyl ether, at a temperature from −70° C. to 70° C. in a time from 30 minutes to 24 hours. The final compound in Scheme 3, compound I, is prepared by deblocking using hydroxylamine hydrochloride in an aqueous or alcoholic solvent, preferably aqueous ethanol, at a temperature from 25° C. to 100° C., for a time from 1 to 48 hours.

Referring to Scheme 4, compound XIV is prepared by dehydrative coupling of dibenzylamine with 4-bromophenylacetic acid effected by a dehydrating agent such as a carbodiimide, for example, N-ethyl-N-(dimethylaminopropyl)-carbodiimide, in a solvent from a halogenated hydrocarbon or N,N-dialkylamide, such as dimethylformamide, at a temperature from 0° C. to 100° C., for a time from 1 to 48 hours. Compound XIV is converted to compound XV by reduction with borane, a trialkyl borane, alane, or lithium aluminum hydride in an ethereal solvent, such as ethyl ether or tetrahydrofuran, at a temperature from −100° C. to 100° C., for a time from 30 minutes to 24 hours, and optionally using cesium fluoride and an alkali metal or alkaline earth carbonate in an aqueous alcoholic solvent, at a temperature from 25° C. to 125° C. for a time from 1 to 72 hours. Compound XV is then converted to the organolithium derivative in the presence of an organolithium reagent, such as butyl lithium, and added to 2-(2,5-dimethylpyrrolyl)-pyridine in an ethereal solvent, such as ethyl ether, at a temperature from −70° C. to 70° C. in a time from 30 minutes to 24 hours to provide compound XVI. Compound XVII is then prepared from compound XVI by hydrogenolysis with hydrogen or ammonium formate in the presence of a noble metal catalyst, such as palladium, in an ethereal, halogenated hydrocarbon, alcoholic, or aqueou.s alcoholic solvent, at a temperature from 0° C. to 100° C. for a time from 30 minutes to 24 hours. Compound XVIII is then prepared from compound XVII by reductive amination with an aldehyde or ketone in the presence of a borohydride-based reagent such as sodium cyanoborohydride or sodium triacetoxyborohydride, in an ethereal, halogenated hydrocarbon, alcoholic, or aqueous-alcoholic solvent, at a temperature from 0° C. to 100° C. for a time from 1 to 72 hours. Conversion of compound XVIII to I by deblocking is carried out by using hydroxylamine hydrochloride in an aqueous or alcoholic solvent, preferably aqueous ethanol, at a temperature from 25° C. to 100° C., for a time from 1 to 48 hours.

Referring to Scheme 5, compound XIX is prepared by reaction of the known (EP 470794 A1, see *Chem. Abs.*, 116:193935) 2-bromo-5-methylanisole with an alkyl lithium, typically butyl lithium, in an ethereal or hydrocarbon solvent, at a temperature from −100° C. to 0° C. for 1 minute to 24 h, followed by addition of an alkyl or aryl borate ester, typically triethyl borate, at a temperature from −100° C. to 0° C., and stirred while the temperature was adjusted to 0° C. to the reflux temperature of the solvent, typically 65° C., for 1 to 48 hours. Compound XIX is converted to XX by reaction with 6-bromo-2-(2,5-dimethylpyrrolyl)pyridine and an alkali carbonate in a solvent consisting of an alcohol, preferably ethanol, optionally mixed with water of a halogenated hydrocarbon, at a temperature from 25° C. to 150° C., for a time from 1 to 24 hours, using a palladium-based catalyst, either palladium-zero or palladium-two oxidation state, typically with phosphine ligands, preferably tetrakis-triphenylphosphine palladium. Compound XXI was prepared from XX by first deblocking using hydroKylamine hydrochloride in an aqueous or alcoholic solvent, preferably aqueous ethanol, at a temperature from 25° C. to 100° C., for a time from 1 to 48 hours, followed by reaction with N-carbethoxyphthalimide in a hydrocarbon solvent at a temperature from room temperature to the reflux temperature of the solvent or 180° C., typically 110° C., for a time from 1 to 48 hours. Conversion of compound XXI to XXII was carried out by reaction with N-bromo succinimide in a chlorinated hydrocarbon solvent, typically carbon tetrachloride, with a catalytic: amount of a radical initiator such as azobisisobutyronitrile, at a temperature from room temperature to 100° C. for a time from 10 minutes to 24 hours. Compound XXII was then converted to XXIII by reaction with an amine, such as phenethylamine, in a hydrocarbon, halogenated hydrocarbon, ethereal, or polar aprotic solvent, such as acetonitrile, with an alkali carbonate base, at a temperature from room temperature to 100° C. for a time from 10 minutes to 48 hours. Compound XXIII was then converted to the final product in Scheme 5, I, by deblocking using hydrazine in an alcoholic, aqueous, or ethereal solvent, at a temperature from room temperature to 150° C. for a time from 1 to 72 hours.

The preparation of other compounds of the formula I not specifically described in the foregoing experimental section can be accomplished using combinations of the reactions described above that will be apparent to those skilled in the art.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The compounds of formulae I ("the active compounds of this invention") which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The active compounds of this invention and their pharmaceutically acceptable salts are useful as NOS inhibitors i.e., they possess the ability to inhibit the NOS enzyme in mammals, and therefore they are able to function as therapeutic agents in the treatment of the aforementioned disorders and diseases in an afflicted mammal.

The active compounds of this invention and their pharmaceutically acceptable salts can be administered via either the oral, parenteral or topical routes. In general, these compounds are most desirably administered in dosages ranging from about 0.01 to about 250 mg per day, in single or divided doses (i.e., from 1 to 4 doses per day), although variations will necessarily occur depending upon the species, weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The active compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous medial and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compounds of the present invention topically when treating inflammatory conditions of the skin and this may be done by way of creams, jellies, gels, pastes, patches, ointments and the like, in accordance with standard pharmaceutical practice.

The ability of compounds cof the formulae I to inhibit NOS may be determined using procedures described in the literature. The ability of compounds of the formulae I to inhibit endothelial NOS may be determined by using the procedures described by Schmidt et al. in *Proc. Natl. Acad. Sci. U.S.A.*, 88, pp. 365–369 (1991) and by Pollock et al., in *Proc. Natl. Acad. Sci. U.S.A.*, 88, pp. 10480–10484 (1991). The ability of compounds of the formulae I to inhibit inducible NOS may be determined using the procedures described by Schmidt et al., in *Proc. Natl. Acad. Sci. U.S.A.*, 88 pp. 365–369 (1991) and by Garvey et al. in *J. Biol. Chem.*, 269, pp. 26669–26676 (1994). The ability of the compounds of the formula I to inhibit neuronal NOS may be determined using the procedure described by Bredt and Synder in *Proc. Natl. Acad. Sci. U.S.A.*, 87, 682–685 (1990).

Of 100 compounds of the formula I that were tested, all exhibited an $IC_{50} < 10\,\mu M$ for inhibition of either inducible or neuronal NOS.

The present invention is illustrated by the following examples. It will be understood, however, that the invention is not limited to the specific details of these examples. Melting points are uncorrected. Proton nuclear magnetic resonance spectra ($^1H$ NMR) and $C^{13}$ nuclear magnetic resonance spectra were measured for solutions in deuterochloroform ($CDCl_3$) or in $CD_3OD$ or $CD_3SOCD_3$ and peak positions are expressed in parts per million (ppm) downfield from tetramethylsilane (TMS). The peak shapes are denoted as folloys: s, singlet; d, doublet; t, triplet; q, quartet, m, multiplet, b, broad.

EXAMPLE 1

6-{4-[2-(4-Phenethyl-piperazin-1-yl)-ethyl]-phenyl}-pyridin-2-ylamine

A. 2-Amino-6-bromopyridine

In a 300 mL bomb were placed 40 g(168 mmol) 2,6-dibromopyridine and 125 mL 30% aqueous ammonium hydroxide, and the bomb sealed and heated at 170° C., 400 psi, for 3 hours. After cooling, the contents were extracted into ethyl acetate, washed with brine and dried over sodium sulfate. Then the solvent was evaporated. The residue was chromatographed on silica gel using 2% methanol in methylene chloride as eluant to afford 19.5 g(67%) or a light yellow solid.

$^1H$-NMR ($CDCl_3$,d): 106.8, 116.8, 139.9, 158.8. MS (%): 173/175 (parent, $B^{79}/Br^{81}$, 100/98).

B. 2-Bromo-6-(2,5-dimethylpyrrol-1-yl)pyridine

To a 1 L round-bottomed flask equipped with Dean-Stark trap, condenser, and nitrogen inlet were added 21.3 g(123 mmol) 2-amino-6-bromopyridine, 400 mL toluene, 14.1 g(123 mmol) acetonylacetone, and 20 drops acetic acid. The reaction was refluxed 5 days (tlc in 1/1:ethyl acetate/hexane, $R_f$=0.8 (product), 0.5 (starting material)), cooled, poured into ethyl acetate, washed with saturated aqueous sodium bicarbonate solution and brine, dried over sodium sulfate, and evaporated. The residue was chromatographed on silica gel using 5% methanol in methylene chloride to afford 14.4 g(47%) of the product as a low-melting yellow solid.

$^1H$-NMR ($CDCl_3$, $\delta$): 2.16 (s, 6H), 5.89 (s, 2H), 7.17 (d, J-7, 1H), 7.47 (d, J=7, 1H), 7.67 (t, J=8, 1H). $^{13}C$-NMR ($CDCl_3$, $\delta$): 13.3, 107.6, 120.3, 126.4, 128.7, 139.8, 140.6, 151.9. MS (%): 251/253 (parent, $Br^{79}Br^{81}$, 100/98).

C. 2-(4-Iodophenyl)ethanol)

To a 500 mL 3-neck round-bottomed flask equipped with dropping funnel and nitrogen inlet were added 20.5 g (150 mmol) 2-(4-aminophenyl)ethanol and 100 mL hot water to give a solution A solution of 3.5 mL concentrated sulfuric acid in 10 mL water was added dropwise, and the solution cooled to 4° C. A solution of 13.5 mL concentrated sulfuric acid in 50 mL water was added dropwise while maintaining the temperature between 0° C. and 5° C., then a solution of 13 g (188 mmol) sodium nitrite in 50 mL water was added dropwise at the same temperature. After stirring 30 min at 0–5° C., a solution of 85 g (512 mmol) potassium iodide in 100 mL water was added dropwise, and the reaction was allowed to warm to room temperature and stirred for 2 hour. The reaction was then heated to 60° C. for 30 min, cooled to room temperature, and extracted into ethyl acetate (2×250 mL). The ethyl acetate layer was washed with aqueous sodium thiosulfate solution and brine, dried over sodium sulfate, and evaporated. The residue was chromatographed on silica gel using 20% and 50% ethyl acetate in hexane as eluant to afford 30.7 g (82.5%) of the product as a light yellow solid.

$^1$H-NMR (CDCl, δ): 2.74 (m, 2H), 3.79 (m, 2H), 6.93 (m, 2H), 7.57 (m, 2H). $^{13}$C-NMR (CDCl$_3$, δ): 38.6, 63.3, 91.7, 131.1, 137.6, 138.3. MS(%): 247 (parent, 23).

D. 2-(4-Iodophenyl)ethylchloride

To a 500 mL round-bottomed flask equipped with dropping funnel, condenser and N$_2$ inlet were added 307 g (124 mmol) 2-(4-iodophenyl)ethanol, 200 mL chloroform, and 10.0 mL (124 mmol) pyridine. A solution of 13.5 mL (186 mmol) thionyl chloride in 50 mL chloroform was added dropwise over 15 min, and the reaction then heated at reflux for 2 hr. The reaction was cooled, the solvent evaporated, and the residue taken up in ethyl acetate, washed with 1 N hydrochloric acid, water, saturated aqueous sodium bicarbonate solution and brine, dried, and evaporated. The resulting oil was chromatographed on silica gel using 20% ethyl acetate in hexane as eluant to afford 32.6 g (99%) of the product as an oil.

$^1$H-NMR (CDCl$_3$, δ): 3.00 (t, J=7, 2H), 3.68 (t, J=7, 2H), 6.99 (m, 2H), 7.63 (m, 2H). $^{13}$C-NMR (CDCl$_3$, δ): 38.6, 44.6, 92.3, 128.8, 130.9, 137.7.

E. 2-(2,5-Dimethylpyrrol-1-yl)-6-(4-(2-chloroethyl)phenyl)-pyridine

To a 1 L 3-neck round-bottomed flask equipped with addition funnel and nitrogen inlet were added 10.0 g (40 mmol) 2-bromo-6-(2,5-dimethylpyrrol-1-yl)pyridine and 200 mL dry tetrahydrofuran. The solution was cooled at −78° C., and a 1.6 M solution of butyl lithium in hexane (25 mL, 40 mmol) was added dropwise over 10 min. The reaction was stirred at −78° C. for 20 min, then a 1.0 M solution of zinc chloride in ether (100 mL, 100 mmol) was added dropwise over 40 min keeping the temperature at −70° C. The reaction was then allowed to warm to room temperature, and 11.0 g (40 mmol) 2-(4-iodophenyl)ethylchloride was added, followed by 200 mg tetrakistriphenylphosphine palladium. The reaction was refluxed for 3 hours, cooled, and filtered through Celite. The filtrate was evaporated, and the residue taken up in ethyl acetate, washed with brine, dried over sodium sulfate, and evaporated. The residue was filtered through silica gel with methylene chloride, concentrated, and chromatographed on silica gel using 1% ethyl acetate in hexane as eluant to afford 7.3 g (59%) of the product as an oil.

$^1$H-NMR (CDCl$_3$, δ): 2.19 (s, 6H), 3.10 (t, J=7, 2H), 3.73 (t, J-7, 2H), 5.91 (s, 2H), 7.12 (d, J=7, 1H), 7.32 (d, J=8, 2H), 7.72 (m, 1H), 7.82 (m, 1H), 8.01 (m, 2H). $^{13}$C-NMR (CDCl$_3$, δ): 13.5, 28.9, 44.7, 106.9, 118.1, 119.8, 127.1, 128.7, 129.3, 137.1, 138.6, 139.4, 151.7, 156.6. MS (%): 311 (parent+1, 100).

F. 6-(4-(2-chloroethyl)phenyl)-pyridin-2-ylamine hydrochloride

To a 500 mL round-bottomed flask equipped with condenser and nitrogen inlet were added 9.0 g (29.0 mmol) 2-(2,5-dimethylpyrrol-1-yl)-6-(4-(2-chloroethyl)phenyl)-pyridine, 250 mL ethanol, 50 mL water, and 10.1 g (145 mmol) hydroxylamine hydrochloride. The reaction was refluxed for 36 hours, cooled, and the solvent was evaporated. The residue was taken up in ethyl acetate, washed with saturated aqueous sodium bicarbonate solution and brine, dried over sodium sulfate, and evaporated. The residue was chromatographed on silica gel using 2% methanol in methylene chloride as eluant to afford 7.8 g (88%) of the product as a light brown solid.

$^1$H-NMR (CDCl$_3$, δ): 2.97 (broad s, 2H, NH$_2$), 3.05 (t, J=7, 2H), 3.68 (t, J=7, 2H), 6.85 (m, 1H), 6.88 (m, 1H), 7.33 (m, 2H), 7.68 (6, J=7, 1H), 7.78 (m, 2H). MS (%): 232 (parent, 60), 183 (100).

G. 6-{4-[2-(4-Phenethyl-piperazin-1-yl)-ethyl]-phenyl}-pyridin-2-ylamine

To a 50 mL round-bottomed flask equipped with condenser and N$_2$ inlet were added 20 mg (0.65 mmol) 6-(4-(2-chloroethyl)phenyl)-pyridin-2-ylamine hydrochloride, 125 mg (0.98 mmol) diisopropylethylamine, 208 mg (1.9 mmol) sodium carbonate, and 5 mL dry dimethylformamide. The reaction was heated at reflux for 18 hours, cooled, and poured into water, then extracted into ethyl acetate. The organic layer was extracted into 1 N hydrochloric acid, after which the aqueous layer washed with fresh ethyl acetate, basified with 1 N aqueous sodium hydroxide solution, and then extracted into ethyl acetate. The organic layer was washed with brine, dried over sodium sulfate, and evaporated. The residue was chromatographed on silica gel using 2% and 5% methanol in methylene chloride as eluant to afford 71 mg (28%) of the product as a tan solid mp 111–113° C.

$^1$H-NMR (CDCl$_3$, δ): 2.64 (m, 6H), 2.84 (m, 2H), 4.52 (broad s, 2H), 6.41 (d, J=8, 1H), 7.04 (d, J=7, 1H), 7.1–7.3 (m, 7H), 7.45 (t, J=8, 1H), 7.84 (m, 2H). $^{13}$C-NMR (CDCl$_3$, δ): 33.3, 33.6, 53.2, 60.3, 60.5, 106.9, 110.7, 126.1, 126.8, 128.4, 128.7, 128.9, 137.6, 138.3, 140.3, 140.9, 156.1, 158.2. MS (%): 387 (parent+1, 100). Anal. Calc'd for C$_{25}$H$_{30}$N$_4$.1/2H$_2$O: C, 75.91, H, 7.90, N, 14.16. Found: C, 76.00, H, 8.01, N, 14.17.

EXAMPLE 2

6-((2-(6-(t-butoxycarbonylamino)-3-azabicyclo[3.1.0]hex-3-yl)ethyl)phenyl)-pyridin-2-ylamine The title compound was prepared using the procedure described in Example 1G using 6-(t-butoxycarbonylamino)-3-aza-bicyclo[3.1.0]hexane, in 48% yield as a brown oil.

$^1$H-NMR (CDCl$_3$, δ): 1.43 (s, 9H), 1.50 (m, 1H), 1.70 (m, 1H), 2.40 (m, 1H), 2.64 (m, 1H), 2.75 (m, 1H), 3.15 (m, 1H), 4.46 (m, 1H), 6.42 (d, J=8, 1H), 7.05 (d, J=7, 1H), 7.22 (m, 2H), 7.47 (t, J=8, 1H), 7.81 (d, J=8, 1H). $^{13}$C-NMR (CDCl$_3$, δ): 28.4, 31.4, 35.2, 36.4, 54.5, 56.9, 79.4, 106.8, 110.75, 126.7, 128.8, 137.4, 138.3, 141.1, 156.1, 158.2, 162.5. MS (%): 395 (parent, 100).

3-{2-[4-(6-Amino-pyridin-2-yl)-phenyl]-ethyl}-3-aza-bicyclo[3.1.0]hex-6-ylamine

To a 25 mL round-bottomed flask equipped with nitrogen inlet were added 135 mg (0.342 mmol) 6-((2-(6-(t-butoxycarbonylamino)-3-azabicyclo[3.1.0]hex-3-yl)ethyl)phenyl)-pyridin-2-ylamine, 10 mL methylene chloride, and 3 mL trifluoroacetic acid. After stirring 30 min at room temperature, the reaction was evaporated and the residue triturated with tetrahydrofuran and ethyl ether to afford 195 mg (76%) of a yellowish solid, mp 187–190° C.

$^1$H-NMR (CDCl$_3$, δ): 2.33 (m, 2H), 2.95 (m, 1H), 3.10 (m, 3H), 3.47 (m, 2H), 3.6–4.0 (m, 2H), 6.95 (d, J=8, 1H), 7.13 (d, J=7, 1H), 7.49 (m, 2H), 7.76 (m, 2H), 7.94 (t, J=7, 1H). $^{13}$C-NMR (free base in CDCl$_3$, δ): 25.8, 32.7, 35.2, 55.0, 57.3, 106.8, 110.8, 126.7, 128.9, 137.5, 138.3, 141.0, 156.1, 158.2. MS (%): 295 (parent+1, 100). Anal. Calc'd for C$_{18}$H$_{22}$N$_4$.3(C$_2$HF$_3$O$_2$): C, 45.29, H, 3.96, N, 8.80. Found: C, 45.30, H, 3.93, N, 8.80.

EXAMPLE 3

1-(4-{2-[4-(6-Amino-pyridin-2-yl)-phenyl]-ethyl}-piperazin-1-yl)-2-phenyl-ethanone A. 6-((2-(4-(t-butoxycarbonyl)piperazin-1-yl)ethyl)phenyl)-pyridin-2-ylamine The title compound was prepared using the procedure described in Example 1G using t-butoxycarbonylpiperazine in 57.5% yield with methylisobutylketone as solvent at reflux for 5 days as a light brown solid.

$^1$H-NMR (CDCl$_3$, δ): 1.45 (s, 9H), 2.46 (m, 4H), 2.61 (m, 2H), 2.84 (m, 2H), 3.45 (m, 4H) 4.48 (broad, s, 2H), 6.42 (d, J=8, 1H), 7.05 (d, J=7, 1H), 7.25 (m, 2H), 7.47 (t, J=8, 1H), 7.84 (m, 2H). $^{13}$C-NMR (CDCl$_3$, δ): 28.4, 33.3, 53.0, 60.3, 106.9, 110.7, 126.8, 128.9, 137.7, 138.3, 140.7, 154.8, 156.0, 158.2. MS (%): 383 (parent+1, 14), 283 (70), 197 (72), 143 (70), 99 (100).

B. 6-((2(piperazin-1-yl)ethyl)phenyl)-pyridin-2-ylamine:

The title compound was prepared using the procedure described in Example 2B in 94% yield as a light brown solid.

$^1$H-NMR (CDCl$_3$, δ): 1.69 (s, 1H), 2.49 (broad s, 4H), 2.58 (m, 2H), 2.85 (m, 2H), 2.91 (m, 4H), 4.49 (broad s, 2H), 6.41 (d, J=8, 1H), 7.04 (d, J=7, 1H), 7.26 (m, 2H), 7.46 (t, J=8, 1H), 7.84 (m, 2H). $^{13}$C-NMR (CDCl$_3$, δ): 33.1, 46.1, 54.5, 61.0, 106.8, 110.7, 126.8, 128.9, 137.6, 138.3, 140.9, 156.1, 156.2. MS (%): 283 (parent, 100).

C. 1-(4-{2-[4-(6-Amino-pyridin-2-yl)-phenyl]-ethyl}-piperazin-1-yl)-2-phenyl-ethanone To a 50 mL round-bottomed flask equipped with nitrogen inlet were added 150 mg (0.53 mmol) 6-((2-(piperazin-1-yl)ethyl)phenyl)-pyridin-2-ylamine, 15 mL methylene chloride, 0.070 mL (0.53 mmol) triethylamine, and 0.070 mL (0.53 mmol) phenylacetyl chloride. The reaction was stirred 1 hour at room temperature. The residue was chromatographed on silica gel using 2.5% methanol in methylene chloride to afford 126 mg (59%) of the product as a tan solid, mp 135–137° C.

$^1$H-NMR CDCl$_3$, δ): 2.31 (m, 2H), 2.48 (m, 2H), 2.60 (m, 2H), 2.79 (m, 2H), 3.45 (m, 2H), 3.67 (m, 2H), 3.73) s, 2H), 4.53 (broad s, 2H), 6.42 (d, J-8, 1H) 7.03 (d, J=7, 1H), 7.2–7.4 (m, 7H), 7.47 (t, J=8, 1H), 7.82 (m, 2H). $^{13}$C-NMR (CDCl$_3$, δ): 33.1, 41.0, 41.7, 46.0, 52.6, 53.0, 59.9, 107.0, 110.7, 126.8, 126.9, 128.6, 128.7, 128.9, 135.1, 137.6, 138.4, 140.5, 155.9, 158.2, 169.4. MS (%): 401 (parent+1, 100). Anal. Calc'd for C$_{25}$H$_{28}$N$_4$O.1/4H$_2$O: C, 74.14, H, 7.04, N, 13.83. Found: C, 74.48, H, 7.05, N, 13.86.

EXAMPLE 4

4-{2-[4-(6-Amino-pyridin-2-yl)-phenyl]-ethyl}-piperazine-1-carboxylic Acid phenylamide To a 50 mL round-bottomed flask equipped with nitrogen inlet were added 150 mg (0.53 mmol) 6-((2-(piperazin-1-yl)ethyl)phenyl)-pyridin-2-ylamine, 60 uL (0.53 mmol) phenylisocyanate, 10 mL 1,2-dichloroethane, 10 mL ethyl acetate, and 64 mg (0.53 mmol) 4-dimethylaminopyridine. The reaction was stirred at room temperature for 14 hours, evaporated, and chromatographed on silica gel using 5% methanol in methylene chloride as eluant to afford 205 mg (96%) of the product as a foam, mp 60° C.

$^1$H-NMR (CDCl$_3$, δ): 2.55 (m, 4H), 2.68 (m, 2H), 2.85 (m, 2H), 3.52 (m, 4H), 4.49 (broad s, 2H), 6.39 (s, 1H), 6.42 (d, J=8, 1H), 7.0–7.4 (m, 7H), 7.48 (t, J=8, 1H), 7.86 (m, 2H). $^{13}$C-NMR (CDCl$_3$, δ): 33.3, 44.1, 52.8, 60.1, 106.9, 110.8, 119.9, 123.1, 126.9, 128.9, 137.7, 138.4, 139.0, 140.6, 155.0, 156.0, 158.2. MS (%): 402 (parent+1, 100). Anal. Calc'd for C$_{24}$H$_{27}$N$_5$O.1/2H$_2$O: C, 70.22, H, 6.88, N, 17.06. Found: C, 70.27, H, 6.60, N, 17.22.

EXAMPLE 5

1-(4-{2-[4-(6-Amino-pyridin-2-yl)-phenyl]-ethyl}-piperazin-1-yl)-2-(4-fluoro-phenyl)-ethanone To a 50 mL round-bottomed flask equipped with nitrogen inlet were added 200 mg (0.71 mmol) 6-((2-(piperazin-1-yl)ethyl)phenyl)-pyridin-2-ylamine, 10 mL dry dimethyformamide, 109 mg (0.71 mmol) 4-fluorophenylacetic acid, 204 mg (1.1 mmol) ethyl(3-dimethylaminoproryl)carbodiimide, and 0.36 mL (2.1 mmol) diisopropylethylamine. The reaction was stirred at room temperature for 18 hours, poured into water and extracted into ethyl acetate. The organic layer was extracted into 1 N hydrochloric acid, the aqueous layer washed with fresh ethyl acetate, and the aqueous layer basified with 1 N aqueous sodium hydroxide solution and extracted into ethyl acetate. The organic layer was washed with brine, dried over sodium sulfate, and evaporated. The residue was chromatographed on silica gel using 3% methanol in methylene chloride to afford 100 mg (34%) of the product as a tan solid, mp 143–145° C.

$^1$H-NMR (CDCl$_3$, δ): 2.34 (m, 2H), 2.46 (m, 2H), 2.60 (m, 2H), 2.79 (m, 2H), 3.45 (m, 2H), 3.66 (m, 2H), 3.67 (s, 2H), 4.52 (broad s, 2H), 6.41 (d, J=8, 1H), 6.9–7.3 (m, 6H), 7.46 (t, J=8, 11H), 7.82 (m, 2H). $^{13}$C-NMR (CDCl$_3$, δ): 33.2, 39.9, 41.8, 46.0, 52.7, 53.1, 59.9, 106.9, 110.7, 115.4, 115.7, 126.8, 128.9, 130.2, 130.3, 130.7, 130.8, 137.7, 138.3, 140.5, 155.9, 158.2, 160.1, 163.4, 169.2. MS (%): 419 (parent+1, 100). Anal. Calc'd for C$_{25}$H$_{27}$FN$_4$O: C, 71.75, H 6.50, N, 13.39. Found: C, 71.46, H, 6.68, N, 13.39.

EXAMPLE 6

6-{4-[2-(3,4-Dihydro-1H-isoquinolin-2-yl)-ethyl]-phenyl}-pyridin-2-ylamine

Prepared as in Example 1, using 1,2,3,4-tetrahydroisoquinoline, in 51% yield, mp 130–132° C.

$^1$H-NMR (CDCl$_3$, δ): 2.8–3.0 (m, 8H), 3.76 (bs, 2H), 6.39 (d, J=8, 1H), 7.0–7.3 (m, 7H), 7.46 (t, J=8, 1H), 7.87 (d, J=8, 2H). $^{13}$C-NMR (CDCl$_3$, δ): 29.0, 33.6, 50.9, 55.9, 60.0, 107.0, 110.7, 125.7, 126.2, 126.7, 127.0, 128.7, 129.0, 134.2, 134.5, 137.7, 138.4, 140.9, 156.0, 158.4. MS (%): 330 (parent+1, 100). Anal. Calc'd. for C$_{22}$H$_{23}$N$_3$: C, 80.21, H, 7.04, N, 12.75. Found: C, 80.05, H, 7.11, N, 12.62.

EXAMPLE 7

(4-{2-[4-(6-Amino-pyridin-2-yl)-phenyl]-ethyl}-piperazin-1-yl)-furan-2-yl-methanone Prepared as in Example 1, using (2-furoyl)piperazine, in 51% yield, mp 152–154° C.

$^1$H-NMR (CDCl$_3$, δ): 2.55 (m, 2H), 2.65 (m, 2H), 2.82 (m, 2H), 3.81 (bs, 2H), 4.55 (bs, 2H), 6.44 (m, 2H), 6.96 (m, 1H), 7.02 (d, J=8, 1H), 7.23 (m, 2H), 7.45 (m, 2H), 7.83 (m, 2H). $^{13}$C-NMR (CDCl$_3$, δ): 33.2, 53.2 (broad), 60.0, 106.9, 110.6, 111.2, 126.9, 128.9, 137.7, 138.3, 140.6, 143.6, 148.0, 155.9, 158.3, 159.1. MS (%): 377 (parent+1, 100). Anal. Calc'd. for C$_{22}$H$_{24}$N$_4$O$_2$.3/4H$_2$O: C, 67.76, H, 6.59, N, 14.37. Found: C, 67.65, H, 6.25, N, 14.44.

EXAMPLE 8

6-{4-[2-(4-m-Tolyl-piperazin-1-yl)-ethyl]-phenyl}-pyridin-2-ylamine

Prepared as in Example 1, using (3-tolyl)piperazine, in 60% yield, mp 158–160° C.

$^1$H-NMR (CDCl$_3$, δ): 2.32 (s, 3H), 2.69 (m, 4H), 2.89 (m, 2H), 3.23 (m, 4H), 4.52 (bs, 2H), 6.43 (d, J=8, 1H), 6.6–6.8 (m, 3H), 7.07 (d, J=8, 1H), 7.16 (m, 1H), 7.29 (m, 2H), 7.48 (t, J=8, 1H), 7.86 (m, 2H). $^{13}$C-NMR (CDCl$_3$, δ): 21.8, 33.4, 49.2, 53.3, 60.3, 106.9, 110.7, 113.2, 116.9, 120.6, 126.9, 128.9, 137.7, 138.3, 138.8, 140.8, 151.4, 156.0, 158.2. MS (%): 373 (parent+1). Anal. Calc'd. for $C_{24}H_{28}N_4 \cdot 1/4H_2O$: C, 76.46, H, 7.62, N, 14.86. Found: C, 76.45, H, 7.43, N, 14.66.

EXAMPLE 9

6-(4-{2-[4-(3-Trifluoromethyl-phenyl)-piperazin-1-yl]-ethyl}-phenyl)-pyridin-2-ylamine Prepared as in Example 1, using (3-trifluoromethylphenyl)piperazine, in 62% yield, mp 189–191° C.

$^1$H-NMR (CDCl$_3$, δ): 2.68 (m, 4H), 2.88 (m, 2H), 3.26 (m, 4H), 4.51 (bs, 2H), 6.43 (d, J=8, 1H), 7.0–7.4 (m, 7H), 7.47 (t, J=8, 1H), 7.86 (m, 2H). $^{13}$C-NMR (CDCl$_3$, δ): 33.4, 48.7, 53.0, 60.2, 106.9, 110.7, 112.0, 112.1, 115.7, 115.8, 118.6, 122.5, 126.2, 126.9, 128.9, 129.5, 131.2, 131.6, 137.7, 138.3, 140.7, 151.4, 156.0, 158.2. MS (%): 427 (parent+1, 41). Anal. Calc'd. for $C_{24}H_{25}F_3N_4$: C, 67.59, H, 5.91, N, 13.14. Found: C, 67.30, H, 5.95, N, 13.28.

EXAMPLE 10

1-(4-{2-[4-(6-Amino-pyridin-2-yl)-phenyl]-ethyl}-piperazin-1-yl)-ethanone

Prepared as in Example 1, using N-acetylpiperazine, in 47% yield, mp 201–203° C.

$^1$H-NMR (CDCl$_3$, δ): 2.08 (s, 3H), 2.49 (m, 4H), 2.62 (m, 2H), 2.82 (m, 2H), 3.47 (m, 2H), 3.64 (m, 2H), 4.47 (bs, 2H), 6.43 (d, J=8, 1H), 7.05 (d, J=8, 1H), 7.1–7.2 (m, 2H), 7.47 (t, J=8, 1H), 7.84 (m, 2H). $^{13}$C-NMR (CDCl$_3$, δ): 21.3, 33.3, 41.4, 46.3, 52.7, 53.3, 60.1, 106.9, 110.7, 126.9, 128.9, 137.7, 138.3, 140.6, 156.0, 158.2, 168.9. MS (%): 325 (parent+1, 100). Anal. Calc'd. for $C_{19}H_{24}N_4O$: C, 70.34, H, 7.46, N, 17.27. Found: C, 70.21, H, 7.77, N, 17.10.

EXAMPLE 11

1-(4-{2-[4-(6-Amino-pyridin-2-yl)-phenyl]-ethyl}-1-piperazin-1-yl)-2-methoxy-ethanone Prepared as in Example 1, using 4-(2-methoxyacetyl)piperazine, in 53% yield, mp 148–150° C.

$^1$H-NMR (CDCl$_3$, δ): 2.49 (m, 4H), 2.61 (m, 2H), 2.83 (m, 2H), 3.40 (s, 3H), 3.48 (m, 2H), 3.65 (m, 2H), 4.08 (s, 2H), 4.53 (bs, 2H), 6.41 (d, J=8, 1H), 7.03 (d, J=7, 1H), 7.24 (m, 2H), 7.46 (t, J=8, 1H), 7.83 (m, 2H). $^{13}$C-NMR (CDCl$_3$, δ): 33.2, 41.8, 44.9, 52.8, 53.4, 59.0, 60.0, 71.8, 106.9, 110.7, 126.9, 128.9, 137.7, 138.3, 140.5, 155.9, 158.3, 167.4. MS (%): 355 (parent+1, 100). Anal. Calc'd. for $C_{20}H_{26}N_4O_2$: C, 67.77, H, 7.39, N, 15.81. Found: C, 67.80, H, 7.66, N, 15.79.

EXAMPLE 12

1-(4-{2-[4-(6-Amino-pyridin-2-yl)-phenyl]-ethyl}-piperazin-1-yl)-2-phenoxy-ethanone Prepared as in Example 1, using 4-(2-phenoxyacetyl)piperazine, in 57.5% yield, mp 127–130° C.

$^1$H-NMR (CDCl$_3$, δ): 2.49 (m, 4H), 2.60 (m, 2H), 2.81 (m, 2H), 3.59 (m, 2H), 3.65 (m, 2H), 4.51 (bs, 2H), 4.68 (s, 2H), 6.43 (d, J=8, 1H), 6.8–7.0 (m, 3H), 7.05 (d, J=8, 1H), 7.2–7.4 (m, 4H), 7.47 (t, J=8, 1H), 7.83 (m, 2H). $^{13}$C-NMR (CDCl$_3$, δ): 33.2, 42.1, 45.4, 52.7, 53.3, 60.0, 67.7, 106.9, 110.7, 114.6, 121.7, 126.9, 128.9, 129.6, 137.7, 138.3, 140.5, 155.9, 157.8, 158.2, 166.4. MS (%): 417 (parent+1, 100). Anal. Calc'd. for $C_{25}H_{28}N_4O_2 \cdot 1/4H_2O$: C, 71.32, H, 6.82, N, 13.31. Found: C, 71.55, H, 6.93, N, 13.25.

EXAMPLE 13

(4-{2-[4-(6-Amino-pyridin-2-yl)-phenyl]-ethyl}-piperazin-1-yl)-cyclopentyl-ethanone Prepared as in Example 1, using 4-(cyclopentanecarbonyl)piperazine, in 3.5% yield, mp 185–187° C.

$^1$H-NMR (CDCl$_3$, δ): 1.55 (m, 2H), 1.74 (m, 2H), 1.79 (m, 4H), 2.48 (m, 4H), 2.63 (m, 2H), 2.83 (m, 3H), 3.53 (m, 2H), 3.65 (m, 2H), 4.51 (bs, 2H), 6.42 (d, J=8, 1H), 7.03 (d, J=7, 1H), 7.25 (m, 2H), 7.46 (t, J=8, 1H), 7.83 (m, 2H). $^{13}$C-NMR (CDCl$_3$, δ): 26.0, 30.1, 33.3, 41.0, 41.8, 45.5, 52.9, 53.6, 60.1, 106.9, 110.7, 126.9, 128.9, 137.7, 138.3, 140.6, 156.0, 158.2, 174.5. MS (%): 379 (parent+1, 100). Anal. Calc'd. for $C_{23}H_{30}N_4O \cdot 3/4H_2O$: C, 70.47, H, 8.10, N, 14.29. Found: C, 70.40, H, 7.91, N, 14.02.

EXAMPLE 14

6-{4-[2-(5-Methyl-2,5-diaza-bicyclo[2.2.1]hept-2-yl)-ethyl]-phenyl}-pyridin-2-ylamine Prepared as in Example 1, using 5-methyl-2,5-diazabicyclo[3.3.1]heptane, in 29% yield, mp 132° C. (dec.) as the hydrochloride salt.

FAB MS (%): 309 (parent, 4), 279 (7), 167 (18), 149 (100), 113 (19). Anal. Calc'd. for $C_{19}H_{24}N_4 \cdot 3HCl$: C, 53.34, H, 6.83, N, 13.10. Found: C, 15 53.61, H, 6.94, N, 12.05.

EXAMPLE 15

6-(4-{2-[4-(4-Phenyl-thiazol-2-yl)-piperazin-1-yl]-ethyl}-phenyl)-pyridin-2-ylamine Prepared as in Example 1, using N-(4-phenyl-2-thiazolyl)piperazine, in 30% yield, mp 158–161° C.

$^1$H-NMR (CDCl$_3$, δ): 2.65 (m, 4H), 2.87 (m, 2H), 3.58 (m, 6H), 4.50 (bs, 2H), 6.42 (d, J=8, 1H), 6.76 (s, 1H), 7.04 (d, J=7, 1H), 7.2–7.4 (m, 5H), 7.47 (d, J=8, 1H), 7.85 (m, 4H). $^{13}$C-NMR (CDCl$_3$, δ): 33.3, 48.4, 52.4, 60.2, 101.5, 107.0, 110.7, 126.1, 126.9, 127.6, 128.5, 128.9, 129.3, 135.1, 137.6, 138.4, 140.6, 151.9, 155.9, 158.2, 160.9, 171.0. MS (%): 442 (parent+1, 100). Anal. Calc'd. for $C_{25}H_{27}N_5S \cdot 1/4H_2O$: C, 70.02, H, 6.21, N, 15.70. Found: C, 69.92, H, 6.18, N, 15.31.

EXAMPLE 16

2-(4-{2-[4-(6-Amino-pyridin-2-yl)-phenyl]-ethyl}-piperazin-1-yl)-1-phenyl-ethanone Prepared as in Example 1, using N-(benzoylmethyl)piperazine, in 66% yield, mp 225° C. (dec.) as the hydrochloride salt.

$^1$H-NMR (CDCl$_3$, δ): 2.8–3.2 (m, 10H), 3.56 (m, 2H), 3.88 (s, 2H), 6.48 (m, 1H), 6.99 (m, 1H), 7.2–7.6 (m, 6H), 7.82 (m, 2H), 7.93 (m, 2H). $^{13}$C-NMR (CDCl$_3$, δ): 31.6, 42.4, 51.7, 52.6, 54.1, 59.2, 63.6, 107.6, 110.6, 127.1, 128.0, 128.7, 129.0, 129.6, 133.5, 135.7, 137.2, 138.9, 139.1, 154.8, 158.1, 170.5. MS (%): 401 (parent+1, 100). Anal. Calc'd. for $C_{25}H_{28}N_4O \cdot 3HCl \cdot 3H_2O$: C, 53.24, H, 6.61, N, 9.93. Found: C, 53.39, H, 6.21, N, 10.06.

EXAMPLE 17

6-{4-[2-(4-Isobutyl-piperazin-1-yl)-ethyl]-phenyl}-pyridin-2-ylamine

Prepared as in Example 1, using N-isobutylpiperazine, in 44.5% yield, mp 85–88° C.

¹H-NMR (CDCl₃, δ): 0.88 (d, J=7, 6H), 1.77 (m, 1H), 2.11 (d, J=7, 2H), 2.5–2.7 (m, 10H), 2.83 (m, 2H), 4.49 (bs, 2H), 6.40 (d, J=8, 1H), 7.03 (d, J=7.5, 1H), 7.24 (m, 2H), 7.45 (t, J=8, 1H), 7.82 (m, 2H). ¹³C-NMR (CDCl₃, δ): 20.9, 25.3, 33.2, 53.0, 53.3, 60.2, 66.7, 106.9, 110.7, 126.9, 128.9, 137.65, 138.4, 140.7, 156.0, 158.3. MS (%): 339 (parent+1, 42). Anal. Calc'd. for C₂₁H₃₀N₄.1/2H₂O: C, 72.58, H, 8.99, N, 16.12. Found: C, 72.98, H, 9.12, N, 16.44.

EXAMPLE 18

6-{4-[2-(1,2,3,4-Tetrahydro-naphthalen-2-ylamino)-ethyl]-phenyl}-pyridin-2-ylamine Prepared as in Example 1, using 2-aminotetralin, in 18% yield, mp 320–322° C. as the hydrochloride salt.

¹H-NMR (CD₃OD, δ) hydrochloride salt: 1.8–2.0 (m, 2H), 2.4–2.5 (m, 4H), 2.9–3.0 (m, 2H), 3.1–3.2 (m, 3H), 6;.99 (d, J=8, 1H), 7.1–7.2 (m, 5H), 7.59 (m, 2H), 7.83 (m, 2H), 7.9–8.0 (m, 1H). ¹³C-NMR (CDCl₃, δ): 15.5, 27.2, 28.4, 33.2, 56.2, 66.9, 112.0, 112.9, 127.5, 127.9, 128.8, 129.8, 130.3, 131.2, 133.0, 136.0, 141.7, 145.9. MS (%): 344 (parent+1, 100). Anal. Calc'd. for C₂₃H₂₅N₃.2HCl.1/2H₂O: C, 64.94, H, 6.63, N, 9.88. Found: C, 64.87, H, 6.83, N, 9.86.

EXAMPLE 19

6-(Dibenzylamino)ethyl)phenyl)-pyridin-2-ylamine

Prepared as in Example 1, using dibenzylamine, in 14% yield, mp 206–208° C. as the hydrochloride salt.

¹H-NMR (CD₃OD, δ) hydrochloride salt: 2.91 (t, J=7, 2H), 3.80 (t, J=7, 2H), 4.24 (bs, 4H), 6.97 (d, J=8, 1H), 7.15 (d, J=7, 1H), 7.4–7.5 (m, 12H), 7.74 (m, 2H), 7.97 (dd, J=7,8, 1H). ¹³C-NMR (CDC₃, δ): 39.9, 52.1, 63.6, 111.8, 112.5, 128.2, 130.3, 130.7, 130.9, 131.1, 131.3, 132.4, 144.8, 145.9, 148.5, 156.7. MS (%): 309 (4), 215 (25), 198 (100), 155 (22), 135 (13), 119 (47), 103 (21). Anal. Calc'd. for C₂₇H₂₇N₃.3HCl: C, 64.48, H, 6.01, N, 8.36. Found: C, 64.84, H, 6.31, N, 9.07.

EXAMPLE 20

6-{4-[2-(8-Aza-spiro[4.5]dec-8-yl)-ethyl]-phenyl}-pyridin-2-ylamine

Prepared as in Example 1, using 8-Aza-spiro[4.5]decane, in 63% yield, mp 130–132° C.

¹H-NMR (CDCl₃, δ): 1.3–1.7 (m, 12H), 2.47 (bs, 4H), 2.59 (m, 2H), 2.86 (m, 2H), 4.49 (bs, 2H), 6.42 (d, J=8, 1H), 7.04 (d, J=7.5, 1H), 7.2–7.3 (m, 2H), 7.46 (t, J=8, 1H), 7.83 (m, 2H). ¹³C-NMR (CDCl₃, δ): 24.3, 33.5, 37.5, 38.0, 40.7, 51.5, 60.8, 106.8, 110.7, 126.8, 128.9, 137.6, 138.3, 141.1, 156.1, 158.2. MS (%): 336 (parent+1, 79). Anal. Calc'd. for C₂₂H₂₉N₃.1/4H₂O: C, 77.72, H, 8.75, N, 12.36. Found: C, 77.74, H, 8.74, N, 12.41.

EXAMPLE 21

6-{4-[2-(4-Dimethylamino-piperidin-1-yl)-ethyl]-phenyl}-pyridin-2-ylamine

Prepared as in Example 1, using 4-(N,N-dimethylamino)piperidine, in 60% yield, mp 174–176° C.

¹H-NMR (CDCl₃, δ): 1.5–1.6 (m, 2H), 1.8 (m, 2H), 2.0 (m, 2H), 2.29 (s, 6H), 2.60 (m, 2H), 2.80 (m, 2H), 3.15 (m, 2H), 3.4–3.5 (m, 1H), 4.51 (bs, 2H, NH), 6.41 (d, J=8, 1H), 7.04 (d, J=7, 1H), 7.24 (m, 2H), 7.46 (t, J=8, 1H), 7.82 (m, 2H). ¹³C-NMR (CDCl₃, δ): 28.1, 33.6, 41.5, 53.1, 60.4, 62.3, 106.9, 110.7, 126.8, 128.9, 137.6, 138.3, 141.0, 156.1, 158.2. MS (%): 325 (parent+1, 100), 280 (45), 197 (65). Anal. Calc'd. for C₂₃H₂₅N₃.1/2H₂O: C, 72.03, H, 8.77, N, 16.80. Found: C, 72.09, H, 8.57, N, 16.86.

EXAMPLE 22

6-{4-[2-(1,3-Dihydro-isoindol-2-yl)-ethyl]-phenyl}-pyridin-2-ylamine

Prepared as in Example 1, using dihydroisoindole, in 19% yield, mp 140–143° C.

¹H-NMR (CDCl₃, δ): 2.97 (m, 4H), 4.00 (bs, 4H), 4.51 (bs, 2H), NH), 6.42 (d, J=8, 1H), 7.06 (d, J=8, 1H), 7.20 (m, 4H), 7.32 (m, 2H), 7.47 (t, J=8, 1H), 7.86 (m, 2H). ¹³C-NMR (CDCl₃, δ): 35.5, 57.8, 59.2, 106.9, 110.8, 122.3, 126.7, 126.9, 128.9, 137.7, 138.3, 139.9, 140.8, 156.1, 158.2. MS (%): 316 (parent+1, 92), 197 (43), 132 (100). Anal. Calc'd. for C₂₁H₂₁N₃.1/2H₂O: C, 77.75, H, 6.84, N, 12.95. Found: C, 78.03, H, 6.78, N, 12.58.

EXAMPLE 23

2-(4-{2-[4-(6-Amino-pyridin-2-yl)-phenyl]-ethyl}-piperazin-1-yl)-N-isopropyl-acetamide Prepared as in Example 1, using 4-(N-isopropylacetamido)piperazine, in 78% yield, mp 163–165° C.

¹H-NMR (CDCl₃, δ): 1.14 (d, J=6, 6H), 2.55 (m, 8H), 2.6 (m, 2H), 2.75 (m, 2H), 2.96 (s, 2H), 4.07 (hp, J=6, 1H), 4.52 (bs, 2H, NH), 6.42 (d, J=8, 1H), 6.92 (m, 1H), 7.03 (d, J=7, 1H), 7.24 (m, 2H), 7.46 (t, J=8, 1H), 7.82 (m, 2H). ¹³C-NMR (CDCl₃, δ): 22.8, 33.4, 40.7, 53.2, 53.4, 60.2, 61.6, 106.9, 110.7, 126.9, 128.9, 137.7, 138.3, 140.7, 156.0, 158.2, 169.1. MS (%): 382 (parent+1, 100), 198 (75). Anal. Calc'd. for C₂₂H₃₁N₅O: C, 69.26, H, 8.19, N, 18.36. Found: C, 68.97, H, 8.36, N, 18.58.

EXAMPLE 24

(4-{2-[4-(6-Amino-pyridin-2-yl-)-phenyl]-ethyl}-piperazin-1-yl)-acetic acid ethyl ester Prepared as in Example 1, using 4-(N-carboethoxymethyl)piperazine, in 16% yield, as a low-melting sold.

¹H-NMR (CDCl₃, δ): 1.26 (t, J=7, 3H), 2.5–2.7 (m, 10H), 2.83 (m, 2H), 3.20 (s, 2H), 4.17 (q, J=7, 2H), 4.49 (bs, 2H), 6.41 (d, J=8, 1H), 7.04 (d, J=7, 1H), 7.25 (m, 2H), 7.46 (t, J=7, 1H), 7.82 (m, 2H). ¹³C-NMR (CDCl₃, δ): 14.25, 33.3, 52.9, 53.0, 59.6, 60.2, 60.6, 106.9, 110.7, 126.8, 128.9, 137.6, 138.3, 140.8, 156.0, 158.2, 170.3. IR (cm.⁻¹, KBr): 1740 (C=O). MS (%): 369 (parent+1, 100), 197 (35), 185 (70), 119 (38). HRMS (%): 369.23070 (parent+1, 100, calculated 369.22905).

EXAMPLE 25

(4-{2-[4-(6-Amino-pyridin-2-yl)-phenyl]-ethyl}-piperazin-1-yl)-phenyl-methanone

Prepared as in Example 1, using (N-benzoyl)piperazine, in 43% yield, mp 125–127° C.

¹H-NMR (CDCl₃, δ): 2.4 (m, 2H), 2.5–2.7 (m, 4H), 2.85 (m, 2H), 3.5 (m, 2H), 3.8 (m, 2H), 4.53 (bs, 2H), NH), 6.41 (d, J=8, 1H), 7.03 (d, J=7, 1H), 7.24 (m, 2H), 7.38 (m, 5H), 7.45 (t, J=8, 1H), 7.83 (m, 2H). ¹³C-NMR (CDCl₃, δ): 33.2, 60.1, 106.9, 110.7, 126.9, 127.1, 128.5, 128.9, 129.7, 135.8, 137.7, 138.3, 140.5, 155.9, 158.3, 170.3. MS (%): 387 (parent+1, 92), 203 (35), 105 (100). Anal. Calc'd. for $C_{24}H_{26}N_4O.1/4H_2O$: C, 73.72, H, 6.83, N, 14.33. Found: C, 73.96, H, 6.88, N, 14.39.

EXAMPLE 26

6-{4-[2-(3-Phenyl-pyrrolidin-1-yl)-ethyl]-phenyl}-pyridin-2-ylamine

Prepared as in Example 1, using 3-phenylpyrrolidine, in 54% yield, mp 100° C. (dec.) as the hydrochloride salt.

$^1$H-NMR as the hydrochloride salt (MeOD, δ): 2.2–2.6 (m, 2H), 3.2–3.4 (m, 5H), 3.5–3.7 (m, 2H), 3.7–4.0 (m, 2H), 6.99 (d, J=8, 1H), 7.17 (d, J=7, 1H), 7.3–7.5 (m, 5H), 7.59 (m, 2H), 7.83 (m, 2H), 7.97 (t, J=8, 1H). $^{13}$C-NMR (CDCl$_3$, δ): (the aliphatic and some of the aromatic carbons are doubled, possibly due to restricted rotation) 31.9, 32.7, 32.8, 34.2, 55.0, 56.5, 56.9, 57.5, 60.6, 60.9, 111.9, 112.9, 128.4, 128.6, 128.7, 128.9, 130.0, 131.2, 131.9, 139.8, 140.8, 141.6, 145.9, 147.8, 156.8. MS (%): 344 (parent+1, 100), 197 (26), 160 (40). Anal. Calc'd. for $C_{23}H_{25}N_3.2HCl.5/4H_2O$: C, 62.94, H, 6.77, N, 9.57. Found: C, 62.90, H, 6.93, N, 9.46.

EXAMPLE 27

6-(4-{2-[4-(1-Phenyl-1H-tetrazol-5-yl)-piperazin-1-yl]-ethyl}-phenyl)-pyridin-2-ylamine Prepared as in Example 1, using 4-(N-phenyltetrazol-5-yl)piperazine, in 50% yield, mp 212–214° C.

$^1$H-NMR (CDCl$_3$, δ): 2.55 (m, 4H), 2.64 (m, 2H), 2.80 (m, 2H), 3.28 (m, 4H), 4.52 (bs, 2H, N$\underline{H}$), 6.42 (d, J=8, 1H), 7.04 (d, J=7, 1H), 7.23 (m, 2H), 7.4–7.6 (m, 6H), 7.81 (m, 2H). $^{13}$C-NMR (CDCl$_3$, δ): 33.2, 48.7, 52.1, 60.0, 107.0, 110.7, 123.7, 123.8, 126.9, 128.9, 129.7, 129.9, 130.1, 135.0, 137.7, 138.4, 140.5, 155.9, 157.5, 158.2, 160.8. MS (%): 427 (parent+1, 100), 197 (85). Anal. Calc'd. for $C_{24}H_{26}N_8.1/2H_2O$: C, 66.19, H, 6.25, N, 25.73. Found: C, 66.03, H, 6.24, N, 25.88.

EXAMPLE 28

2-{2-[4-(6-Amino-pyridin-2-yl)-phenyl]-ethyl}-1,2,3,4-tetrahydro-isoquinoline-3-carboxylic Acid Prepared as in Example 1, using 3-carboxy(1,2,3,4-tetrahydroisoquinoline), in 17% yield, mp 110° C. (dec.) as the hydrochloride salt.

$^1$H-NMR (CDCl$_3$, δ): 2.9–3.1 (m, 6H), 3.7 (m, 1H), 4.4 (m, 2H), 4.54 (bs, 2H, N$\underline{H}$), 6.43 (d, J=8, 1H), 7.0–7.2 (m, 4H), 7.05 (d, J=7, 1H), 7.28 (m, 2H), 7.47 (t, J=8, 1H), 7.86 (m, 2H). $^{13}$C-NMR (CDCl$_3$, δ): 31.6, 34.8, 47.2, 55.9, 65.3, 107.0, 110.7, 126.1, 126.2, 127.0, 129.1, 133.1, 134.8, 138.1, 138.2, 138.4, 155.8, 158.3, 173.1. MS (%): 374 (parent+1, 81), 197 (100). Anal. Calc'd. for $C_{23}H_{23}N_3O_2.HCl.1/4H_2O$: C, 60.13, H, 6.47, N, 9.15. Found: C, 60.54, H, 6.07, N, 8.78.

EXAMPLE 29

4-{2-[4-(6-Amino-pyridin-2-yl)-phenyl]-ethyl}-piperazine-1-carboxylic Acid (4-chloro-phenyl)-amide Prepared as in Example 4, using 4-chlorophenylisocyanate, in 75.5% yield, mp 160–162° C.

$^1$H-NMR (CDCl$_3$, δ): 2.49 (m, 4H), 2.60 (m, 2H), 2.80 (m, 2H), 3.47 (m, 4H), 4.69 (bs, 2H, N$\underline{H}$), 6.40 (d, J=8, 1H), 6.96 (d, J=7, 1H), 7.1–7.4 (m, 6H), 7.44 (t, J=8, 1H), 7.73 (m, 2H). $^{13}$C-NMR (CDCl$_3$, δ): 33.0, 43.7, 52.7, 60.0, 107.3, 110.9, 121.4, 121.5, 127.0, 127.9, 128.7, 128.9, 137.7, 137.8, 138.6, 140.4, 155.3, 155.9, 158.4. MS (%): 436 (parent+1, 24), 283 (27), 155 950), 119 (100). Anal. Calc'd. for $C_{24}H_{26}N_5OCl$: C, 66.12, H, 6.01, N, 16.06. Found: C, 65.92, H, 6.21, N, 16.18.

EXAMPLE 30

4-{2-[4-(6-Amino-pyridin-2-yl)-phenyl]-ethyl}-piperazine-1-carboxylic Acid p-tolyl-amide Prepared as in Example 4, using 4-methylphenylisocyanate, in 79% yield, mp 160–162° C.

$^1$H-NMR (CDCl$_3$, δ): 2.28 (s, 3H), 2.52 (m, 4H), 2.64 (m, 2H), 2.82 (m, 2H), 3.49 (m, 4H), 4.52 (bs, 2H, N$\underline{H}$), 6.42 (d, J=8, 1H), 6.44 (m, 1H), 7.0–7.1 and 7.2–7.4 (m, 6H), 7.47 (d, J=8, 1H), 7.84 (m, 2H). $^{13}$C-NMR (CDCl$_3$, δ): 20.8, 33.25, 44.1, 52.8, 60.1, 107.0, 110.7, 120.3, 126.9, 128.9, 129.4, 136.4, 137.7, 138.4, 140.6, 155.2, 155.9, 158.2. MS (%): 416 (parent+1, 71), 283 (100), 2332 (73), 197 (70), 119 (53), 99 (66). Anal. Calc'd. for $C_{25}H_{29}N_5O$: C, 72.26, H, 7.03, N, 16.85. Found: C, 72.07, H, 7.13, N, 16.99.

EXAMPLE 31

4-{2-[4-(6-Amino-pyridin-2-yl)-phenyl]-ethyl}-piperazine-1-carboxylic Acid (4-methoxy-phenyl)-amide Prepared as in Example 4, using 4-methoxyphenylisocyanate, in 80% yield, mp 182–184° C.

$^1$H-NMR (CDCl$_3$, δ): 2.53 (m, 4H), 2.66 (m, 2H), 2.83 (m, 2H), 3.49 (m, 4H), 3.75 (s, 3H), 4.57 (bs, 2H, N$\underline{H}$), 6.42 (d, J=8, 1H), 6.80 (m, 2H), 7.02 (d, J=7, 1H), 7.1–7.3 (m, 4H), 7.47 (t, J=8, 1H), 7.80 (m, 2H). $^{13}$C-NMR (CDCl$_3$, δ): 33.1, 44.0, 52.7, 52.8, 60.1, 107.1, 110.8, 114.1, 122.4, 122.6, 126.9, 128.9, 131.9, 137.7, 138.5, 140.5, 155.7, 155.9, 158.3. MS (%): 432 (parent+1, 15.5), 283 (20), 155 (50), 119 (100), 103 (47). Anal. Calc'd. for $C_{25}H_{29}N_5O_2.1/4H_2O$: C, 68.86, H, 6.82, N, 16.06. Found: C, 68.80, H, 6.80, N, 16.20.

EXAMPLE 32

4-{2-[4-(6-Amino-pyridin-2-yl)-phenyl]-ethyl}-piperazine-1-carboxylic Acid Cyclohexylamide Prepared as in Example 4, using cyclohexylisocyanate, in 79% yield, mp 180–182° C.

$^1$H-NMR (CDCl$_3$, δ): 1.1 (m, 3H), 1.3 (m, 2H), 1.8 (m, 3H), 2.0 (m, 2H), 2.48 (m, 4H), 2.63 (m, 2H), 2.82 (m, 2H), 3.36 (m, 4H), 3.63 (m, 1H), 4.30 (d, J=5, 1H, N$\underline{H}$), 4.54 (bs, 2H, N$\underline{H}$), 6.41 (d, J=8, 1H), 7.03 (d, J=8, 1H), 7.25 (m, 2H), 7.46 (t, J=8, 1H), 7.82 (m, 2H). $^{13}$C-NMR (CDCl$_3$, δ): 25.1, 25.7, 33.3, 34.0, 43.7, 49.4, 52.8, 60.2, 106.9, 110.7, 126.9, 137.6, 138.4, 140.6, 155.9, 157.0, 158.2. MS (%): 408 (parent+1, 55), 283 (100), 224 (50), 197 (60), 119 (44). Anal. Calc'd. for $C_{24}H_{33}N_5O.1/4H_2O$: C, 69.96, H, 8.19, N, 17.00. Found: C, 70.13, H, 8.32, N, 17.19.

EXAMPLE 33

4-{2-[4-(6-Amino-pyridin-2-yl)-phenyl]-ethyl}-piperazine-1-carboxylic Acid phenyl Ester Prepared as in Example 4, using phenyl chloroformate, in 19% yield, mp 102–104° C.

¹H-NMR (CDCl₃, δ): 2.57 (m, 4H), 2.69 (m, 2H), 2.83 (m, 2H), 3.6–3.8 (m, 4H), 4.52 (bs, 2H, N$\underline{H}$), 6.42 (d, J=8, 1H), 7.1–7.4 (m, 7H), 7.48 (t, J=8, 1H), 7.85 (m, 2H). ¹³C-NMR (CDCl₃, δ): 33.3, 44.0, 44.5, 52.5, 53.0, 60.2, 107.0, 110.7, 121.7, 125.3, 127.0, 128.9, 129.3, 137.7, 138.4, 140.6, 151.4, 153.7, 155.95, 158.2. MS (%): 403 (parent+1, 100), 219 (90), 197 (77). Anal. Calc'd. for C₂₄H₂₆N₄O₂: C, 71.62, H, 6.51, N, 13.92. Found: C, 71.23, H, 6.55, N, 14.01.

EXAMPLE 34

6-(4-{2-[4-(1-Phenyl-1H-imidazol-2-yl)-piperazin-1-yl]-ethyl}-phenyl)-pyridin-2-ylamine Prepared as in Example 1, using (N-phenylimidazol-2-yl) piperazine, in 63% yield, mp 140–142° C.

¹H-NMR (CDCl₃, δ): 2.49 (m, 4H), 2.60 (m, 2H), 2.76 (m, 2H), 3.07 (m, 4H), 4.55 (bs, 2H, N$\underline{H}$), 6.39 (d, J=8, 1H), 6.84 (s, 2H), 7.01 (d, J=7, 1H), 7.22 (m, 2H), 7.3–7.6 (m, 6H), 7.80 (m, 2H). ¹³C-NMR (CDCl₃, δ): 33.3, 49.6, 52.7, 60.6, 106.9, 110.6, 118.3, 123.8, 125.4, 126.8, 127.2, 128.9, 129.4, 137.6, 138.3, 140.75, 151.3, 156.0, 158.3. MS (%): 425 (parent+1, 100), 241 (33), 197 (40), 184 (32), 172 (55), 160 (38). Anal. Calc'd. for C₂₆H₂₈N₆.1/4H₂O: C, 72.79, H, 6.70, N, 19.59. Found: C, 72.63, H, 6.56, N, 19.66.

EXAMPLE 35

6-[4-(2-Phenethylamino-ethyl)-phenyl]-pyridin-2-ylamine

Prepared as in Example 1, using benzylamine, in 38% yield, mp 212–215° C. as the hydrochloride salt.

¹H-NMR (CD₃OD, δ) hydrochloride salt: 3.04 (m, 2H), 3.14 (m, 2H), 3.30 (m, 4H), 6.99 (d, J=8, 1H), 7.17 (d, J=7, 1H), 7.2–7.4 (m, 5H), 7.55 (m, 2H), 7.83 (m, 2H), 7.97 (m, 1H). ¹³C-NMR (CDCl₃, δ): 33.0, 33.4, 111.9, 112.9, 128.3, 128.9, 129.8, 130.0, 131.1, 132.0, 137.8, 141.7, 145.9, 147.9, 156.8. MS (%): 318.3009 (parent+1, 100, calculated 318.19702). Anal. Calc'd. for C₂₁H₂₃N₃.2HCl.H₂O: C, 61.77, H, 6.66, N, 10.29. Found: C, 61.49, H, 6.67, N, 10.35.

EXAMPLE 36

1-(3-{2-[4-(6-Amino-pyridin-2-yl)-phenyl]-ethyl}-3-aza-bicyclo[3.1.0]hex-6-yl)-3-phenyl-urea Prepared from the final compound in Example 2, using phenylisocyanate, in 67% yield, mp 192–194° C.

¹H-NMR (CDCl₃, δ): 1.59 (m, 2H), 2.52 (m, 2H), 2.65 (m, 2H), 2.78 (m, 2H), 3.30 (m, 2H), 3.34 (m, 1H), 6.50 (d, J=8, 1H), 6.97 (m, 2H), 7.2–7.4 (m, 6H), 7.48 (t, J=8, 1H), 7.74 (m, 2H). ¹³C-NMR (CDCl₃, δ): 25.8, 31.8, 35.9, 55.9, 58.5, 108.5, 111.2, 120.4, 123.6, 128.0, 129.8, 129.9, 139,1, 139.7, 140.7, 142.1, 157.2, 158.9, 160.9. MS (%): 414 (parent+1, 100), 226 (40), 149 (81), 127 (63). Anal. Calc'd. for C₂₅H₂₇N₅O: C, 72.61, H, 6.58, N, 16.94. Found: C, 72.34, H, 6.24, N, 17.00.

EXAMPLE 37

(3-{2-[4-(6-Amino-pyridin-2-yl)-phenyl]-ethyl}-3-aza-bicyclo[3.1.0]hex-6-yl)-dimethyl-amine Prepared from the final compound in Example 2, using formaldehyde in formic acid at 80° C. for 2.5 hr, in 56.5% yield, as an amorphous solid.

¹H-NMR (CDCl₃, δ): 1.47 (m, 2H), 1.89 (m, 1H), 2.31 (s, 6H), 2.41 (m, 2H), 2.66 (m, 2H), 2.74 (m, 2H), 3.08 (m, 2H), 4.52 (bs, 2H, N$\underline{H}$), 6.42 (d, J=8, 1H), 7.05 (d, J=7, 2H), 7.24 (m, 2H), 7.47 (t, J=8, 1H), 7.83 (m, 2H). ¹³C-NMR (CDCl₃, δ): 24.8, 35.3, 45.1, 48.3, 55.0, 57.4, 106.8, 110.7, 459.7, 128.8, 137.5, 138.3, 141.1, 156.1, 158.2. MS (%): 323 (parent+1, 7), 167 (35), 149 (100), 113 (37). Anal. Calc'd. for C₂₀H₂₆N₄. 3HCl.H₂O: C, 53.40, H, 6.45, N, 12.45. Found: C, 53.44, H, 7.03, N, 12.32.

EXAMPLE 38

N-(3-{2-[4-(6-Amino-pyridin-2-yl)-phenyl]-ethyl}-3-aza-bicyclo[3.1.0]hex-6-yl)-2-(4-fluoro-phenyl)-acetamide Prepared from the final compound in Example 2, using 4-fluorophenylacetic acid coupling mediated by N-ethyl, N-(3-dimethylaminopropyl)carbodiimide, in 38% yield, mp 161–163° C.

¹H-NMR (CDCl₃, δ): 1.42 (m, 2H), 2.36 (m, 2H), 2.63 (m, 2H), 2.70 (m, 2H), 2.88 (m, 1H), 3.15 (m, 2H), 3.45 (s, 2H), 4.51 (bs, 2H, N$\underline{H}$), 5.49 (bs, 1H, N$\underline{H}$), 6.42 (d, J=8, 1H), 7.0–7.3 (m, 7H), 7.46 (t, J=8, 1H), 7.80 (m, 2H). ¹³C-NMR (CDCl₃, δ): 24.3, 30.5, 35.1, 42.8, 54.4, 56.7, 106.9, 110.7, 115.6, 115.9, 126.7, 128.8, 130.8, 130.9, 137.4, 138.3, 141.0, 156.0, 158.2, 160.4, 163.7, 171.5. MS (%): 431 (parent+1, 100), 226 (33), 197 (60), 109 (60). Anal. Calc'd. for C₂₆H₂₇FN₄O.1/2H₂O: C, 71.05, H, 6.42, N, 12.75. Found: C, 71.14, H, 6.53, N, 12.60.

EXAMPLE 39

6-(4-{2-[4-(3-Phenyl-allyl)-piperazin-1-yl]-ethyl}-phenyl)-pyridin-2-ylamine

Prepared as in Example 1, using (3-phenyl-allyl)-piperazine, in 67% yield, mp 249–255° C. (hydrochloride salt).

¹H-NMR as the hydrochloride salt (CDCl₃/MeOD, δ): 3.27 (m, 2H), 3.56 (m, 2H), 3.7–4.0 (m, 8H), 4.08 (d, J=7, 2H), 6.34 (m, 2H), 6.95 (m, 2H), 7.11 (d, J=7, 1H), 7.33 (m, 2H), 7.51 (m, 3H), 7.79 (m, 2H), 7.93 (dd, J=7,8, 1H). ¹³C-NMR (CDCl₃, δ): 27.1, 31.1, 57.0, 58.1, 59.9, 112.0, 113.2, 116.5, 128.4, 1218.5, 128.8, 129.0, 131.9, 136.4, 141.0, 143.2, 145.8, 147.8, 150.3, 156.8. MS (%): 399 (parent+1, 54), 149 (77), 119 (93), 117 (100). Anal. Calc'd. for C₂₆H₃₀N₄.3HCl.1/2H₂O: C, 60.41, H, 6.63, N, 10.84. Found: C, 60.79, H, 6.65, N, 10.67.

EXAMPLE 40

6-(4-{2-[4-(3-Phenyl-propyl)-piperazin-1-yl]-ethyl}-phenyl)-pyridin-2-ylamine

Prepared as in Example 1, using (3-phenyl-propyl)-piperazine, in 64% yield, mp 258–264° C. (hydrochloride salt).

¹H-NMR (CDCl₃, δ): 1.83 (qn, J=8, 2H), 2.54 (m, 2H), 2.6–2.8 (m, 12H), 2.83 (m, 2H), 4.47 (bs, 2H, N$\underline{H}$), 6.42 (d, J=8, 1H), 7.05 (d, J=7, 1H), 7.1–7.3 (m, 7H), 7.46 (t, J=8, 1H), 7.82 (m, 2H). ¹³C-NMR (CDCl₃, δ): 28.6, 33.3, 33.7, 53.2, 58,0, 60.3, 65.8, 106.8, 110.7, 125.8, 126.8, 128.3, 128.4, 128.9, 137.6, 138.3, 140.9, 142.1, 156.1, 158.2. MS (%): 401 (parent+1, 10), 167 (21), 149 (100), 113 (24). Anal. Calc'd. for C₂₆H₃₂N₄.3HCl.5/2H₂O: C, 56.27, H, 7.26, N, 10.10. Found: C, 56.35, H, 7.47, N, 9.72.

EXAMPLE 41

4-{2-[4-(6-Amino-pyridin-2-yl)-phenyl]-ethyl}-piperazine-1-carboxylic Acid (3,4-dimethyl-phenyl)-amide Prepared as in Example 4, using 3,4-dimethylphenylisocyanate, in 90% yield, mp 122–125° C.

¹H-NMR (CDCl₃, δ): 2.15 (s, 3H), 2.18 (s, 3H), 2.47 (m, 4H), 2.65 (m, 2H), 2.85 (m, 2H), 3.55 (m, 4H), 4.55 (bs, 2H, NH), 6.35 (s, 1H), 6.42 (d, J=8, 1H), 7.0–7.3 (m, 5H), 7.47 (t, J=8, 1H), 7.82 (m, 2H). ¹³C-NMR (CDCl₃, δ): 19.0, 19.9, 33.2, 44.1, 52.8, 60.1, 104.0, 110.7, 117.7, 121.7, 126.9, 128.9, 129., 131.4, 136.6, 137.0, 137.6, 138.4, 140.6, 155.2, 155.9, 158.2. MS (%): 430 (parent+1, 41), 283 (100), 246 (58), 197 (81), 99 (76). Anal. Calc'd. for $C_{26}H_{31}N_5O$: C, 72.70, H, 7.27, N, 16.30. Found: C, 72.51, H, 7.33, N, 16.06.

EXAMPLE 42

1-(4-{2-[4-(6-Amino-pyridin-2-yl)-phenyl]-ethyl}-piperazin-1-yl)-2-(4-chloro-phenyl)-ethanone Prepared as in Example 5, using 4-chlorophenylacetic acid, in 38% yield, mp 205° C. (dec., hydrochloride salt).

¹H-NMR (CDCl₃, δ): 2.37 (m, 2H), 2.49 (m, 2H), 2.59 (m, 2H), 2.62 (m, 2H), 3.45 (m, 2H), 3.6 (m, 2H), 3.67 (s, 2H), 4.86 (bs, 2H, NH), 6.42 (d, J=8, 1H) 7.01 (d, J=7, 1H), 7.1–7.3 (m, 6H), 7.47 (dd, J=7,8, 1H), 7.79 (m, 2H). ¹³C-NMR (CDCl₃, δ): 33.1, 40.0, 41.7, 45.9, 52.6, 53.0, 59.8, 107.2, 110.7, 127.0, 128.5, 128.8, 130.0, 130.8, 122.7, 133.5, 137.3, 138.6, 140.5, 155.6, 158,2, 169.0. MS (%): 435 (parent+1, 100), 251 (49), 197 (61), 119 (62). Anal. Calc'd. for $C_{25}H_{27}N_4ClO.1/4H_2O$: C, 68.33, H, 6.31, N, 12.75. Found: C, 68.59, H, 6.13, N, 12.53.

EXAMPLE 43

8-{2-[4-(6-Amino-pyridin-2-yl)-phenyl]-ethyl}-3-benzyl-1,3,8-triaza-spiro[4.5]decane-2,4-dione Prepared as in Example 1, using 3-benzyl-1,3,8-triaza-spiro[4.5]decane-2,4-dione (prepared as described in WO 95/12577 (1995)), in 42% yield, mp 190° C. (dec., as the hydrochloride salt).

¹H-NMR (CDCl₃, δ): 1.62 (m, 2H), 2.11 (m, 2H), 2.23 (m, 2H), 2.63 (m, 2H), 2.82 (m, 2H), 2.95 (m, 2H), 4.50 (bs, 2H, NH), 4.63 (s, 2H), 6.41 (d, J=8, 1H), 7.04 (d, J=7, 1H), 7.2–7.4 (m, 7H), 7.46 (dd, J=7,8, 1H), 7.83 (m, 2H). ¹³C-NMR (CDCl₃, δ): 33.2, 33.4, 42.1, 49.0, 60.1, 60.2, 106.9, 110.7, 126.9, 127.8, 128.3, 128.7, 128.9, 136.1, 167.7, 138.4, 140.7, 155.9, 156.8, 158.2, 176.0. MS (%): 456 (parent+1, 100), 272 (81), 197 (79), 119 (35). Anal. Calc'd. for $C_{27}H_{29}N_5O_2.1/2H_2O$ (analyzed as the free base): C, 69.81, H, 6.51, N, 15.07. Found: C, 69.94, H, 6.52, N, 15.00.

EXAMPLE 44

3-{2-[4-(6-Amino-pyridin-2-yl)-phenyl]-ethyl}-3-aza-bicyclo[3.2.1]oct-8-ylamine

Prepared as in Example 2, using 3-aza-bicyclo[3.2.1]oct-8-ylamine t-butylcarbamate followed by removral of the t-butylcarbamate group, in 83% yield, mp 235° C. (dec., as the hydrochlorides salt).

¹H-NMR (CDCl₃, δ): 1.69 (m, 4H), 1.82 (m, 2H), 2.59 (m, 6H), 2.75 (m, 2H), 2.97 (m, 1H), 4.53 (bs, 2H, NH), 6.39 (d, J=8, 1H), 7.03 (d, J=7, 1H), 7.24 (m, 2H), 7.43 (dd, J=7,8, 1H), 7.82 (m, 2H). ¹³C-NMR (CDCl₃, δ): 26.9, 33.2, 39.2, 52.1, 54.1, 59.7, 106.8, 110.65, 126.6, 128.9, 139.3, 138.3, 141.6, 156.1, 158.2. MS (%): 323 (parent+1, 10), 167 (24), 149 (100), 113 (27). Anal. Calc'd. for $C_{20}H_{26}N_4.HCl.7/4H_2O.CH_2Cl_2$: C, 53.06, H, 6.89, N, 11.79. Found: C, 53.35, H, 7.07, N, 11.79.

EXAMPLE 45

4-{2-[4-(6-Amino-pyridin-2-yl)-phenyl]-ethyl}-piperazine-1-carboxylic Acid m-tolyl-amide Prepared as in Example 3, using 3-tolylisocyanate, in 85% yield, mp 88–94° C.

¹H-NMR (CDCl₃, δ): 2.30 (s, 3H), 2.52 (m, 4H), 2.64 (m, 2H), 2.83 (m, 2H), 3.50 (m, 4H), 4.54 (bs, 2H, NH), 6.42 (d, J=8, 1H), 6.48 (s, 1H), 6.83 (d, J=7, 1H), 7.04 (d, J=7, 1H), 7.1–7.3 (m, 4H), 7.47 (t, J=8, 1H), 7.83 (m, 2H). ¹³C-NMR (CDCl₃, δ): 21.5, 33.2, 44.1, 52.8, 60.1, 107.0, 110.7, 117.1, 120.8, 123.9, 126.9, 128.7, 128.9, 137.7, 138.4, 138.7, 138.9, 140.6, 155.1, 155.9, 158.2. MS (%): 416 (parent+1, 33), 283 (100), 232 (60), 197 (95). Anal. Calc'd. for $C_{25}H_{29}N_5O$: C, 72.26, H, 7.03, N, 16.85. Found: C, 72.08, H, 7.08, N, 16.74.

EXAMPLE 46

(3-{2-[4-(6-Amino-pyridin-2-yl)-phenyl]-ethyl}-3-aza-bicyclo[3.1.0]hex-6-yl)-phenethyl-amine Prepared using the final product of Example 2, by reaction with phenylacetaldehyde and sodium cyanoborohydride in methanol, in 41% yield, mp 165° C. (dec., as the hydrochloride salt). ¹H-NMR (CDCl₃, δ): 1.43 (m, 2H), 2.4 (m, 3H), 2.6 (m, 2H), 2.8 (m, 4H), 2.92 (m, 2H), 3.09 (m, 2H), 4.51 (bs, 2H, NH), 6.41 (d, J=8, 1H), 7.04 (d, J=7, 1H), 7.1–7.3 (m, 7H), 7.43 (t, J=8, 1H), 7.82 (m, 2H). ¹³C-NMR (CDCl₃, δ): 24.4, 35.0, 36.1, 39.0, 50.6, 55.0, 57.3, 106.9, 110.7, 126.1, 126.8, 128.5, 128.7, 128.9, 137.6, 138.35, 140.0, 140.7, 156.0, 158.2. HRMS (%): Calc'd. for $C_{26}H_{30}N_4$: 399.2549. Found: 399.2534.

EXAMPLE 47

4-{2-[4-(6-Amino-pyridin-2-yl)-phenyl]-ethyl}-piperazine-1-carboxylic Acid Benzylamide Prepared as in Example 3, using benzylisocyanate, in 60% yield, mp 172–175° C.

¹H-NMR (MeOD, CDCl₃, δ): 2.48 (m, 4H), 2.63 (m, 2H), 2.80 (m, 2H), 3.39 (m, 4H), 4.37 (s, 2H), 4.61 (bs for NH₂, partly exchanged), 5.03 (m, NH, partly exchanged), 6.41 (d, J=8, 1H), 6.99 (d, J=7, 1H), 7.1–7.3 (m, 7H), 7.45 (t, J=8, 1H), 7.76 (m, 2H). ¹³C-NMR (CDCl₃, δ): 33.1, 43.6, 44.8, 52.8, 60.1, 107.1, 110.8, 126.9, 127.3, 127.7, 128.6, 128.9, 137.7, 138.5, 139.3, 140.5, 155.9, 157.7, 158.3. MS (%): 416 (parent+1, 10), 283 (100), 232 (56), 197 (80), 99 (70). Anal. Calc'd. for $C_{25}H_{29}N_5O.1/4H_2O$: C, 71.49, H, 7.28, N, 16.67. Found: C, 71.45, H, 7.06, N, 16.67.

EXAMPLE 48

6-[4-(2-{4-[1-(4-Fluoro-phenyl)-1H-tetrazol-5-yl]-piperazin-1-yl}-ethyl)-phenyl]-pyridin-2-ylamine Prepared as in Example 1, using [(4-fluoro-phenyl)-1H-tetrazol-5-yl]piperazine, in 20% yield, mp 185–187° C.

¹H-NMR (CDCl₃, δ): 2.58 (m, 4H), 2.67 (m, 2H), 2.81 (m, 2H), 3.28 (m, 4H), 4.51 (bs, 2H, NH), 6.45 (d, J=8,1H), 7.06 (d, J=7, 1H), 7.2–7.3 (m, 4H), 7.49 (t, J=8, 1H), 7.60 (m, 2H), 7.85 (m, 2H). ¹³C-NMR (CDCl₃, δ): 33.2, 48.7, 52.1, 60.0, 106.9, 110.7, 116.8, 117.1, 125.8, 125.9, 126.9, 128.9, 131.0, 137.7, 138.4, 140.4, 155.9, 157.6, 158.2, 161.1, 164.5. MS (%): 445 (parent+1, 85), 197 (80), 119 (100), 103 (84). Anal. Calc'd. for $C_{24}H_{25}N_8F$: C, 64.85, H, 5.67, N, 25.21. Found: C, 64.63, H, 5.75, N, 25.36.

EXAMPLE 49

6-(4-{2-[4-cis-(4-Phenyl-cyclohexyl)-piperazin-1-yl]-ethyl}-phenyl)-pyridin-2-ylamine Prepared as in Example 1, using cis-(4-phenyl-cyclohexyl)-piperazine, in 46% yield, mp 127–130° C.

¹H-NMR (CDCl₃, δ): 1.58 (m, 4H), 1.95 (m, 4H), 2.27 (m, 1H), 2.6–2.8 (m, 10H), 2.83 (m, 2H), 4.50 (bs, 2H, NH), 6.42 (d, J=8, 1H), 7.06 (d, J=7, 1H), 7.2–7.3 (m, 7H), 7.47 (t, J=8, 1H), 7.85 (m, 2H). ¹³C-NMR (CDCl₃, δ): 28.0, 28.4, 33.4, 42.8, 49.8, 53.8, 59.1, 60.5, 106.9, 110.7, 125.7, 126.8, 127.1, 128.2, 128.9, 129.2, 137.6, 138.3, 141.0, 147.1, 156.1, 158.2. MS (%): 441 (parent+1, 59), 257 (75), 197 (40), 91 (100). Anal. Calc'd. for C₂₉H₃₆N₄O.1/4H₂O: C, 78.25, H, 8.27, N, 12.59. Found: C, 78.30, H, 8.22, N, 12.70.

EXAMPLE 50

6-(4-{2-[4-trans-(4-Phenyl-cyclohexyl)-piperazin-1-yl]-ethyl}-phenyl)-pyridin-2-ylamine Prepared as in Example 1, using trans-(4-phenyl-cyclohexyl)-piperazine, in 54% yield, mp 178–180° C.

¹H-NMR (CDCl₃, δ): 1.49 (m, 4H), 2.03 (m, 4H), 2.47 (m, 2H), 2.65 (m, 8H), 2.85 (m, 2H), 4.50 (bs, 2H, NH), 6.42 (d, J=8, 1H), 7.05 (d, J=7, 1H), 7.1–7.2 (m, 7H), 7.47 (t, J=8, 1H), 7.84 (m, 2H). ¹³C-NMR (CDCl₃, δ): 28.9, 33.3, 33.5, 44.1, 49.1, 53.5, 60.4, 63.3, 106.9, 110.7, 126.0, 126.8, 126.9, 128.3, 128.9, 137.6, 138.3, 140.9, 146.9, 156.0, 158.2. MS (%): 441 (parent+1, 39), 257 (90), 197 (40), 91 (100). Anal. Calc'd. for C₂₉H₃₆N₄O.1/4H₂O: C, 78.25, H, 8.27, N, 12.59. Found: C, 77.98, H, 8.25, N, 12.60.

EXAMPLE 51

(3-{2-[4-(6-Amino-pyridin-2-yl)-phenyl]-ethyl}-3-aza-bicyclo[3.1.0]hex-6-yl)-(3-phenyl-propyl)-amine Hydrochloride Salt Prepared from the final compound in Example 2, using 3-phenylpropionaldehyde via reductive amination using sodium cyanoborohydride in methanol, in 27% yield, mp 160–163° C. as the hydrochloride salt from 1,2-dichloroethane.

¹H-NMR (CDCl₃, δ): 1.44 (m, 2H), 1.83 (qn, 2H), 2.43 (m, 3H), 2.6–2.8 (m, 8H), 3.09 (m, 2H), 4.54 (bs, 2H, NH), 6.43 (d, J=8, 1H), 7.07 (d, J=7, 1H), 7.1–7.3 (m, 7H), 7.48 (t, J=8, 1H), 7.85 (m, 2H). ¹³C-NMR (CDCl₃, δ): 24.4, 31.5, 33.6, 35.2, 39.0, 49.1, 55.0, 57.3, 106.8, 110.7, 125.8, 126.7, 128.3, 128.4, 128.9, 137.5, 138.3, 141.0, 142.1, 156.1, 158.2. MS (%): 413 (parent+1, 70), 226 (73), 197 (66), 91 (100). Anal. Calc'd. for C₂₇H₃₂N₄.2HCl.2H₂O.1/2C₂H₄Cl₂: C, 58.90, H, 7.06, N, 9.81. Found: C, 59.19, H, 7.18, N, 9.46.

EXAMPLE 52

2-(3-{2-[4-(6-Amino-pyridin-2-yl)-phenyl]-ethyl}-3-aza-bicyclo[3.1.0]hex-6-ylamino)-acetamide Prepared from the final compound in Example 2, using iodoacetamide, in 39.5% yield, mp 140° C. (dec.).

¹H-NMR (CDCl₃, δ): 1.51 (m, 2H), 2.41 (m, 1H), 2.50 (m, 2H), 2.65 (m, 2H), 2.75 (m, 2H), 3.05 (m, 2H), 3.25 (s, 2H), 6.49 (d, J=8, 1H), 6.96 (d, J=7, 1H), 7.24 (m, 2H), 7.48 (dd, J=7,8, 1H), 7.74 (m, 2H). ¹³C-NMR (CDCl₃, δ): 25.3, 35.7, 40.6, 56.1, 58.6, 60.1, 108.5, 111.1, 128.0, 129.8, 139.2, 139.7, 141.9, 157.1, 161.0, 177.0. HRMS (%): 352 (parent+1, 43), 155 (47), 119 (100), 103 (54).

EXAMPLE 53

6-[4-(2-{4-[2-(4-Fluoro-phenyl)-ethyl]-piperazin-1-yl}-ethyl)-phenyl]-pyridin-2-ylamine Prepared as in Example 1, using (4-fluoro)phenethyl-piperazine, in 35% yield, mp 165–167° C.

¹H-NMR (CDCl₃, δ): 2.5–2.7 (m, 12H), 2.7–2.9 (m, 4H), 4.51 (bs, 2H, NH), 6.42 (d, J=8, 1H), 6.95 (m, 2H), 7.05 (d, J=8, 1H), 7.14 (m, 2H), 7.25 (m, 2H), 7.47 (t, J=8, 1H), 7.83 (m, 2H). ¹³C-NMR (CDCl₃, δ): 32.8, 33.3, 53.1, 60.3, 60.5, 106.9, 110.7, 115.0, 115.3, 126.8, 128.9, 130.0, 130.1, 135.9, 136.0, 137.6, 138.3, 140.9, 156.1, 158,2, 159.8, 163.0. MS (%): 405 (parent+1, 92), 221 (100), 197 (53), 123 (75). Anal. Calc'd. for C₂₅H₂₉FN₄.1/4H₂O: C, 72.61, H, 7.31, N, 13.55. Found: C, 72.74, H, 7.05, N, 13.22.

EXAMPLE 54

6-(4-{2-[4-(1-Methyl-2-phenyl-ethyl)-piperazin-1-yl]-ethyl}-phenyl)-pyridin-2-ylamine Prepared as in Example 1, using 1-methyl-2-phenyl-ethyl-piperazine, in 30% yield, mp 252–256° C. as the hydrochloride salt.

¹H-NMR (CDCl₃, δ): 0.95 (d, J=6, 3H), 2.41 (m, 1H), 2.5–2.7 (m, 10H), 2.83 (m, 3H), 3.04 (m, 1H), 4.54 (bs, 2H, NH), 6.41 (d, J=8, 1H), 7.04 (d, J=7, 1H), 7.1–7.3 (m, 7H), 7.46 (t, J=8, 1), 7.84 (m, 2H). ¹³C-NMR (CDCl₃, δ): 14.4, 33.4, 39.3, 48.3, 53.6, 60.4, 61.3, 106.9, 110.7, 125.8, 126.9, 127.0, 128.2, 128.9, 129.3, 137.6, 138.3, 140.6, 140.9, 156.1, 158.3. MS (%): 401 (parent+1, 64), 309 (35), 217 (40), 197 (34), 91 (100). Anal. Calc'd. for C₂₈H₃₂N₄.3HCl.H₂O: C, 59.15, H, 7.06, N, 10.61. Found: C, 59.07, H, 7.22, N, 10.46.

EXAMPLE 55

6-(4-{2-[4-(1,2,3,4-Tetrahydro-naphthalen-2-yl)-piperazin-1-yl]-ethyl}-phenyl)-pyridin-2-ylamine Prepared as in Example 1 using 4-(1,2,3,4-tetrahydro-naphthalen-2-yl)-piperazine, in 33% yield, mp>220° C. as the hydrochloride salt.

¹H-NMR (CDCl₃, δ): 1.65 (m, 1H), 2.15 (m, 1H), 2.6–3.0 (m, 17H), 4.52 (bs, 2H, NH), 6.41 (d, J=8, 1H), 7.09 (m, 5H), 7.26 (m, 2H), 7.46 (t, J=8, 1H), 7.84 (m, 2H). ¹³C-NMR (CDCl₃, δ): 26.1, 29.4, 32.0, 33.3, 49.1, 53.5, 60.3, 60.4, 106.9, 110.7, 125.7, 125.8, 126.9, 128.5, 128.9, 129.5, 135.9, 136.4, 137.6, 138.3, 140.9, 156.1, 158.2. MS (%): 413 (parent+1, 30), 229 (65), 197 (30), 131 (100). Anal. Calc'd. for C₂₇H₃₂N₄.3HCl: C, 62.13, H, 6.76, N, 10.73. Found: C, 62.44, H, 7.11, N, 10.49.

EXAMPLE 56

N-(1-{2-[4-(6-Amino-pyridin-2-yl)-phenyl]-ethyl}-pyrrolidin-3-yl)-2-(4-fluoro-phenyl)-acetamide Prepared from (1-{2-[4-(6-amino-pyridin-2-yl)-phenyl]-ethyl}-pyrrolidin-3-yl)-2-amine, using 4-fluorophenylacetic acid coupling mediated by N-ethyl, N-(3-dimethylaminopropyl)carbodiimide, in 55% yield, mp 90° C. (dec.).

¹H-NMR (CDCl₃, δ): 1.54 (m, 2H), 2.24 (m, 3H), 2.53 (m, 1H), 2.72 (m, 2H), 2.79 (m, 2H), 2.98 (m, 1H), 4.5 (m, 2H), 6.19 (m, 1H), 6.40 (d, J=8, 1H), 7.02 (m, 3H), 7.20 (m, 4H), 7.46 (t, J=8, 1H), 7.82 (m, 2H). ¹³C-NMR (CDCl₃, δ): 32.1, 34.6, 42.7, 48.6, 52.8, 57.2, 60.6, 107.0, 110.7, 115.5, 115.7, 126.9, 128.8, 131.8, 130.9, 137.8, 138.4, 140.2, 155.8, 158.3, 160.8, 163.2, 170.2. MS (%): 419 (parent+1, 43), 391 (38), 167 (40), 149 (100), 119 (46), 113 (73). HRMS: Calc'd. for C₂₅H₂₈N₄OF: 419.2247. Found: 419.2266.

EXAMPLE 57

8-{2-[4-(6-Amino-pyridin-2-yl)-phenyl]-ethyl}-3-phenethyl-1,3,8-triaza-spiro[4.5]decane-2,4-dione Prepared as in Example 1, using 3-phenethyl-1,3,8-triaza-spiro[4.5]decane-2,4-dione, in 45% yield, mp 176–180° C. as the hydrochloride salt.

¹H-NMR (CDCl₃, δ): 1.51 (m, 2H), 2.02 (m, 2H), 2.23 (m, 2H), 2.63 (m, 2H), 2.82 (m, 2H), 2.92 (m, 4H), 3.73 (t, J=7, 2H), 4.54 (bs, 2H, NH), 6.42 (d, J=8, 1H), 7.05 (m, 2H), 7.2–7.3 (m, 5H), 7.47 (t, J=8, 1H), 7.83 (m, 2H). ¹³C-NMR (CDCl₃, δ): 33.2, 33.3, 33.8, 39.5, 49.0, 59.7, 60.1, 106.9, 110.7, 126.6, 126.9, 128.5, 128.9, 129.0, 137.7, 138.4, 140.7, 156.0, 156.8, 158.3, 176.1. MS (%): 470 (parent+1, 70), 360 (67), 340 (100), 338 (75), 332 (55). Anal. Calc'd. for $C_{28}H_{31}N_5O_2 \cdot 1/2H_2O$: C, 70.27, H, 6.74, N, 14.63. Found: C, 70.16, H, 6.65, N, 14.85.

EXAMPLE 58

8-{2-[4-(6-Amino-pyridin-2-yl)-phenyl]-ethyl}-8-aza-bicyclo[3.2.1]oct-3-ylamine

Prepared as in Example 1, using 8-aza-bicyclo[3.2.1]oct-3-ylamine as the t-butyl carbamate, followed by deprotection using trifluoroacetic acid, in 67% yield, mp>300° C. as the hydrochloride salt.

¹H-NMR (CDCl₃, δ): 1.45 (m, 4H), 1.54 (m, 2H), 1.68 (m, 2H), 1.91 (m, 2H), 2.63 (m, 2H), 2.78 (m, 2H), 2.93 (m, 1H), 3.29 (m, 2H), 4.50 (bs, 2H, NH), 6.39 (d, J=8, 1H), 7.03 (d, J=7, 1H), 7.24 (m, 2H), 7.45 (t, J=8, 1H), 7.81 (m, 2H). ¹³C-NMR (CDCl₃, δ): 26.9, 35.6, 41.2, 43.0, 53.3, 58.8, 106.8, 110.7, 126.7, 128.9, 137.5, 138.3, 141.1, 156.0, 158.2. MS (%): 323 (parent+1, 23), 197 (25), 149 (36), 109 (57), 95 (100). Anal. Calc'd. for $C_{20}H_{26}N_4 \cdot HCl \cdot 3/2H_2O \cdot CH_2Cl_2$: C, 53.57, H, 6.85, N, 11.90. Found: C, 53.90, H, 7.09, N, 12.14.

EXAMPLE 59

4-Amino-1{-2-[4-(6-amino-pyridin-2-yl)-phenyl]-ethyl}-piperidine-4-carboxylic Acid benzylamide Prepared as in Example 1, using 4-amino-piperidine-4-carboxylic acid benzylamide, mp>240° C. (dec.) as the hydrochloride salt.

¹H-NMR (CDCl₃, δ): 1.47 (m, 2H), 2.36 (m, 4H), 2.64 (m, 2H), 2.87 (m, 2H), 2.92 (m, 2H), 4.42 (d, J=6, 2H), 4.47 (s, 2H), 6.42 (d, J=8, 1H), 7.05 (d, J=7, 1H), 7.2–7.4 (m, 7H), 7.47 (t, J=8, 1H), 7.83 (m, 2H), 8.02 (bs, 1H, NH). ¹³C-NMR (CDCl₃, δ): 33.11, 34.8, 43.2, 48.9, 55.1, 60.3, 107.1, 110.9, 126.9, 127.3, 127.6, 128.6, 128.9, 137.7, 138.5, 140.5, 156.0, 158.3, 177.0. MS (%): 430 (parent+1, 100), 197 (47), 133 962). Anal. Calc'd. for $C_{28}H_{31}N_5O \cdot HCl \cdot 5/4H_2O \cdot CH_2Cl_2$: C, 56.55, H, 6.42, N, 12.21. Found: C, 56.88, H, 6.84, N, 12.09.

EXAMPLE 60

6-(4-{2-[4-(2-Amino-ethyl)-piperazin-1-yl]-ethyl}-phenyl)-pyridin-2-ylamine

Prepared as in Example 1, using (2-amino-ethyl)-piperazine as the t-butylcarbamate, followed by deprotection using trifluoroacetic acid in methylene chloride, in 90% yield, as a hygroscopic solid as the trifluoroacetate salt.

¹H-NMR (CDCl₃, δ): 1.93 (m, 2H), 2.3–2.5 (m, 14H), 2.81 (m, 2H), 4.50 (bs, 2H, NH), 6.40 (d, J=8, 1H), 7.03 (d, J=7, 1H), 7.23 (m, 2H), 7.45 (t, J=8, 1H), 7.81 (m, 2H). ¹³C-NMR (CDCl₃, δ): 33.3, 53.2, 60.4, 106.9, 110.7, 126.8, 128.9, 137.6, 138.3, 140.9, 156.0, 158.2. MS (%): 326 (parent+1, 8), 167 (25), 149 (100), 133 (45), 119 (28), 113 (25). HRMS. Calc'd. for $C_{19}H_{27}N_5$: 326.2345. Found: 326.2340.

EXAMPLE 61

2-Amino-1-(4-{2-[4-(6-amino-pyridin-2-yl)-phenyl]-ethyl}-piperazin-1-yl)-3-phenyl-propan-1-one Prepared from the title compound in Example 3B, using t-BOC henylalanine coupling mediated by N-ethyl, N-(3-dimethylaminopropyl)carbodiimide, in 68% yield, followed by deprotection using trifluoroacetic acid in methylene chloride in 78% yield, mp 230° C. (dec.) as the hydrochloride salt from ethyl ether.

¹H-NMR (CDCl₃, δ): 1.89 (m, 1H), 2.31 (m, 2H), 2.50 (m, 3H), 2.74 (m, 3H), 2.90 (m, 1H), 3.10 (m, 1H), 3.31 (m, 1H), 3.5–3.7 (m, 2H), 3.94 (m, 1H), 4.59 (bs, 2H, NH), 6.39 (d, J=8, 1H), 7.02 (d, J=7, 1H), 7.1–7.3 (m, 7H), 7.44 (t, J=8, 1H), 7.82 (m, 2H). ¹³C-NMR (CDCl₃, δ): 33.1, 41.9, 45.2, 52.5, 52.8, 59.9, 107.0, 110.6, 126.9, 128.6, 128.8, 129.4, 137.6, 137.7, 138.3, 140.5, 155.8, 158.3, 173.0. MS (%): 430 (parent+1, 23), 167 (26), 149 (100), 133 (72), 113 (25). HRMS: Calc'd. for $C_{26}H_{31}N_5O \cdot 3HCl \cdot 5/4H_2O$: C, 56.19, H, 6.99, N, 11.70. Found: C, 56.55, H, 6.73, N, 11.32.

EXAMPLE 62

{2-[4-(6-Amino-pyridin-2-yl)-phenyl]-ethyl}-(8-benzyl-8-aza-bicyclo[3.2.1]oct-3-yl)-amine Prepared as in Example 1, using (8-benzyl-8-aza-bicyclo[3.2.1]oct-3-yl)-amine, mp 260° C. (dec.) as the hydrochloride salt.

¹H-NMR (CDCl₃, δ): 1.45 (m, 3H), 1.53 (m, 2H), 1.72 (m, 2H), 1.97 (m, 2H), 2.7–2.9 (m, 4H), 3.18 (m, 2H), 3.54 (s, 2H), 4.49 (bs, 2H, NH), 6.41 (d, J=8, 1H), 7.04 (d, J=7, 1H), 7.2–7.4 (m, 7H), 7.46 (t, J=8, 1H), 7.83 (m, 2H). ¹³C-NMR (CDCl₃, δ): 27.0, 36.5, 38.3, 48.1, 48.9, 55.5, 58.5, 106.9, 110.8, 126.6, 126.9, 128.1, 128.5, 128.9, 137.7, 138.3, 140.3, 140.7, 156.0, 158.2. MS (%): 413 (parent+1, 6), 200 (40), 133 (28), 91 (100). Anal. Calc'd. for $C_{27}H_{32}N_4 \cdot 3HCl \cdot H_2O$: C, 60.06, H, 6.91, N, 10.38. Found: C, 60.33, H, 6.82, N, 10.39.

EXAMPLE 63

1-{2-[4-(6-Amino-pyridin-2-yl)-phenyl]-ethyl}-piperidin-4-yl}-3-phenyl-urea

Prepared as in Example 1, using 4-(phenylureido)-piperidine, mp>280° C. as the hydrochloride salt.

¹H-NMR (CDCl₃, δ): 1.41 (m, 2H), 1.93 (m, 2H), 2.17 (m, 2H), 2.585 (m, 2H), 2.79 (m, 2H), 2.92 (m, 2H), 3.60 (m, 1H), 6.39 (d, J=8, 1H), 6.92 (m, 2H), 7.2–7.4 (m, 7H), 7.42 (t, J=8, 1H), 7.69 (m, 2H). ¹³C-NMR (CDCl₃, MeOD, δ): 31.9, 32.8, 46.2, 52.4, 60.1, 107.3, 110.9, 119.0, 122.4, 127.0, 128.8, 137.8, 138.6, 139.3, 140.0, 155.6, 155.9, 158.5. MS (%): 416 (parent+1, 78),323 (52), 232 (50), 197 (100), 133 (82), 119 (79), 103 (69). Anal. Calc'd. for $C_{25}H_{29}N_5O \cdot 2HCl \cdot 1/2H_2O \cdot 3/4CH_2Cl_2$: C, 55.11, H, 6.02, N, 12.48. Found: C, 55.34, H, 6.05, N, 12.14.

EXAMPLE 64

1-(1-{2-[4-(6-Amino-pyridin-2-yl)-phenyl]-ethyl}-piperidin-4-yl)-3-benzyl-urea

Prepared as in Example 1, using 4-(benzylureido)-piperidine, in 24% yield, mp 120° C. (dec.) as the hydrochloride salt.

¹H-NMR (CDCl₃, δ): 1.42 (m, 2H), 1.93 (m, 2H), 2.16 (m, 2H), 2.58 (m, 2H), 2.7–2.9 (m, 4H), 3.60 (m, 1H), 4.32 (d, J=5, 2H), 4.48 (bs, 2H, NH), 4.90 (m, 1H), 6.41 (d, J=8, 1H), 7.03 (d,J=7, 1H), 7.1–7.3 (m, 7H), 7.46 (t, J=8, 1H), 7.81 (m, 2H). ¹³C-NMR (CDCl₃, δ): 32.7, 33.4, 44.5, 47.1, 52.3, 60.2, 106.9, 110.8, 126.9, 127.3, 127.5, 128.6, 128.9, 137.7, 138.6, 139.2, 140.6, 156.0, 157.5, 158.2. MS (%): 430 (parent+1, 10), 155 (50), 135 (28), 119 (100), 103 (55).

Anal. Calc'd. for $C_{26}H_{31}N_5O \cdot 2HCl \cdot H_2O$: C, 60.00, H, 6.78, N, 13.45. Found: C, 60.23, H, 6.57, N, 13.29.

EXAMPLE 65

N-(1-{2-[4-(6-Amino-pyridin-2-yl)-phenyl]-ethyl}-pigeridin-4-yl)-2-(4-fluoro-phenyl)-acetamide Prepared as in Example 1, using 4-((4-fluorophenyl)acetamido)-piperidine, in 35% yield, mp 170° C. (dec.) as the hydrochloride salt.

$^1$H-NMR (CDCl$_3$, δ): 1.37 (m, 2H), 1.88 (m, 2H), 2.14 (m, 2H), 2.59 (m, 2H), 2.77 (m, 2H), 2.83 (m, 2H), 3.50 as, 2H), 3.79 (m, 1H), 4.46 (bs, 2H, NH), 5.23 (d, J=7, 1H), 6.42 (d, J=8, 1H), 7.02 (m, 3H), 7.2–7.3 (m, 5H), 7.46 (dd, J=7,8, 1H), 7.81 (m, 2H). $^{13}$C-NMR (CDCl$_3$, δ): 32.0, 33.5, 43.0, 46.5, 52.2, 60.2, 106.9, 110.7, 115.7, 115.95, 126.8, 128.9, 130.8, 130.9, 137.6, 138.3, 140.7, 156.0, 158.2, 170.0. MS (%): 433 (parent+1, 70), 155 (48), 119 (100), 103 (61). Anal. Calc'd. for $C_{26}H_{29}N_4OF \cdot 2HCl \cdot 3/4H_2O$: C, 60.17, H, 6.31, N, 10.80. Found: C, 60.56, H, 6.24, N, 10.75.

EXAMPLE 66

{2-[4-(6-Amino-pyridin-2-yl)-phenyl]-ethyl}-(8-aza-bicyclo[3.2.1]oct-3-yl)-amine Prepared as in Example 1, using N-benzyl-(8-aza-bicyclo [3.2.1]oct-3-yl)-amine followed by debenzylation using ammonium formate and 10% palladium-on-carbon in ethanol, in 71% yield, mp 170° C. (dec.) as the hydrochloride salt.

$^1$H-NMR (CDCl$_3$, δ): 1.24 (m, 2H), 1.58 (m, 2H), 1.7–1.9 (m, 4H), 2.7–2.9 (m, 4H), 3.54 (m, 2H), 4.10 (m, 1H), 4.49 (bs, 2H, NH), 6.41 (d, J=8, 1H), 7.04 (d, J=7, 1H), 7.2–7.3 (m, 2H), 7.46 (m, 1H), 7.82 (m, 2H). $^{13}$C-NMR (CDCl$_3$, δ): 29.1, 36.4, 40.7, 47.9, 19.0, 54.2, 106.9, 110.8, 126.9, 128.9, 137.7, 138.4, 140.5, 156.0, 158.2. MS (%): 323 (parent+1, 66), 199 (55), 133 (8 1), 110 (100). Anal. Calc'd. for $C_{20}H_{26}N_4 \cdot 2HCl \cdot 2H_2O \cdot 1/4CH_2Cl_2$: C, 53.73, H, 7.24, N, 12.38. Found: C, 53.48, H, 7.23, N, 12.04.

EXAMPLE 67

6-{4-[2-(4-Amino-piperidin-1-yl)-ethyl]-phenyl}-pyridin-2-ylamine

Prepared as in Example 1, using 4-(t-butoxycarbonylamino)-piperidine followed by deblocking with trifluoroacetic acid in methylene chloride at room temperature, in 100% yield, mp 190–195° C. as the trifluoroacetate) salt.

$^1$H-NMR (TFA salt, CDCl$_3$, δ): 1.99 (m, 2H), 2.28 (m, 2H), 3.17 (m, 4H), 3.41 (m, 2H), 3.50 (m, 1H), 3.78 (m, 2H), 6.96 (d, J=8, 1H), 7.14 (d, J=7, 1H), 7.52 (m, 2H), 7.78 (m, 2H), 7.95 (dd, J=7,8, 1H). $^{13}$C-NMR (CDCl$_3$, δ): 28.5, 31.1, 46.7, 46.8, 51.9, 112.0, 112.9, 128.9, 131.1, 132.3, 141.3, 145.8, 148.1, 156.8. MS (%): 297 (parent+1, 100), 197 (50), 133 (52). Anal. Calc'd. for $C_{18}H_{24}N_4 \cdot 3(C_2HF_3O_2) \cdot H_2O$: C, 43.91, H, 4.45, N, 8.53. Found: C, 43.82, H, 4.11, N, 8.48.

EXAMPLE 68

4-Amino-1-{2-[4-(6-amino-pyridin-2-yl)-phenyl]-ethyl}-piperidine-4-carboxylic Acid Morpholine-amide Prepared as in Example 1, using 4-amino-piperidine-4-carboxylic acid morpholine-amide, in 13% yield, mp>280° C. as the hydrochloride salt.

$^1$H-NMR (CDCl$_3$, δ): 2.2–2.4 (m, 4H), 2.57 (m, 2H), 2.79 (m, 2H), 2.8–2.9 (m, 4H), 3.5–37 (m, 8H), 4.48 (bs, 2H), 6.41 (d, J=8, 1H), 7.04 (d, J=7, 1H), 7.24 (m, 2H), 7.46 (t, J=8, 1H), 7.81 (m, 2H). $^{13}$C-NMR (CDCl$_3$, δ): 33.4, 34.0, 37.0, 56.4, 49.9, 60.3, 61.3, 67.1, 106.9, 110.7, 126.8, 128.9, 137.0, 138.3, 156.0, 158.2 (carbonyl carbon not visible in this scan). MS (%): 410 (parent+1, 12), 242 (100) not— Anal. Calc'd. for $C_{25}H_{29}N_5O \cdot 2HCl \cdot 1/2H_2O \cdot 3/4CH_2Cl_2$: C, 55.11, H, 6.02, N, 12.48. Found: C, 55.34, H, 6.05, N, 12.14.

EXAMPLE 69

4-Amino-1-{2-[4-(6-amino-pyridin-2-yl-phenyl]-ethyl}-piperidine-4-carboxylic Acid pyrrolidine-amide Prepared as in Example 1, using 4-amino-piperidine-4-carboxylic acid pyrrolidine-amide, in 39% yield, mp 220° C. (dec.) as the hydrochloride salt.

$^1$H-NMR (CDCl$_3$, δ): 1.8 (bs, 6H), 2.51 (m, 4H), 2.59 (m, 2H), 2.79 (m, 2H), 3.4–3.6 (m, 4H), 3.8 (bs, 4H), 4.51 (bs, 2H), 6.39 (d, J=8, 1H), 7.02 (d, J=7, 1H), 7.22 (m, 2H), 7.46 (t, J=8, 1H), 7.80 (m, 2H). $^{13}$C-NMR (CDCl$_3$, δ): 33.4, 35.6, 45.4, 48.0, 59.8, 56.1, 60.4, 106.9, 110.7, 126.8, 128.9, 137.6, 138.3, 141.0, 156.0, 158.2, 173.8. FAB MS (%): 394 (parent+1, 28), 197 (38), 149 (63), 133 (100). Anal. Calc'd. for $C_{23}H_{31}N_5O \cdot HCl \cdot 1/4H_2O \cdot CH_2Cl_2$: C, 55.50, H, 6.64, N, 13.48. Found: C, 55.79, H, 6.85, N, 13.10.

EXAMPLE 70

6-{4-[2-(3-Amino-pyrrolidin-1-yl)-ethyl]-phenyl}-pyridin-2-ylamine

Prepared as in Example 1, using 3-(t-butoxycarbonylamino)-pyrrolidine followed by deprotection using trifluoroacetic acid in methylene chloride at room temperature, in 92% yield, mp 135° C. (dec.) as the hydrochloride salt.

$^1$H-NMR (CDCl$_3$, δ): 1.4–1.5 (m, 3H), 2.16 (m, 1H), 2.37 (m, 1H), 2.52 (m, 1H), 2.7–2.9 (m, 6H), 3.51 (m, 1H), 4.53 (bs, 2H, NH), 6.42 (d, J=8, 1H), 7.05 (d, J=7, 1H), 7.27 (m, 2H), 7.47 (t, J=8, 1H), 7.84 (m, 2H). $^{13}$C-NMR (CDCl$_3$, δ): 35.2, 35.3, 51.0, 53.3, 58.0, 64.1, 106.8, 110.7, 126.8, 128.8, 137.6, 138.3, 141.0, 156.1, 158.2. MS (%): 283 (parent+1, 100), 197 (37), 99 (75). Anal. Calc'd. for $C_{17}H_{22}N_4 \cdot 3HCl \cdot H_2O$: C, 49.83, H, 6.64, N, 13.67. Found: C, 49.94, H, 6.89, N, 13.29.

EXAMPLE 71

1-(3-{2-[4-(6-Amino-pyridin-2-yl)-phenyl]-ethylamino}-8-aza-bicyclo[3.2.1]oct-8-yl)-2-(4-fluoro-phenyl)-ethanone Prepared as in Example 1, using 1-amino-8-aza-bicyclo [3.2.11oct-8-yl)-2-(4-fluoro-phenyl)-ethanone, in 23.5% yield, mp 170° C. (dec.) as the hydrochloride salt.

$^1$H-NMR (CDCl$_3$, δ): 1.12 (m, 1H), 1.39 (m, 1H), 1.61 (m, 2H), 1.84 (m, 4H), 2.79 (m, 4H), 2.97 (m, 1H), 3.56 (dd, J=15,35, 2H), 4.165 (m, 1H), 4.49 (bs, 2H, NH), 4.68 (m, 1H), 6.42 (d, J=8, 1H), 6.96 (m, 2H), 7.04 (d, J=8, 1H), 7.1–7.3 (m, 4H), 7.47 (t, J=8, 1H), 7.83 (m, 2H). $^{13}$C-NMR (CDCl$_3$, δ): 27.2, 28.9, 36.3. 38.3. 39.9, 40.4, 47.9, 48.9, 51.1, 54.4, 107.0, 110.8, 115.3, 115.5, 127.0, 128.9, 130.3, 131.0, 137.9, 138.4, 140.2, 155.9, 158.2, 162.9, 1613.2. MS (%): 459 (parent+1, 27), 133 (98), 110 (100), 109 (30). Anal. Calc'd. for $C_{28}H_{31}N_4OF \cdot 2HCl \cdot 3/4H_2O$: C, 61.70, H, 6.38, N, 10.28. Found: C, 61.82, H, 6.43, N, 10.11.

EXAMPLE 72

1-(1-{2-[4-(6-Amino-pyridin-2-yl)-phenyl]-ethyl}-pyrrolidin-3-yl)-3-phenyl-urea

Prepared from Example 73, using phenylisocyanate, in 53.5% yield, mp 130° C. (dec.) as the hydrochloride salt from methylene chloride/ether.

$^1$H-NMR (CDCl$_3$, δ): 1.64 (m, 1H), 2.22 (m, 2H), 2.46 (m, 1H), 2.69 (m, 2H), 2.79 (m, 4H), 2.97 (m, 1H), 4.25 (bs, 1H, NH), 4.54 (bs, 2H, NH), 5.94 (bs, 1H, NH), 6.40 (d, J=8, 1H), 6.9–7.0 (m, 3H), 7.2–7.3 (m, 5H), 7.46 (t, J=8, 1H), 7.80 (m, 2H). $^{13}$C-NMR (CDCl$_3$, δ): 32.3, 34.7, 49.4, 53.1, 57.3, 61.0, 107.1, 110.8, 119.9, 122.8, 126.9, 128.8, 129.0, 137.6, 138.5, 139.3, 140.6, 155.8, 156.0, 158.4. MS (%): 402 (parent+1, 97), 197 (48), 155 (48), 133 (100), 119 (78), 103 (48). Anal. Calc'd. for C$_{24}$H$_{27}$N$_5$O.2HCl.1/2C$_4$H$_{10}$O.1/2CH$_2$Cl$_2$: C, 57.46, H, 6.37, N, 12.64. Found: C, 57.74, H, 6.35, N, 12.44.

EXAMPLE 73

1-(1-{2-[4(6-Amino-pyridin-2-yl)-phenyl]-ethyl}-pyrrolidin-3-yl)-3-benzyl-urea

Prepared from Example 73, using benzylisocyanate, in 42% yield, mp 90° C. (dec.) as the hydrochloride salt from methylene chloride/ether.

$^1$H-NMR (CDCl$_3$, δ): 1.65 (m, 1H), 2.19 (m, 2H), 2.45 (m, 1H), 2.6–2.8 (m, 6H), 2.95 (m, 1H), 4.17 (m, 1H), 4.28 (d, J=6, 2H), 4.52 (m, 2H, NH), 5.27 (m, 1H), 6.40 (d, J=8, 1H), 7.01 (d, J=7, 1H), 7.2–7.3 (m, 7H), 7.45 (t, J=8, 1H), 7.79 (m, 2H). $^{13}$C-NMR (CDCl$_3$, δ): 32.4, 34.7, 44.3, 49.7, 53.0, 57.2, 61.0, 107.0, 110.7, 126.8, 127.1, 127.5, 128.5, 128.8, 137.6, 138.4, 139.5, 140.5, 155.9, 157.8, 158.2. MS (%): 416 (parent+1, 100), 197 (52), 133 (63), 119 (55), 91 (65). Anal. Calc'd. for C$_{21}$H$_{29}$N$_5$O.2HCl.1/2C$_4$H$_{10}$O.1/2CH$_2$Cl$_2$.1/2H$_2$O: C, 57.25, H, 6.64, N, 12.14. Found: C, 56.93, H, 6.64, N, 11.74.

EXAMPLE 74

1-(1-{2-[4-(6-Amino-pyridin-2-yl)-phenyl]-ethyl}-pyrrolidin-3-yl)-3-cyclohexyl-urea Prepared from Example 73, using cyclohexylisocyanate, in 27% yield, mp 120° C. (dec.) as the hydrochloride salt from methylene chloride/ether.

$^1$H-NMR (CDCl$_3$, δ): 1.02 (m, 3H), 1.26 (m, 3H), 1.50 (m, 1H), 1.60 (m, 3H), 1.83 (m, 2H), 2.56 (m, 1H), 2.69 (m, 2H), 2.79 (m, 2H), 2.91 (m, 1H), 3.47 (m, 1H), 4.18 (m, 1H), 5.50 (m, 1H), 6.38 (d, J=8, 1H), 6.99 (d, J=7, 1H), 7.19 (m, 2H), 7.42 (d, J=8, 1H), 7.79 (m, 2H). $^{13}$C-NMR (CDCl$_3$, δ): 25.0, 25.6, 32.3, 33.9, 34.7, 48.7, 49.4, 53.1, 57.5, 61.1, 107.0, 110.6, 126.9, 128.8, 137.7, 138.3, 140.4, 155.8, 157.4, 158.4. MS (%): 408 (parent+1, 95), 309 (62), 197 (100), 133 (61). Anal. Calc'd. for C$_{24}$H$_{33}$N$_5$O.2HCl.1/2C$_4$H$_{10}$O.1/2CH$_2$Cl$_2$.5/4H$_2$O: C, 54.64, H, 7.53, N, 12.02. Found: C, 54.52, H, 7.28, N, 12.00.

EXAMPLE 75

{2-[4-(6-Amino-pyridin-2-yl)-phenyl]-ethyl}-(8-methyl-8-aza-bicyclo[3.2.1]oct-3-yl)-amine Prepared as in Example 1, using (8-methyl-8-aza-bicyclo[3.2.1]oct-3-yl)-2-amine, in 27% yield, mp 98° C. (dec.) as the hydrochloride salt from ether. $^1$H-NMR (CDCl$_3$, δ): 0.9–1.9 (multiplets, 8H), 2.49 (s, 3H), 2.8–3.0 (m, 6H), 3.25 (m, 1H), 3.49 (bs, 2H, NH), 6.42 (d, J=8, 1H), 7.02 (d, J=7, 1H), 7.23 (m, 2H), 7.46 (t, J=8, 1H), 7.81 (m, 2H). MS (%): 337 (parent+1, 100). Anal. Calc'd. for C$_{21}$H$_{28}$N$_4$.3HCl.5/2H$_2$O.1/4C$_4$H$_{10}$O: C, 51.87, H, 7.62, N, 11.00. Found: C, 51.87, H, 7.58, N, 10.98.

EXAMPLE 76

{2-[4-(6-Amino-pyridin-2-yl)-phenyl]-ethyl}-(3-benzyl-3-aza-bicyclo[3.1.0]hex-6-yl)-amine Prepared as in Example 1, using 3-benzyl-3-aza-bicyclo[3.1.0]hex-6-amine, in 19% yield, as a tan solid, as the hydrochloride salt.

$^1$H-NMR (CDCl$_3$, δ): 1.42 (m, 2H), 2.38 (m, 2H), 2.51 (m, 1H), 2.84 (m, 2H), 2.94 (m, 4H), 3.55 (s, 2H), 4.52 (bs, 2H, NH), 6.41 (d, J=8, 1H), 7.04 (d, J=8, 1H), 7.2–7.3 (m, 7H), 7.46 (t, J=8, 1H), 7.83 (m, 2H). $^{13}$C-NMR (CDCl$_3$, δ): 24.3, 35.7, 38.7, 50.5, 54.4, 59.1, 106.9, 110.7, 126.8, 126.9, 128.2, 128.6, 128.9, 137.7, 138.4, 139.5, 140.4, 156.0, 158.2. MS (%): 385 (parent+1, 20), 155 (64), 119 (100). not—Anal. Calc'd. for C$_{23}$H$_{31}$N$_5$O.HCl.1/4H$_2$O.CH$_2$Cl$_2$: C, 55.50, H, 6.64, N, 13.48. Found: C, 55.79, H, 6.85, N, 13.10.

EXAMPLE 77

{2-[4-(6-Amino-pyridin-2-yl)-phenyl]-ethyl}-[8-(4-fluoro-benzyl)-8-aza-bicyclo[3.2.1]oct-3-yl]-amine Prepared as in Example 1, using 8-(4-fluoro-benzyl)-8-aza-bicyclo[3.2.1]oct-3-amine, in 22% yield, mp 190° C. (dec.) as the hydrochloride salt.

$^1$H-NMR (CDCl$_3$, δ): 1.43 (m, 2H), 1.52 (m, 2H), 1.70 (m, 2H), 1.95 (m, 2H), 2.7–2.8 (m, 5H), 3.14 (m, 2H), 3.50 (s, 2H), 4.49 (bs, 2H, NH), 6.41 (d, J=8, 1H), 6.94 (m, 2H), 7.04 (d, J=8, 1H), 77.24 (m, 2H), 7.30 (m, 2H), 7.46 (t, J=8, 1H), 7.83 (m, 2H). $^{13}$C-NMR (CDCl$_3$, δ): 27.0, 36.4, 38.3, 48.0, 48.9, 54.8, 58.3, 106.9, 110.7, 114.7, 114.9, 126.7, 126.8, 126.9, 128.9, 129.8, 129.9, 135.9, 137.8, 138.3, 140.6, 156.0, 158.2, 160.5, 162.9. MS (%): 431 (parent+1, 44), 218 (56), 109 (100). Anal. Calc'd. for C$_{27}$H$_{31}$N$_4$F.3HCl.3/2H$_2$O: C, 57.20, H, 6.58, N, 9.88. Found: C, 57.30, H, 6.91, N, 9.56.

EXAMPLE 78

{2-[4-(6-Amino-pyridin-2-yl)-phenyl]-ethyl}-[8-(4-chloro-benzyl)-8-aza-bicyclo[3.2.1]oct-3-yl]-amine Prepared as in Example 1, using 8-(4-chloro-benzyl)-8-aza-bicyclo[3.2.1]oct-3-amine, in 29% yield, mp 198° C. (dec.) as the hydrochloride salt.

$^1$H-NMR (CDCl$_3$, δ): 1.42 (m, 2H), 1.52 (m, 2H), 1.68 (m, 2H), 1.94 (m, 2H), 2.8–2.9 (m, 5H), 3.13 (bs, 2H), 3.49 (s, 2H), 4.53 (bs, 2H, NH), 6.40 (d, J=8, 1H), 7.03 (d, J=7, 1H), 7.2–7.3 (m, 7H), 7.45 (t, J=8, 1H), 7.82 (m, 2H). $^{13}$C-NMR (CDCl$_3$, δ): 24.0, 36.2, 37.9, 47.9, 49.0, 54.8, 58.1, 107.0, 110.7, 126.8, 127.0, 128.2, 128.3, 128.9, 129.8, 130.0, 132.2, 137.8, 138.4, 138.7, 140.4, 156.0, 158.2. MS (%): 447 (parent+1, 45), 234 (54), 125 (100). Anal. Calc'd. for C$_{27}$H$_{31}$N$_4$Cl.3HCl.1/2H$_2$O: C, 57.36, H, 6.24, N, 9.91. Found: C, 57.27, H, 6.44, N, 9.57.

EXAMPLE 79

4-Amino-1-{2-[4-(6-amino-pyridin-2-yl)-phenyl]-ethyl}-piperidine-4-carboxylic Acid phenethyl-amide Prepared as in Example 1, using 4-amino-piperidine-4-carboxylic acid phenethyl-amide, in 12% yield, mp 215–219° C. (dec.) as the hydrochloride salt.

¹H-NMR (CDCl₃, δ): 1.31 (m, 2H), 1.80 (bs, 2H), 2.25 (m, 4H), 2.62 (m, 2H), 2.8–3.0 (m, 6H), 3.48 (m, 2H), 4.49 (bs, 2H, NH), 6.41 (d, J=8, 1H), 7.04 (d, J=7, 1H), 7.2–7.4 (m, 7H), 7.46 (t, J=8, 1H), 7.82 (m, 2H). ¹³C-NMR (CDCl₃, δ): 33.4, 35.0, 35.8, 40.4, 49.0, 55.2, 60.4, 106.9, 110.7, 126.4, 126.8, 128.5, 128.8, 128.9, 137.6, 138.3, 139.1, 140.9, 156.0, 158.2, 176.9. MS (%): 444 (parent+1, 15), 197 (54), 133 (100). Anal. Calc'd. for C₂₇H₃₃N₅O.3HCl: C, 58.65, H, 6.56, N, 12.66. Found: C, 58.29, H, 6.97, N, 12.28.

EXAMPLE 80

3-{2-[4-(6-Amino-pyridin-1-yl)-phenyl-ethylamino}-pyrrolidine-1-carboxylic Acid phenylamide Prepared as in Example 1, using 3-amino-pyrrolidine-1-carboxylic acid phenylamide, in 8% yield, mp 130° C. (dec.) as the hydrochloride salt from ethyl ether.

¹H-NMR (CDCl₃, δ): 1.64 (m, 1H), 2.20 (m, 2H), 2.46 (dd, J=3,7, 1H), 2.66 (m, 2H), 2.78 (m, 4H), 2.97 (m, 1H), 4.25 (bs, 1H, NH), 4.53 (bs, 2H, NH), 5.85 (d, J=7, 1H), 6.40 (d, J=8, 1H), 6.9–7.0 (m, 3H), 7.2–7.3 (m, 5H), 7.46 (t, J=8, 1H), 7.79 (m, 2H). ¹³C-NMR (CDCl₃, δ): 32.4, 34.8, 49.6, 53.1, 57.3, 61.0, 107.1, 110.8, 120.0, 122.9, 126.9, 128.8, 129.0, 137.6, 138.4, 139.2, 140.7, 155.6, 156.0, 158.3. MS (%): 402 (parent+1, 100), 283 (20), 264 (18). Anal. Calc'd. for C₂₄H₂₇N₅O.2HCl.H₂O.C₄H₁₀O: C, 59.36, H, 7.29, N, 12.36. Found: C, 59.34, H, 6.69, N, 12.59.

EXAMPLE 81

(3-{2-[4-(6-Amino-pyridin-2-yl)-phenyl]-ethylamino}-pyrrolidin-1-yl)-phenyl-methanone Prepared as in Example 1, using 3-amino-pyrrolidin-1-yl-phenyl-methanone, in 10% yield, mp 130° C. (dec.) as the hydrochloride salt from ethyl ether.

¹H-NMR (CDCl₃, δ): 1.71 (m, 1H), 1.98 and 2.13 (multiplets, 1H), 2.7–3.0 (m, 3H), 3.2–3.8 (multiplets, 6H), 4.51 (bs, 2H, NH), 6.42 (d, J=8, 1H), 7.04 (t, J=7, 1H), 7.20 (d, J=8, 1H), 7.26 (m, 1H), 7.38 (m, 3H), 7.46 (m, 3H), 7.83 (m, 2H). ¹³C-NMR (CDCl₃, δ): 30.8, 32.5, 36.0, 44.7, 47.8, 49.2, 49.3, 52.1, 55.1, 56.3, 57.9, 107.0, 110.75, 127.0, 127.1, 128.2, 128.3, 128.9, 129.9, 137.9, 138.4, 140.0, 155.8, 158.2, 169.8. MS (%): 387 (parent+1, 75), 155 (44), 119 (100), 105 (60). Anal. Calc'd. for C₂₄H₂₆N₄O.HCl.1/2CH₂Cl₂.C₄H₁₀O: C, 63.44, H, 7.10, N, 10.38. Found: C, 63.33, H, 6.72, N, 10.39.

EXAMPLE 82

6-{4-[2-(1-Benzyl-pyrrolidin-3-ylamino)-ethyl]-phenyl}-pyridin-2-ylamine

Prepared as in Example 1, using 1-benzyl-pyrrolidin-3-ylamine, in 27% yield, mp 145° C. (dec.) as the hydrochloridel salt.

¹H-NMR (CDCl₃, δ): 1.49 (m, 1H), 2.08 (m, 1H), 2.26 (dd, J=5,9, 1H), 2.73 m, 1H), 2.81 (s, 4H), 3.29 (m, 1H), 3.56 (AB_q, J=19, Dn=13, 2H), 4.52 (bs, 2H, NH), 6.39 (d, J=8, 1H), 7.04 (d, J=7, 1H), 7.28 (m, 7H), 7.45 (t, J=8, 1H), 7.83 (m, 2H). ¹³C-NMR (CDCl₃, δ): 32.1, 36.3, 49.5, 53.0, 57.3, 60.5, 60.7, 106.9, 110.7, 126.88, 126.94, 128.2, 128.8, 128.9, 137.8, 138.3, 139.0, 140.5, 156.0, 158.3. MS (%): 373 (parent+1, 100), 155 (35), 119 (78), 103 (35). Anal. Calc'd. for C₂₄H₂₈N₄.3HCl.1/2H₂O: C, 58.72, H, 6.57, N, 11.41. Found: C, 58.37, H, 6.67, N, 11.23.

EXAMPLE 83

N-(8-{2-[4-(6-Amino-pyridin-2-yl)-phenyl]-ethyl}-8-aza-bicyclo[3.2.1]oct-3-yl)-benzamide Prepared as in Example 1, using 8-aza-bicyclo[3.2.1]oct-3-yl)-benzamide, in 29% yield, mp 211 ° C. (dec.) as the hydrochloride salt.

¹H-NMR (CDCl₃, δ): 1.67 (m, 2H), 1.78 (m, 2H), 1.92 (m, 2H), 2.00 (m, 2H), 3.39 (m, 2H), 4.36 (m, 1H), 4.47 (bs, 2H, NH), 5.96 (d, J=8, 1H), 6.42 (d, J=8, 1H), 7.04 (d, J=8, 1H), 7.26 (m, 2H), 7.40 (m, 2H), 7.47 (m, 2H), 7.70 (m, 2H), 7.82 (m, 2H). ¹³C-NMR (CDCl₃, δ): 26.4, 35.4, 37.65, 41.6, 53.8, 59.2, 106.9, 110.7, 126.8, 128.5, 128.9, 131.4, 134.7, 137.7, 138.3, 140.7, 156.0, 158.2, 166.7. MS (%): 427 (parent+1, 100). Anal. Calc'd. for C₂₇H₃₀N₄.2HCl.H₂O: C, 62.67, H, 6.62, N, 10.83. Found: C, 62.85, H, 6.57, N, 10.52.

EXAMPLE 84

{2-[4-(6-Amino-pyridin-2-yl)-phenyl]-ethyl}-(3-benzyl-3-aza-bicyclo[3.3.1]non-9-yl)-amine Prepared as in Example 1, using (3-benzyl-3-aza-bicyclo[3.3.1]non-9-yl)-amine, in 24% yield, mp 190° C. (dec.) as the hydrochloride salt, as a mixture of endo and exo isomers.

¹H-NMR (CDCl₃, δ): 1.44 (m, 2H), 1.76 (m, 4H), 2.37 (m, 2H), 2.55 (m, 2H), 2.86 (s, 4H), 2.94 (m, 2H), 3.28 and 3.27 (singlets, 2H, endo and exo isomers in roughly 1:1 ratio, N-benzyl CH₂ group), 4.47 (bs, 2H, NH), 6.44 (dd, J=2,8, 1H), 7.07 (dd, J=3,7, 1H), 7.1–7.3 (m, 7H), 7.47 (dt, J=2,8, 1H), 7.86 (m, 2H). ¹³C-NMR (CDCl₃, δ): 21.2, 24.5, 32.3, 33.0, 47.8, 53.1, 60.2, 63.5, 63.8, 106.9, 110.7, 126.2, 126.6, 126.9, 128.1, 128.2, 128.6, 128.7, 128.9, 129.0, 138.3, 139.0, 141.0, 158.0, 159.0. MS (%): 427 (parent+1, 68), 91 (100). Anal. Calc'd. for C₂₈H₃₄N₄.3HCl.1/2H₂O: C, 61.71, H, 7.03, N, 10.28. Found: C, 61.86, H, 7.19, N, 9.97.

EXAMPLE 85

N-(8-{2-[4-(6-Amino-pyridin-2-yl)-phenyl]-ethyl}-8-aza-bicyclo[3.2.1]oct-3-yl)-2-(4-fluoro-phenyl)-acetamide Prepared as in Example 1, using 8-aza-bicyclo[3.2.1]oct-3-yl)-2-(4-fluoro-phenyl)-acetamide, in 23% yield, mp 160° C. (dec.) as the hydrochloride salt.

¹H-NMR (CDCl₃, δ): 1.49 (m, 2H), 1.69 (m, 2H), 1.76 (m, 2H), 1.93 (m, 2H), 2.58 (m, 2H), 2.81 (m, 2H), 3.33 (bs, 2H), 3.44 (s, 2H), 3.49 (s, 1H), 4.13 (m, 1H), 4.49 (bs, 2H, NH), 6.41 (d, J=8, 1H), 7.01 (m, 3H), 7.21 (m, 4H), 7.45 (t, J=8, 1H), 7.81 (m, 2H). ¹³C-NMR (CDCl₃, δ): 26.1, 35.1, 37.6, 37.8, 41.0, 42.9, 52.9, 54.0, 59.4, 107.0, 110.7, 115.7, 115.9, 126.9, 127.3, 128.9, 129.0, 129.4, 130.9, 137.8, 138.4, 140.3, 155.9, 158.2, 170.1. MS (%): 459 (parent+1, 100), 197 (21), 119 (31), 103 (36). Anal. Calc'd. for C₂₈H₃₁N₄FO.2HCl.1/2H₂O: C, 62.22, H, 6.34, N, 10.37. Found: C, 61.99, H, 6.50, N, 10.01.

EXAMPLE 86

6-{4-[2-(3-Amino-piperidin-1-yl)-ethyl]-phenyl}-pyridin-2-ylamine

Prepared as in Example 1, using 3-(t-butoxycarbonylamino)-piperidine, in 100% yield following condensation with (6-amino-pyridin-2-yl)-phenyl]-2-chloroethane and deblocking with trifluoroacetic acid in methylene chloride, mp 150° C. (dec.) as the hydrochloride salt.

¹H-NMR (CDCl₃, δ): 1.20 (m, 1H), 1.42 (m, 1H), 1.62 (m, 1H), 1.85 (m, 1H), 2.31 (td, J=2,9, 1H), 2.51 (m, 2H), 2.79 (m, 2H), 2.86 (m, 3H), 3.08 (m, 1H), (bs, 2H, NH), 6.39 (dd, J=1,8, 1H), 7.02 (dd, J=1,7, 1H), 7.23 (m, 2H), 7.44 (td, J=1,8, 1H), 7.81 (m, 2H). ¹³C-NMR (CDCl₃, δ): 25.1, 31.8, 36.3, 46.6, 48.1, 52.4, 54.75, 106.9, 110.7, 126.9, 128.9, 137.7, 138.3, 140.5, 156.0, 158.2. MS (%): 297 (parent+1, 57), 135 (40), 119 (100), 103 (62). Anal. Calc'd. for $C_{18}H_{24}N_4.3HCl.H_2O.1/2CH_2Cl_2$: C, 51.70, H, 6.80, N, 13.03. Found: C, 51.90, H, 6.64, N, 12.59.

EXAMPLE 87

N-(3-{2-[4-(6-Amino-pyridin-2-yl)-phenyl]-ethyl}-3-aza-bicyclo[3.3.1]non-9-yl)-benzamide, Anti-isomer Prepared as in Example 1, using 3-aza-bicyclo[3.3.1]non-9-yl)-benzamide, anti-isomer, in 18% yield, mp 185° C. (dec.) as the hydrochloride salt.

$^1$H-NMR (CDCl$_3$, δ): 1.35 (m, 1H), 1.71 (m, 4H), 1.95 (m, 2H), 2.4–2.5 (m, 5H), 2.79 (m, 2H), 3.04 (m, 2H), 4.10 (m, 1H), 4.53 (bs, 2H, NH), 6.41 (dd, J-1,8, 1H), 6.42 (m, 1H), 7.05 (dd, J=1,7, 1H), 7.25 (m, 2H), 7.4–7.5 (m, 4H), 7.75 (m, 2H), 7.84 (m, 2H). $^{13}$C-NMR (CDCl$_3$, δ): 20.6. 25.3, 32.9, 33.5, 51.4, 59.5, 59.9, 106.8, 110.6, 126.6, 126.8, 128.6, 158.9, 131.3, 135.1, 137.3, 138.3, 141.5, 156.1, 158.2, 166.9. MS (%): 441 (parent+1, 41), 149 (75), 119 (100). Anal. Calc'd. for $C_{28}H_{32}N_4O.2HCl.1/2H_2O.1/4(C_4H_{10}O)$: C, 64.38, H, 6.99, N, 10.36. Found: C, 64.49, H, 6.43, N, 9.91.

EXAMPLE 88

N-(3-{2-[4-(6-Amino-pyridin-2-yl)-phenyl]-ethyl}-3-aza-bicyclo[3.3.1]non-9-yl)-benzamide, Syn-isomer Prepared as in Example 1, using 3-aza-bicyclo[3.3.1]non-9-yl)-benzamide, syn-isomer, in 9% yield, as a hygroscopic solid as the hydrochloride salt.

$^1$H-NMR (CDCl$_3$, δ): 1.37 (m, 1H), 1.81 (m, 4H), 2.00 (m, 2H), 2.33 (m, 1H), 2.51 (m, 4H), 2.83 (m, 4H), 4.04 (m, 1H), 4.48 (bs, 2H, NH), 6.42 (dd, J=1,8, 1H), 7.05 (dd, J=1,7, 1H), 7.24 (m, 2H), 7.4–7.5 (m, 4H), 7.74 (m, 2H), 7.82 (m, 2H). $^{13}$C-NMR (CDCl$_3$, δ): 20.3, 31.9, 33.4, 33.7, 50.8, 53.8, 60.5, 107.1, 110.7, 126.7, 126.8, 128.6, 128.9, 131.3, 135.1, 137.0, 138.6, 141.4, 155.6, 158.1, 166.6. MS (%): 441 (parent+1, 5), 391 (10), 167 (23), 149 (100). Anal. Calc'd. for $C_{28}H_{32}N_4O.HCl.1/2CH_2Cl_2.1/2(C_4H_{10}O)$: C, 65.82, H, 7.06, N, 10.07. Found: C, 66.20, H, 6.80, N, 10.10.

EXAMPLE 89

6-{4-[2-(4-Benzhydryl-piperazin-1-yl)-ethyl]-phenyl}-pyridin-2-ylamine

Prepared as in Example 1, using 4 benzhydryl-piperazine, in 54% yield, mp 170° C. (dec.) as the hydrochloride salt.

$^1$H-NMR (CDCl$_3$, δ): 2.45 (m, 4H), 2.56 (m, 4H), 2.61 (m, 2H), 2.82 (m, 2H), 4.24 (s, 1H), 4.54 (bs, 2H, NH), 6.37 (d, J=8, 1H), 7.04 (d, J=8, 1H), 7.19 (m, 2H), 7.26 (m, 6H), 7.42 (m, 5H), 7.85 (m, 2H). $^{13}$C-NMR (CDCl$_3$, δ): 33.4, 51.9, 52.0, 53.5, 60.4, 106.8, 110.6, 126.8, 126.9, 128.0, 128.5, 128.9, 137.6, 138.3, 141.0, 142.8, 156.0, 158.3. MS (%): 449 (parent+1, 17), 253 (12), 167 (100), 149 (14). Anal. Calc'd. for $C_{30}H_{32}N_4.2HCl.1/4CH_2Cl_2$: C, 66.94, H, 6.41, N, 10.32. Found: C, 66.57, H, 6.22, N, 10.17.

EXAMPLE 90

6-{4-[2-(4-Benzhydryl-piperidin-1-yl)-ethyl]-phenyl}-pyridin-2-ylamine

Prepared as in Example 1, using 4-benzhydryl-piperidine, in 24% yield, mp 175° C. (dec.) as the hydrochloride salt.

$^1$H-NMR (CDCl$_3$, δ): 1.32 (m, 2H), 1.56 (m, 2H), 2.11 (m, 2H), 2.14 (m, 1H), 2.61 (m, 2H), 2.83 (m, 2H), 2.99 (m, 2H), 3.50 (d, J=11, 1H), 4.46 (bs, 2H, NH), 6.41, (dd, J=0.5,8, 1H), 7.04 (dd, J=0.5,7.5, 1H), 7.14 (m, 2H), 7.2–7.3 (m, 10H), 7.46 (t, J=8, 1H), 7.82 (m, 2H). $^{13}$C-NMR (CDCl$_3$, δ): 31.2, 33.4, 39.5, 53.9, 58.9, 60.6, 106.9, 110.7, 126.2, 126.8, 128.0, 128.5, 128.9, 138.3, 143.7, 156.0, 158.2. MS (%): 448 (parent+1, 100), 264 (32), 149 (70). Anal. Calc'd. for $C_{31}H_{33}N_3.2HCl.1/4CH_2Cl_2$: C, 69.28, H, 6.60, N, 7.76. Found: C, 68.96, H, 6.48, N, 7.36.

EXAMPLE 91

3-{2-[4-(6-Amino-pyridin-2-yl)-phenyl]-ethyl}-3-aza-bicyclo[3.3.1]non-9-ylamine

Prepared as in Example 1, using 3-aza-bicyclo[3.3.1]non-9-ylamine t-butylcarbamate followed by deprotection using trifluoroacetic acid in methylene chloride in 85% yield, as a low-melting solid as the hydrochloride salt.

$^1$H-NMR (CDCl$_3$, δ): 1.28 (m, 1H), 1.48 (m, 2H), 1.61 (bs, 2H), 1.82 (m, 2H), 2.26 (m, 2H), 2.35 (m, 1H), 2.46 (t, J=7, 2H), 2.78 (m, 3H), 3.02 (m, 2H, 4.46 (bs, 2H, NH), 6.41 (dd, J=0.5,8, 1H), 7.05 (d, J=0.6,7, 1H), 7.24 (m, 2H), 7.46 (t, J=8, 1H), 7.82 (m, 2H). $^{13}$C-NMR (CDCl$_3$, δ): 20.9, 24.1, 33.7, 36.1, 52.8, 60.2, 106.7, 110.7, 126.6, 128.9, 137.2, 138.3, 141.7, 156.2, 158.1. MS (%): 337 (parent+1, 13), 279 (14), 167 (30), 149 (100), 113 (39). Anal. Calc'd. for $C_{21}H_{28}N_4.2HCl.1/2CH_2Cl.(C_4H_{10}O)$: C, 58.23, H, 7.86, N, 10.65. Found: C, 58.15, H, 7.31, N, 10.72.

EXAMPLE 92

3-{2-[4-(6-Amino-pyridin-2-yl)-phenyl]-ethyl}-3-aza-bicyclo[3.1.0]hexane-6-carboxylic Acid Ethyl Ester Prepared as in Example 1, using 3-aza-bicyclo[3.1.0] hexane-6-carboxylic acid ethyl ester in 18% yield, as a low melting solid as the hydrochloride salt.

$^1$H-NMR (CDCl$_3$, δ): 1.23 (t, J=7, 3H), 1.93 (bs, 2H), 1.99 (bs, 1H), 2.40 (d, J=9, 1H), 2.65 (m, 2H), 2.71 (m, 2H), 3.12 (d, J=9, 2H), 4.49 (bs, 2H, NH), 6.40 (d, J=8, 1H), 7.04 (d, J=7.5, 1H), 7.21 (m, 2H), 7.45 (t, J=7.5, 1H), 7.81 (m, 2H). $^{13}$C-NMR (CDCl$_3$, δ): 14.3, 21.8, 26.3, 35.1, 54.4, 56.4, 30.2, 106.8, 110.7, 126.7, 128.8, 137.5, 138.3, 141.0, 156.1, 158.2, 173.9. MS (%): 352 (parent+1, 5), 167 (22), 149 (100), 113 (20). Anal. Calc'd. for $C_{21}H_{25}N_3O_2.2HCl$: C, H, N. Found: C, H, N.

EXAMPLE 93

3-{2-[4-(6-Amino-pyridin-2-yl)-phenyl]-ethyl}-3-aza-bicyclo[3.1.0]hexane-6-carboxylic Acid Prepared by hydrolysis of Example 92 using 2N hydrochloric acid at 70° C. for 8 h in 83% yield, as a low-melting solid as the hydrochloride salt.

$^1$H-NMR (HCl salt, CDCl$_3$, δ): 2.18 (s, 2H), 2.31 (m, 2H), 3.28 (s, 1H), 3.4–3.6 (m, 4H), 3.89 (m, 2H), 6.96 (m, 1H), 7.15 (m, 1H), 7.53 (m, 2H), 7.79 (m, 2H), 7.94 (m, 1H). $^{13}$C-NMR (CDCl$_3$, δ): 24.3, 29.2, 31.5, 38.8, 55.7, 110.7, 111.6, 124.7, 127.6, 128.5, 130.0, 130.6, 131.0, 140.0, 144.6, 146.4, 155.4, 167.9. MS (%): 324 (parent+1, 23), 279 (11), 167 (25), 149 (100), 129 (12), 113 (27). HRMS Calc'd. for $C_{19}H_{22}N_3O_2$ (parent+1): 324.1712. Found: 324.1717.

EXAMPLE 94

3-{2-[4-(6-Amino-pyridin-2-yl)-phenyl]-ethylamino}-piperidine-1-carboxylic Acid tert-butyl Ester Prepared as in Example 1, using piperidine-1-carboxylic acid tert-butyl ester in 29% yield as a foam.

¹H-NMR (CDCl₃, δ): 1.43 (s, 9H), 1.6–1.8 (m, 3H), 2.35 (m, 2H), 2.54 (m, 3H), 2.76 (t, J=8, 2H), 3.74 (m, 1H), 4.55 (bs, 2H), 5.03 (bs, 1H), 6.39 (d, J=8, 1H), 7.03 (d, J=7, 1H), 7.22 (m, 2H), 7.44 (t, J=8, 1H), 7.83 (m, 2H). ¹³C-NMR (CDCl₃, δ): 22.3, 28.5, 29.7, 33.3, 46.3, 53.8, 58.5, 60.3, 78.9, 106.8, 110.6, 126.8, 128.9, 13.5, 138.3, 141.0, 155.2, 156.0, 158.3. MS (%): 397 (parent+1, 56), 297 (38), 280 (48), 213 (40), 197 (95), 157 (100). HRMS Calc'd. for $C_{23}H_{33}N_4O_2$ (parent+1): 397.26035. Found: C, 397.2581.

EXAMPLE 95

6-{4-[2-(Piperidin-3-ylamino)-ethyl]-phenyl}-pyridin-2-ylamine

Prepared by deprotection of Example 94 using trifluoroacetic acid in methylene chloride in 92% yield, as the hydrochloride salt from ethyl ether.

¹H-NMR (CDCl₃, δ): 1.35 (bs, 2H), 1.58 (m, 1H), 1.69 (m, 1H), 1.85 (m, 1H), 2.07 (m, 1H), 2.60 (m, 2H), 2.74 (m, 1H), 2.79 (m, 2H), 2.81 (m, 4H), 4.47 (bs, 2H), 6.41 (d, J=8, 1H), 7.04 (d, J=8, 1H), 7.23 (m, 2H), 7.46 (t, J=8, 1H), 7.82 (m, 2H). ¹³C-NMR (CDCl₃, δ): 23.8, 33.3, 34.2, 48.1, 53.6, 60.6, 62.7, 106.8, 110.7, 126.8, 128.9, 137.5, 138.3, 141.1, 156.0, 158.2. FAB MS (%): 297 (parent+1, 12), 167 925), 149 (100), 119 (27), 111 (25). Anal. Calc'd. for $C_{18}H_{24}N_4 \cdot 3HCl \cdot H_2O \cdot 1/4(C_4H_{10}O)$: C, 51.59, H, 7.18, N, 12.67, Found: C, 51.86, H, 7.23, N, 12.31.

EXAMPLE 96

6-{4-[2-(1-Benzyl-piperidin-4-ylamino)-ethyl]-phenyl}-pyridin-2-ylamine

Prepared as in Example 1, using 1-benzyl-4-aminopiperidine in 82% yield (purification was effected by forming the t-butylcarbamate derivative followed by chromatography and deprotection with trifluoroacetic acid in methylene chloride), as the hydrochloride salt.

¹H-NMR (CDCl₃, δ): 1.38 (m, 2H), 1.80 (m, 2H), 1.99 (m, 2H), 2.46 (m, 1H), 2.83 (m, 4H), 2.90 (m, 2H), 3.48 (s, 2H), 4.57 (bs, 2H), 6.40 (d, J=8, 1H), 7.05 (d, J=7, 1H), 7.30 (m, 7H), 7.45 (t, J=8, 1H), 7.85 (m, 2H). ¹³C-NMR (CDCl₃, δ): 32.7, 36.3, 48.0, 52.5, 54.9, 36.1, 106.9, 110.7, 126.9, 128.2, 128.9, 129.1, 137.8, 138.3, 138.6, 140.6, 156.0, 158.3. FAB MS (%): 387 (parent+1, 47), 174 (31), 149 (100), 119 (97), 103 (52). HRMS Calc'd. for $C_{25}H_{30}N_4$: 387.2548. Found: 387.2582.

EXAMPLE 97

3-{2-[4-(6-Amino-pyridin-2-yl)-phenyl]-ethyl}-3-aza-bicyclo[3.1.0]hex-6-ylamine (anti-isomer)

Prepared is in Example 1, using 3-aza-bicyclo[3.1.0]hex-6-ylamine (anti-isomer) t-butylcarbarnate followed by deprotection using trifluoroacetic acid in methylene chloride in 79% yield, as the hydrochloride salt from ethyl ether.

¹H-NMR (CDCl₃, δ): 1.34 (m, 2H), 1.90 (bs, 2H), 2.29 (t, J=7,1H), 2.63 (m, 2H), 2.69 (m, 2H), 2.76 (m, 2H), 3.09 (d, J=9, 2H), 4.52 (bs, 2H), 6.41 (d, J=8, 1H), 7.04 (d, J=8, 1H), 7.22 (m, 2H), 7.45 (t, J=8, 1H), 7.82 (m, 2H). ¹³C-NMR (CDCl₃, δ): 19.9, 34.4, 35.4, 52.7, 57.0, 106.8, 110.7, 126.7, 128.8, 137.5, 138.3, 141.2, 156.1, 158.2. FAB MS (%): 295 (parent+1, 3), 279 (10), 167 (20), 149 (100), 129 (6), 113 (25). Anal. Calc'd. for $C_{18}H_{22}N_4 \cdot 2HCl \cdot 1/4CH_2C_2 \cdot 1/2(C_4H_{10}O) \cdot 5/4H_2O$: C, 54.27, H, 7.20, N, 12.50. Found: C, 53.92, H, 6.83, N, 12.19.

EXAMPLE 98

6-{4-[2-(Piperidin-4-ylamino)-ethyl]-phenyl}-pyridin-2-ylamine

Prepared by deblocking Example 96 using ammonium formate and 10% palladium-on-carbon in refluxing ethanol in 67.5% yield, as the hydrochloride salt from ethyl ether.

¹H-NMR (CDCl₃, δ): 1.30 (m, 2H), 1.87 (m, 2H), 2.65 (m, 3H), 2.81 (m, 2H), 2.88 (m, 2H), 3.13 (m, 2H), 4.54 (bs, 2H), 6.42 9d, J=8, 1H), 7.04 (d, J=8, 1H), 7.25 (m, 2H), 7.46 (t, J=8, 1H), 7.83 (m, 2H). ¹³C-NMR (CDCl₃, δ): 32.3, 36.1, 44.2, 47.7, 53.9, 107.0, 110.7, 127.0, 128.9, 137.8, 138.4, 140.3, 155.95, 158.3. MS (%): 297 (parent+1, 10), 199 (35), 149 (100), 119 (30). Anal. Calc'd. for $C_{18}H_{24}N_4 \cdot 3HCl \cdot 1/4CH_2Cl_2 \cdot 1/2(C_4H_{10}O)$: C, 53.70, H, 7.32, N, 12.52. Found: C, 53.61, H, 6.99, N, 12.18.

EXAMPLE 99

6-(4-{2-[(Piperidin-4-ylmethyl)-amino]-ethyl}-phenyl)-pyridin-2-ylamine

Prepared as in Example 1, using 4-aminomethylpiperidine-1-t-butylcarbamate followed by deprotection using trifluoroacetic acid in methylene chloride in 80.5% yield, as the hydrochloride salt.

¹H-NMR (CDCl₃, δ): 1.25 (m, 3H), 1.87 (m, 2H), 2.65 (m, 2H), 2.81 (m, 2H), 2.88 (m, 2H), 3.13 (m, 2H), 4.54 (bs, 2H), 6.42 (d, J=8, 1H), 7.04 (d, J=8, 1H), 7.26 (m, 2H), 7.46 (t, J=8, 1H), 7.83 (m, 2H). ¹³C-NMR (CDCl₃, δ): 32.3, 36.1, 44.2, 47.7, 53.9, 107.0, 110.7, 127.0, 128.9, 137.8, 138.4, 140.3, 155.95, 158.3. FAB MS (%): 297 (parent+1, 16), 199 (35), 149 (100), 119 (30). Anal. Calc'd. for $C_{19}H_{26}N_4 \cdot 3HCl 7/4H_2O \cdot 3/4(C_4H_{10}O)$: C, 52.12, H, 7.95, N, 11.05. Found: C, 52.62, H, 7.59, N, 10.96.

EXAMPLE 100

(3-{2-[4-(6-Amino-pyridin-2-yl)-phenyl]-ethyl}-3-aza-bicyclo[3.1.0]hex-6-yl)-(4-methyl-piperazin-1-yl)-methanone Prepared as in Example 1, using 3-aza-bicyclo[3.1.0]hex-6-yl)-(4-methyl-piperazin-1-yl)-methanone in 14% yield, as the hydrochloride salt.

¹H-NMR (CDCl₃, δ): 1.94 (bs, 2H), 2.09 (bs, 1H), 2.2–2.4 (m, 8H), 2.27 (s, 3H), 2.68 (m, 2H), 2.73 (m, 2H), 3.11 (m, 2H), 3.61 (m, 4H), 4.49 (bs, 2H), 6.41 (d, J=8, 1H), 7.03 (d, J=8, 1H), 7.21 (m, 2H), 7.45 (t, J=8, 1H), 7.81 (m, 2H). ¹³C-NMR (CDCl₃, δ): 19.7, 25.6, 35.1, 41.8, 45.5, 46.0, 54.5, 54.7, 55.3, 56.7, 106.9, 110.7, 126.7, 1228.8, 137.5, 138.3, 140.9, 156.0, 158.0, 171.1. MS (%): 406 (parent+1, 3), 391 (20), 167 (18), 149 (100), 113 (19). Anal. Calc'd. for $C_{24}H_{31}N_5O \cdot 3HCl \cdot 2H_2O \cdot 5/4(C_4H_{10}O)$: C, 54.12, H, 7.91, N, 10.88. Found: C, 53.97, H, 7.57, N, 10.56.

EXAMPLE 101

{2-[4-(6-Amino-pyridin-2-yl)-phenyl]-ethyl}-(9-benzyl-3-oxa-9-aza-bicyclo[3.3.1]non-7-yl)-amine (more polar diastereomer)

Prepared as in Example 1, using (9-benzyl-3-oxa-9-aza-bicyclo[3.3.1]non-7-yl)-amine, more polar diastereomer, in 38% yield, as a foam as the hydrochloride salt.

¹H-NMR (CDCl₃, δ): 1.52 (m, 2H), 2.26 (m, 2H), 2.56 (m, 2H), 2.88 (m, 4H), 2.97 (m, 1H), 3.47 (m, 2H), 3.79 (s, 2H), 3.82 (m, 2H), 4.50 (bs, 2H), 6.41 (d, J=8, 1H), 7.05 (d, J=8, 1H), 7.2–7.4 (m, 7H), 7.46 (t, J=8, 1H), 7.83 (m, 2H). ¹³C-NMR (CDCl₃, δ): 27.4, 36.7, 48.4, 49.0, 50.8, 56.1, 69.5, 106.8, 110.7, 126.7, 127.0, 128.3, 128.5, 128.9, 137.5, 138.3, 139.0, 141.2, 156.1, 158.2. MS (%): 429 (parent+1, 42), 216 (53), 91 (100).

Anal. Calc'd. for $C_{27}H_{32}N_4O \cdot 3HCl \cdot H_2O$: C 58.33, H 4.71, N 10.08. Found: C 58.12, H 6.82, N 9.83.

EXAMPLE 102

{2-[4-(6-Amino-pyridin-2-yl)-phenyl]-ethyl}-(9-benzyl-3-oxa-9-aza-bicyclo[3.3.1]non-7-yl)-amine (less polar diastereomer)

Prepared as in Example 1, using (9-benzyl-3-oxa-9-aza-bicyclo[3.3.1]non-7-yl)-amine, less polar diastereomer, in 32% yield, mp 215° C. (dec.) as the hydrochloride salt.

$^1$H-NMR (CDCl$_3$, δ): 1.74 (m, 4H), 2.685 (bs, 2H), 2.86 (m, 2H), 2.97 (m, 2H), 3.70 (m, 3H), 3.80 (s, 2H), 3.87 (m, 2H), 4.52 (bs, 2H), 6.42 (d, J=8, 1H), 7.06 (d, J=7, 1H), 7.2–7.4 (m, 7H), 7.47 (t, J=8, 1H), 7.86 (m, 2H). $^{13}$C-NMR (CDCl$_3$, δ): 31.3, 36.4, 47.8, 50.8, 52.5, 55.9, 71.4, 106.9, 110.75, 127.0, 128.3, 128.5, 129.0, 137.8, 138.4, 139.2, 140.6, 156.1, 158.3. MS (%): 429 (parent+1, 12), 216 (67), 91 (100). Anal. Calc'd. for C$_{27}$H$_{32}$N$_4$O.3HCl.H$_2$O: C, 58.33, H, 6.71, N 10.08. Found: C, 58.30, H, 6.78, N 9.92.

EXAMPLE 103

2-(4-{2-[4-(6-Amino-pyridin-2-yl)-phenyl]-ethyl}-piperazin-1-yl)-1-phenyl-ethanol Prepared from Example 16, using sodium borohydride in methanol at room temperature for 2 h in 98.5% yield, mp 235° C. (dec.) as the hydrochloride salt. $^1$H-NMR (CDCl$_3$, δ): 2.51 (m, 6H), 2.63 (m, 4H), 2.82 (m, 4H), 4.10 (bs, 1H), 4.54 (bs, 2H), 4.74 (m, 1H), 6.39 (d, J=8, 1H), 7.05 (d, J=8, 1H), 7.2–7.4 (m, 7H), 7.45 (t, J=8, 1H), 7.84 (m, 2H). $^{13}$C-NMR (CDCl$_3$, δ): 33.4, 53.3, 60.3, 66.2, 68.8, 106.9, 110.7, 125.9, 126.9, 127.5, 128.4, 128.9, 137.7, 138.3, 140.8, 142.2, 156.0, 158.3. MS (%): 403 (parent+1, 100), 295 (54), 219 (41), 197 (76), 113 (35), 97 (89). Anal. Calc'd. for C$_{25}$H$_{30}$N$_4$O.3HCl.1/2H$_2$O: C, 57.64, H, 6.58, N 10.76. Found: C, 57.66, H, 6.45, N 10.77.

EXAMPLE 104

{2-[4-(6-Amino-pyridin-2-yl)-phenyl]-ethyl}-(3-oxa-9-aza-bicyclo[3.3.1]non-7-yl)-amine Prepared from Example 101, using ammonium formate and palladium-on-carbon in refluxing ethanol in 81% yield, mp 100° C. (dec.) as the hydrochloride salt.

$^1$H-NMR (CDCl$_3$, δ): 1.69 (m, 1H), 2.06 (m, 1H), 2.6–3.0 (m, 5H), 3.5–3.9 (m, 4H), 4.64 (bs, 2H), 6.35 (d, J=8, 1H), 7.00 (d, J=8, 1H), 7.23 (m, 2H), 7.40(t, J=8, 1H), 7.81 (m, 2H). MS (%): 339 (parent+1, 100), 254 (35), 199 (45), 159 (38). HRMS Calc'd. for C$_{20}$H$_{27}$N$_4$O (parent+1): 339.2184. Found: 339.2164.

EXAMPLE 105

6-(4-{2-[4-(2-Amino-2-phenyl-ethyl)-piperazin-1-yl]-ethyl}-phenyl)-pyridin-2-ylamine Prepared from Example 16, by forming the oxime methyl ether with O-methyl hydroxylamine hydrochloride in refluxing methanol followed by reduction using borane methyl sulfide in refluxing tetrahydrofuran in 54% yield, as the hydrochloride salt.

$^1$H-NMR (CDCl$_3$, δ): 2.2–2.9 (m, 14H), 4.12 (m, 1H), 4.52 (bs, 2H), 6.39 (d, J=8, 1H), 7.03 (d, J=7, 1H), 7.2–7.4 (m, 7H), 7.45 (t, J=7, 1H), 7.81 (m, 2H). MS (%): 402 (parent+1, 6), 149 (100), 119 (47). HRMS Calc'd. for C$_{25}$H$_{32}$N$_5$ (parent+1): 402.2658. Found: 402.2657.

EXAMPLE 106

9-{2-[4-(6-Amino-pyridin-2-yl)-phenyl]-ethyl}-3-oxa-9-aza-bicyclo[3.3.1]non-7-ylamine Prepared as in Example 1, using N-t-butoxycarbonyl-3-oxa-9-aza-bicyclo[3.3.1]non-7-ylamine in 9.5% yield, followed by removal of the t-butoxycarbonyl group using trifluoroacetic acid in methylene chloride at room temperature in 88% yield, as the hydrochloride salt.

$^1$H-NMR (CDCl$_3$, δ): 1.36 (m, 2H), 2.36 (m, 2H), 2.46 (bs, 2H), 2.70 (m, 4H), 2.81 (m, 2H), 3.14 (m, 1H), 3.68 (m, 2H), 3.87 (m, 2H), 4.51 (bs, 2H), 6.40 (d, J=8, 1H), 7.04 (d, J=7, 1H), 7.23 (m, 2H), 7.45 (t, J=8, 1H), 7.82 (m, 2H). $^{13}$C-NMR (CDCl$_3$, δ): 31.5, 34.5, 42.1, 51.4, 53.9, 69.8, 106.9, 110.7, 126.7, 129.0, 137.6, 138.3, 140.9, 156.0, 158.0. FAB MS (%): 339 (parent+1, 46), 322 (51), 197 (65), 149 (74), 119 (100), 103 (77), 98 (74). Anal. Calc'd. for C$_{20}$H$_{26}$N$_4$O.3HCl.H$_2$O.3/2(C$_4$H$_{10}$O): C, 54.12, H, 8.04, N, 9.71, Found: C, 54.31, H, 7.63, N, 9.37. HRMS Calc'd. for C$_{20}$H$_{27}$N$_4$O (parent+1): 339.2184. Found: 339.2155.

EXAMPLE 107

{2-[4-(6-Amino-pyridin-2-yl)-phenyl]-ethyl}-3-oxa-9-aza-bicyclo[3.3.1]non-7-yl)-amine Prepared as in Example 102, using ammonium formate and palladium-on-carbon in refluxing ethanol in 87% yield, mp 170° C. (dec.) as the hydrochloride salt.

$^1$H-NMR (CDCl$_3$, δ): 1.36 (m, 2H), 2.09 (m, 2H), 2.79 (m, 2H), 2.91 (m, 4H), 3.7–3.9 (m, 5H), 4.56 (bs, 2H), 13.36 (d, J=8, 1H), 7.01 (d, J=7, 1H), 7.23 (m, 2H), 7.42 (t, J=8, 1H), 7.81 (m, 2H). $^{13}$C-NMR (CDCl$_3$, δ): 36.4, 39.2, 47.7, 48.9, 50.5, 71.7, 106.9, 110.6, 126.9, 128.9, 137.7, 138.3, 140.6, 155.9, 158.3. MS (%): 339 (parent+1, 6), 167 (21), 149 (100), 129 (12), 113 (31). Anal. Calc'd. for C$_{20}$H$_{26}$N$_4$O.3HCl.3/2H$_2$O: C, 51.62, H, 7.29, N, 10.94. Found: C, 51.65, H, 7.24, N, 10.95.

EXAMPLE 108

6-{4-[2-(4-Amino-2,6-dimethyl-piperidin-1-yl)-ethyl]-phenyl}-pyridin-2-ylamine (cis diastereomer)

A. N-Benzyl-2,6-dimethylpiperidin-4-one:

To a 500 mL round-bottomed flask equipped with condenser and N$_2$ inlet were added 40 g (0.28 mol) 1,3-acetonedicarboxylic acid, 24.8 g (0.64 mol) acetaldehyde, and 60 mL water. To the resulting mixture was added slowly, 30 mL (0.28 mol) benzylamine over 30 minutes, the pH was adjusted to 4–5, and the reaction stirred overnight at room temperature. After filtration, the reaction pH was adjusted to 10 with 6 N sodium hydroxide, and extracted with ethyl acetate. The organic layer was washed with brine, dried, and evaporated, and the resulting residue chromatographed on silica gel using hexane/ethyl acetate as eluant to afford both isomers:

Trans isomer: 10.1 g (16.5%) oil. $^1$H-NMR (CDCl$_3$, δ): 1.07 (d,J=7, 6H), 2.17 (m, 2H), 2.47 (m, 2H), 3.25 (m, 2H), 3.75 (Ab$_q$, J=14, Dn=110, 2H), 7.23 (m, 1H), 7.29 (m, 2H), 7.37 (m, 2H). $^{13}$C-NMR (CDCl$_3$, δ): 17.4, 47.4, 51.3, 51.8, 126.9, 128.2, 128.3, 140.2, carbonyl carbon not visible in this scan. MS (%): 218 (parent+1, 100). Cis isomer: 3.31 g (5.4%) oil. $^1$H-NMR (CDCl$_3$, δ): 1.13 (d, J=6, 6H), 2.32 (m, 4H), 3.10 (m, 2H), 3.83 (s, 2H), 7.21 (m, 1H), 7.30 (m, 2H), 7.39 (m, 2H). $^{13}$C-NMR (CDCl$_3$, δ): 21.5, 47.1, 50.0, 57.3, 126.5, 127.6, 128.2, 141.0, carbonyl carbon not visible in this scan. MS (%): 218 (parent+1, 100).

B. N-Benzyl-2,6-dimethylpiperidin-4-one methoxime (cis isomer):

To a 100 mL round-bottomed flask equipped with condenser and N$_2$ inlet were added 3.31 g (15.2 mmol) N-benzyl-2,6-dimethylpiperidin-4-one, cis isomer, 2.1 g (24.3 mmol) methoxime hydrochloride, 3.4 mL (24.3 mmol) triethylamine, and 50 mL methanol. The reaction was refluxed 24 h, cooled, and evaporated. The residue was taken up in water/ethyl acetate, and the organic layer seperated, washed with brine, dried, and evaporated. The residue was chromatographed on silica gel using hexane/ethyl acetate to afford 1.5 g (40%) of an oil.

$^1$H-NMR (CDCl$_3$, δ): 1.10 (m, 6H), 1.92 (m, 1H), 2.11 (m, 1H), 2.29 (m, 1H), 2.80 (m, 1H), 2.87 (m, 1H), 2.92 (m, 1H), 3.78 (s, 2H), 3.81 (s, 3H), 7.19 (m, 1H), 7.28 (m, 2H), 7.36 (m, 2H). $^{13}$C-NMR (CDCl$_3$, δ): 16.5, 16.6, 31.6, 37.8, 49.65, 50.6, 52.3, 61.1, 126.7, 128.2, 140.6, 157.3. APCI MS (%): 247 (parent+1, 100), C. N-Benzyl-2,6-dimethylpiperidin-4-amine (cis isomer):

To a 100 mL round-bottomed flask equipped with condenser and N$_2$ inlet were added 1.5 g (6.1 mmol) N-benzyl-2,6-dimethylpiperidin-4-one methoxime (cis isomer), 60 mL dry tetrahydrofuran, and 15 mL (30 mmol) of a 2.0 M solution of borane methyl sulfide in tetrahydrofuran. The reaction was refluxed 24 h, cooled, and the solvent evaporated. The residue was treated with 60 mL ethanol, 1.9 g (18.3 mmol) sodium carbonate, and 1.5 g cesium fluoride. The reaction was refluxed 24 h, cooled, and evaporated. The residue was taken up in water/ethyl acetate, and the organic layer washed with brine, dried over sodium sulfate, and evaporated to afford 1.5 g (100%) of an oil.

$^1$H-NMR (CDCl$_3$, δ): 1.07 (d,J=6, 6H), 1.41 (m, 2H), 1.70 (m, 2H), 2.56 (m, 2H), 2.66 (m, 1H), 3.77 (s, 2H), 7.17 (m, 1H), 7.25 (m, 2H), 7.34 (m, 2H). $^{13}$H-NMR (CDCl$_3$, δ): 11.3, 21.7, 40.8, 44.4, 45.1, 48.5, 50.4, 52.5, 126.4, 128.1, 128.2, 141.2. MS (%): 219 (parent+1,100).

D. N-Benzyl-2,6-dimethylpiperidin-4-amine t-butylcarbamate (cis isomer):

To a 100 mL round=bottomed flask equipped with condenser and N$_2$ inlet were added 1.3 g (6.0 mmol) N-benzyl-2,6-dimethylpiperidin-4-amine (cis isomer), 1.3 g (6.0 mmol) di-t-butyl-dicarbonate, 1.2 mL (8.9 mmol) triethylamine, and 50 mL methylene chloride. The reaction was stirred at room temperature overnight, then washed with aqueous citric acid, water, and brine, dried over sodium sulfate, and evaporated. The residue was chromatographed on silica gel using methylene chloride/ethyl acetate as eluant to afford 1.6 g (84%) of an oil.

$^1$H-NMR (CDCl$_3$, δ): 1.05 (d, J=6, 6H), 1.13 (q, J=12, 2H), 1.42 (s, 9H), 1.87 (m, 2H), 2.59 (m, 2H), 3.5 (bs, 1H), 3.76 (s, 2H), 4.3 (m, 1H), 7.18 (m, 1H), 7.24 (m, 2H), 7.33 (m, 2H). $^{13}$C-NMR (CDCl$_3$, δ): 10.8, 21.6, 28.5, 37.6, 41.7, 44.2, 50.2, 52.7, 79.0, 126.5, 128.1, 128.2, 141.0, 155.3. APCI MS (%): 319 (parent+1, 100), E. 2,6-Dimethylpiperidin-4-amine t-butylcarbamate (cis isomer):

To a 100 mL round-bottomed flask equipped with condenser and N$_2$ inlet were added 1.6 g (5.0 mmol) N-benzyl-2,6-dimethylpiperidin-4-amine t-butylcarbamate (cis isomer), 2.5 g ammonium formate, 250 mg 10% palladium-on-carbon, and 40 mL ethanol. The reaction was refluxed 2 h, cooled, and filtered through Celite with ethanol and methylene chloride. The filtrate was evaporated, the residue was taken up in ethyl acetate/water, the organic layer separated, washed with brine, dried over sodium sulfate, and evaporated to give a low-melting, white solid, 1.09 g (95.5%).

$^1$H-NMR (CDCl$_3$, δ): 0.81 (q, J=11, 2H), 1.06 (d, J=6, 6H), 1.41 (s, 9H), 1.91 (m, 2H), 2.72 (m, 2H), 3.5 (bs, 1H), 4.4 (m, 1H). $^{13}$C-NMR (CDCl$_3$, δ): 19.0, 22.8, 28.3, 37.5, 42.3, 43.7, 44.0, 47.6, 78.9. MS (%): 229 (parent+1, 62), 173 (100).

F2-(2,5-Dimethylpyrrolyl)-6-((4-(4-t-butylcarboxamido-2,6-dimethylpiperidin-1-yl -carboxamido)methyl)phenyl))-pyridine:

To a 100 mL round-bottomed flask equipped with N$_2$ inlet were added 1.3 g (4.4 mmol) 2-(2,5-dimethylpyrrolyl)-6-((4-(carboxymethyl)phenyl))-pyridine, 1.0 g (4.4 mmol) 2,6-dimethylpiperidin-4-amine t -butylcarbamate (cis isomer), 1.7 g (8.8 mmol) N-ethyl-N-3-dimethylaminopropyl -carbodiimide, 2.7 g (22 mmol) 4dimethylaminopyridin, and 25 mL dimethylformamide. The reaction was stirred at room temperature for 24 h, taken up in ethyl acetate/water, and the organic layer seperated, washed with brine, dried over sodium sulfate, and evaporated. The residue was chromatographed on silica gel using hexane/ethyl acetate as eluant to afford 1.8 g (79%) of a foam. $^1$H-NMR (CDCl$_3$, δ): 1.89 (m, 8H), 1.35 (s, 9H), 2.1 (m, 2H), 2.16 (s, 6H), 3.4 (bs, 1H), 3.72 (s, 2H), 4.8 (m, 1H), 5.86 (s, 2H), 7.05 (d,J=8, 1H), 7.28 (m, 2H), 7.68 (d, J=8, 1H), 7.79 (t, J=8, 1H), 7.98 (m, 2H). $^{13}$C-NMR (CDCl$_3$, δ): 13.4, 28.3, 35.6, 41.3, 44.1, 47.0, 60.2, 79.1, 106.9, 118.1, 119.65, 127.1, 128.4, 128.9, 136.7, 138.5, 151.5, 155.0, 156.4, 169.7. APCI MS (%): 517 (parent+1, 65), 461 (100), 417 (32).

G. 2-(2,5-Dimethylpyrrolyl)-6-((4-(4-amino-2,6-dimethylpiperidin-1-yl -carboxamido)methyl)phenyl))-pyridine:

To a 100 mL round-bottomed flask equipped with N$_2$ inlet were added 1.0 g (1.94 mmol) 2-(2,5-dimethylpyrrolyl)-6-((4-(6-t -butylcarboxamido-2,6-dimethylpiperidin-4-yl-carboxamido)methyl)phenyl))-pyridine, 100 mL ethyl acetate, and the solution cooled to 0° C. and saturated with HCl. The reaction was stirred 15 min at room temperature, evaporated, and the residue taken up in 1 N sodium hydroxide solution and extracted with methylene chloride. The organic layer was washed with brine, dried over sodium sulfate, and evaporated to give 770 mg (95.5%) of a foam. $^1$H-NMR (CDCl$_3$, δ): 1.18 (m, 2H), 1.22 (d, J=7, 6H), 1.97 (m, 2H), 2.15 (s, 6H), 2.68 (m, 1H), 3.72 (s, 2H), 4.3 (bs, 2H), 5.86 (s, 2H), 7.06 (d, J=8, 1H), 7.27 (m, 2H), 7.66 (d, J=8, 1H), 7.79 (t, J=8, 1H), 7.97 (m, 2H). $^{13}$C-NMR (CDCl$_3$, δ): 13.4, 24.3, 39.0, 41.6, 44.7, 47.1, 60.2, 106.9, 118.1, 119.7, 127.1, 128.45, 128.9, 136.7, 136.9, 138.5, 151.5, 156.3, 169.7. MS (%): 417 (parent+1, 100).

H. 2-(2,5-Dimethylpyrrolyl)-6-{4-[2-(4-amino-2,6-dimethyl-piperidin-1-yl)-ethyl]-phenyl}-pyridine (cis diastereomer):

To a 100 mL three-necked round-bottomed flask equipped with condenser, septum and N2 inlet were added 640 mg (4.8 mmol) aluminum chloride, 20 mL dry tetrahydrofuran, and after cooling to 0° C., 11.2 mL (11.2 mmol) of a 1.0 M solution of lithium aluminum hydride in tetrahydrofuran. After stirring at 0° C. for 1 h, the reaction was cooled to . 78° C., and a solution of 670 mg (1.6 mmol) 2-(2,5-dimethylpyrrolyl)-6-((4-(4-amino-2,6-dimethylpiperidin-1-yl -carboxamido)methyl)phenyl))-pyridine in 10 mL dry tetrahydrofuran added, and stirring continued at . 78° C. for 1 h. The reaction was then warmed to room temperature and stirred overnight. The reaction was carefully quenched with dilute hydrochloric acid, the pH adjusted to 10 with 6 N sodium hydroxide solution, and extracted with ethyl acetate. The organic layer was washed with brine, dried over sodium sulfate, and evaporated. The residue was chromatographed on silica gel using methanol/methylene chloride as eluant to give 423 mg (66%) of an oil. $^1$H-NMR (CDCl$_3$, δ): 1.17 (m, 2H), 1.22 (d, J=6, 6H), 1.81 (m, 2H), 1.95 (bs, 2H), 2.19 (s, 6H), 2.70 (m, 5H), 2.99 (m, 2H), 5.90 (s, 2H), 7.08 (d, J=8, 1H), 7.22 (m, 2H), 7.68 (d, J=8, 1H), 7.81 (t, J=8, 1H), 7.97 (m, 2H). $^{13}$C-NMR (CDCl$_3$, δ): 13.4, 21.0, 45.1, 48.1, 48.6, 49.4, 49.9, 53.4, 106.9, 117.9, 119.5, 127.0, 158.5, 158.9, 136.1, 138.5, 142.2, 151.5, 156.6. MS (%): 403 (parent+1, 100).

I. 6-{4-[2-(4-Amino-2,6-dimethyl-piperidin-1-yl)-ethyl]-phenyl}-pyridin-2-ylamine (cis diastereomer):

The deblocking was carried out using hydroxylamine hydrochloride as described in Example 124 F to afford the product as an oil in 100% yield, which was converted to the hydrochloride salt as an amorphous solid. $^1$H-NMR (CDCl$_3$, δ): 1.06 (m, 2H), 1.18 (d, J=6, 6H), 1.75 (m, 2H), 2.63 (m, 5H), 2.95 (m, 2H), 4.58 (bs, 2H), 6.35 (d, J=8, 1H), 6.99 (d, J=8, 1H), 7.15 (m, 2H), 7.40 (t, J=8, 1H), 7.79 (m, 2H). $^{13}$C-NMR (CDCl$_3$, δ): 21.0, 45.3, 48.1, 48.6, 49.4, 53.4, 106.8, 110.5, 126.8, 128.6, 137.4, 138.2, 141.1, 155.8, 158.2. FAB MS (%): 325 (parent+1, 18), 149 (69), 119 (100). HRMS Calc'd. for C$_{20}$H$_{29}$N$_4$ (parent+1): 325.2392. Found: 325.2369.

EXAMPLE 109

6-{4-[2-(4-Methyl-piperazin-1-yl)-ethyl]-phenyl}-pyridin-2-ylamine

Prepared as in Example 1, using N-methylpiperazine in 74% yield, mp 170° C. (dec.) as the hydrochloride salt.

$^1$H-NMR (CDCl$_3$, δ): 2.26 (s, 3H), 2.4–2.6 (broad multiplet, 8H), 2.60 (m, 2H), 2.80 (m, 2H), 4.56 (bs, 2H), 6.35 (d, J=8, 1H), 7.00 (d, J=7, 1H), 7.23 (m, 2H), 7.41 (t, J=8, 1H), 7.80 (m, 2H). $^{13}$C-NMR (CDCl$_3$, δ): 33.3, 46.1, 53.1, 55.1, 60.3, 106.8, 110.6, 126.8, 128.9, 137.6, 138.3, 140.8, 156.0, 158.3. FAB MS (%): 297 (parent+1, 100), 197 (28), 113 (73). Anal. Calc'd. for C$_{18}$H$_{24}$N$_4$.3HCl.1/2H$_2$O: C, 52.12, H, 6.80, N, 13.51. Found: C, 52.05, H, 7.00, N, 13.07.

EXAMPLE 110

6-{4-[2-(4-Benzenesulfonyl-piperazin-1-yl)-ethyl]-phenyl}-pyridin-2-ylamine

Prepared as in Example 1, using N-benzenesulfonylpiperazine in 93% yield, as the hydrochloride salt.

$^1$H-NMR (CDCl$_3$, δ): 2.60 (m, 6H), 2.74 (m, 2H), 3.04 (m, 4H), 4.64 (bs, 2H), 6.44 (d, J=8, 1H), 7.03 (d, J=t, 1H), 7.20 (m, 2H), 7.48 (t, J=8, 1H), 7.52 (m, 3H), 7.73 (m, 2H), 7.81 (m, 2H). $^{13}$C-NMR (CDCl$_3$, δ): 33.0, 45.8, 51.9, 59.4, 106.9, 110.4, 126.7, 127.6, 128.6, 128.8, 132.6, 135.0, 133.4, 140.0, 156.0, 158.0. FAB MS (%): 423 (parent+1, 25), 167 (25), 149 (100), 113 (22). Anal. Calc'd. for C23H$_{26}$N$_4$O$_2$S.2HCl.5/4H$_2$O: C, 53.33, H, 5.94, N, 10.82. Found: C, 53.33, H, 5.92, N, 10.45.

EXAMPLE 111

6-{4-[2-(4-Methanesulfonyl-piperazin-1-yl)-ethyl]-phenyl}-pyridin-2-ylamine

Prepared as in Example 1, using N-methanesulfonylpiperazine in 15% yield, as the hydrochloride salt.

$^1$H-NMR (CDCl$_3$, δ): 2.61 (m, 4H), 2.65 (m, 2H), 2.76 (s, 3H), 2.80 (m, 2H), 3.23 (m, 4H), 4.49 (bs, 2H), 6.42 (d, J=8, 1H), 7.04 (d, J=7, 1H), 7.23 (m, 2H), 7.46 (t, J=8, 1H), 7.83 (m, 2H). $^{13}$C-NMR (CDCl$_3$, δ): 33.1, 33.9, 45.8, 52.2, 59.6, 106.9, 110.6, 126.8, 128.8, 137.6, 138.3, 140.3, 155.8, 158.1. MS (%): 361 (parent+1, 17), 149 (100), 135 (54), 119 (89), 103 (48). Anal. Calc'd. for C$_{18}$H$_{24}$N$_4$O$_2$S.2HCl: C, 49.88, H, 6.05, N, 12.93. Found: C, 50.11, H, 6.08, N, 11.69.

EXAMPLE 112

6-{4-[2-(2,6-Dimethyl-piperazin-1-yl)-ethyl]-phenyl}-pyridin-2-ylamine: Refer to Scheme 2
A. 2-(2,5-Dimethylpyrrolyl)-6-(4-formylphenyl)-pyridine:

To a 1 L round-bottomed flask equipped with condenser and N$_2$ inlet were added 20.0 g (79.6 mmol) 6-bromo-2-(2,5-dimethylpyrrolyl)-pyridine, 11.9 g (79.6 mmol) 4-formylphenyl boronic acid, 33.8 g (300 mmol) sodium carbonate, 1 g (0.8 mmol) tetrakis-triphenylphosphine palladium, 370 mL ethanol, and 40 mL water. The mixture was refluxed 16 h, cooled, poured into water, and extracted into ethyl acetate. The organic layer was washed with brine, dried over sodium sulfate, and evaporated. The residue was chromatographed on silica gel using hexane/ethyl acetate as eluant to afford 21.0 g (95.5%) of a light yellow, solid, mp 106–108° C.

$^1$H-NMR (CDCl$_3$, δ): 2.21 (s, 6H), 5.94 (s, 2H), 7.22 (d, J=8, 1H), 7.82 (d, J=8, 1H), 7.93 (t, J=8, 1H), 7.98 (m, 2H), 8.22 (m, 2H), 10.07 (s, 1H).
$^{13}$C-NMR (CDCl$_3$, δ): 13.4, 107.2, 119.0, 120.9, 127.4, 128.6, 130.1, 136.6, 138.8, 155.2, 191.9.
APCI MS (%): 277 (parent+1, 100).
B. 2-(2,5-Dimethylpyrrolyl)-6-(4-(cyanomethyl)phenyl)-pyridine:

To a 2 L round-bottomed flask equipped with condenser and N$_2$ inlet were added 17.1 g (152 mmol) potassium t-butoxide and 250 mL dry 1,2-dimethoxyethane (DME). The reaction was cooled to −60° C., and a solution of 16.2 g (83 mmol) tosylmethylisocyanide in 250 mL DME added dropwise over 5 minutes. After stirring for 5 minutes, a solution of 21.0 g (76 mmol) 2-(2,5-dimethylpyrrolyl)-6-(4-formylphenyl)-pyridine in 500 mL DME was added dropwise over 10 minutes, and stirring continued at −60° C. for 1 h. Then 250 mL methanol was added, and the reaction warmed to room temperature, then refluxed 20 minutes. The reaction was cooled, evaporated, taken up in wIater and 8 mL acetic acid, and extracted with methylene chloride. The organic layer was washed with brine, dried over sodium sulfate, and evaporated. The residue was chromatographed with hexane/methylene chloride on silica gel to give 16.8 g (77%) of a low-melting solid.

$^1$H-NMR (CDCl$_3$, δ): 2.21 (s, 6H), 3.80 (s, 2H), 5.93 (s, 2H), 7.16 (d, J=8, 1H), 7.42 (m, 2H), 7.74 (d, J=8, 1H), 7.89 (t, J=8, 1H), 8.08 (m, 2H).
APCI MS (%): 287 (parent+1, 100).
C. 2-(2,5-Dimethylpyrrolyl)-6-(4-(carboxymethyl)phenyl)-pyridine:

To a 2 L round-bottomed flask equipped with condenser and N$_2$ inlet were added 16.8 g (58.5 mmol) 2-(2,5-dimethylpyrrolyl)-6-(4-(cyanomethyl)phenyl)-pyridine and 500 mL ethanol. The reaction was heated to reflux, and 1400 mL of a 10% aqueous sodium hydroxide solution added dropwise over 2 h. The reaction was refluxed an additional 2 h, cooled, and evaporated to a small volume, then the pH adjusted to 1 with concentrated hydrochloric acid (ice-cooling), and extracted into ethyl acetate. The organic layer was washed with biine, dried over sodium sulfate, and evaporated to a light yellow, low-melting solid, 16.9 g (94%).

$^1$H-NMR (CDCl$_3$, δ): 2.20 (s, 6H), 3.69 (s, 2H), 5.92 (s, 2H), 7.13 (d, J=8, 1H), 7.37 (m, 2H), 7.72 (d, J=8, 1H), 7.86 (t, J=8, 1H), 8.03 (m, 2H). $^{13}$C-NMR (CDCl$_3$, δ): 13.4, 40.7, 106.9, 118.2, 119.9, 127.1, 128.6, 129.8, 134.5, 137.4, 138.6, 151.6, 156.3, 177.4. APCI MS (%): 307 (parent+1, 100).
D. 2-(2,5-Dimethylpyrrolyl)-6-(4-((2,6-dimethyl-4-t-butoxycarbonyl)piperazin-1-yl)methyl)phenyl)-pyridine:

To a 100 mL round-bottomed flask equipped with N$_2$ inlet were added 500 mg (1.6 mmol) 2-(2,5-dimethylpyrrolyl)-6-(4-(carboxymethyl)phenyl)-pyridine, 350 mg (1.6 mmol) 2,6-dimethyl-4-t-butoxycarbonyl-piperazine, 626 mg (3.2 mmol) N-ethyl-N-3-dimethylaminopropyl-carbodiimide, 996 mg (8.1 mmol) 4-dimethylamino-pyridine, and 10 mL dry dimethylformamide. The reaction was stirred at room temperature for 16 h, poured into water, and extracted into ethyl acetate. The organic layer was washed with water and brine, dried over sodium sulfate, and evaporated. The residue was chromatographed on solica gel using methanol/methylene chloride as eluant to afford 817 mg (100%) of a foam.

$^1$H-NMR (CDCl$_3$, δ): 1.23 (d, J=7, 6H), 1.44 (s, 9H), 2.19 (s, 6H), 2.8 (m, 4H), 3.76 (m, 2H), 4.0 (m, 2H), 5.91 (s, 2H), 7.12 (d, J=8, 1H), 7.33 (m, 2H), 7.72 (d, J=8, 1H), 7.85 (t, J=8, 1H), 8.01 (m, 2H). $^{13}$C-NMR (CDCl$_3$, δ): 13.4, 19.8, 21.0, 28.2, 40.8, 44.8, 46.9, 48.1, 48.9, 79.9, 106.9, 118.1, 119.7, 127.2, 128.5, 128.9, 136.4, 136.9, 138.5, 151.6, 155.2, 156.3, 169.8. APCI MS (%): 503 (parent+1, 40), 447 (100), 403 (55).

E. 6-(4-((2,6-Dimethyl)piperazin-1-yl)methyl)phenyl)-pyridin-2-yl amine:

2-(2,5-Dimethylpyrrolyl)-6-(4-((2,6-dimethyl-4-t-butoxycarbonyl)piperazin-1-yl)methyl)phenyl)-pyridine was deblocked first with hydroxylamine hydrochloride as described in Example 1F, then with trifluoroacetic acid in methylene chloride as described in Example 2 to afford 455 mg (88% overall) of a foam.

$^1$H-NMR (CDCl$_3$, δ): 1.28 (d, J=7, 6H), 2.8 (m, 4H), 3.74 (s, 2H), 4.55 (m, 2H), 6.43 (d, J=8, 1H), 7.05 (d, J=8, 1H), 7.30 (m, 2H), 7.47 (t, J=8, 1H), 7.86 (m, 2H). $^{13}$C-NMR (CDCl$_3$, δ): 40.5, 44.0, 48.2, 50.1, 107.2, 110.4, 126.9, 128.7, 135.7, 138.0, 138.3, 155.3, 158.4, 170.0. IR (KBr, cm.$^{-1}$): 1620 (C=O). APCI MS (%): 325 (parent+1, 100).

F. 6-{4-[2-(2,6-Dimethyl-piperazin-1-yl)ethyl]-phenyl}-pyridin-2-ylamine:

6-(4-((2,6-Dimethyl)piperazin-1-yl)methyl)phenyl)-pyridin-2-yl amine was reduced with borane methyl sulfide as described in Example 124B to give an 8% yield of a hygroscopic solid as the hydrochiloride salt.

$^1$H-NMR (CDCl$_3$, δ): 1.13 (d, 6H), 2.53 (m, 2H), 2.68 (m, 4H), 2.90 (m, 2H), 3.00 (m, 2H), 4.49 (bs, 2H), 6.42 (d, J=8, 1H), 7.04 (d, J=7, 1H), 7.19 (m, 2H), 7.46 (t, J=8, 1H), 7.82 (m, 2H). $^{13}$C-NMR (CDCl$_3$, δ): 17.6, 28.7, 49.8, 53.6, 54.2, 106.8, 110.6, 126.9, 128.6, 137.5, 138.3, 141.1, 155.9, 158.1. MS (%): 311 (parent+1, 14), 167 (23), 149 (100). HRMS Calc'd. for C$_{19}$H$_{27}$N$_4$: 311.2236. Found: 311.2236.

EXAMPLE 113

6-{4-[2-(2,6-Dimethyl-4-methylamino-piperidin-1-yl)-ethyl]-phenyl}-pyridin-2-ylamine Prepared as in Example 112, using 4-t-butoxycarbonylamino-2,6-dimethylpiperidine coupling with 2-(2,5-dimethylpyrrolyl)-6-(4-(carboxymethyl)phenyl)-pyridin in 75% yield, followed by reduction with borane methyl sulfide in refluxing tetrahydrofuran in 17% yield, followed by deprotection using hydroxylamine hydrochloride in refluxing ethanol in 85% yield, as a hygroscopic solid as the hydrochloride salt.

$^1$H-NMR (CDCl$_3$, δ): 1.06 (m, 6H), 1.23 (m, 2H), 1.81 (m, 2H), 2.43 (s, 3H), 2.53 (m, 1H), 2.7–2.9 (m, 6H), 4.51 (bs, 2H), 6.41 (d, J=8, 1H), 7.03 (d, J=7, 1H), 7.24 (m, 2H), 7.45 (t, J=8, 1H), 7.82 (m, 2H). $^{13}$C-NMR (CDCl$_3$, δ): 11.4, 21.3, 32.4, 35.4, 36.6, 40.1, 48.7, 50.8, 51.1, 52.0, 106.9, 110.7, 126.8, 129.0, 137.5, 138.3, 141.3, 156.1, 158.2. APCI MS (%): 339 (parent+1, 100). Anal. Calc'd. for C$_{21}$H$_{30}$N$_4$.3HCl.1/2CH$_2$Cl$_2$.9/4(C$_4$H$_{10}$O): C, 55.75, H, 8.67, N, 8.53. Found: C, 55.66, H, 8.21, N, 8.02.

EXAMPLE 114

6-{4-[2-(4-cyclohexyl-piperazin-1-yl)-ethyl]-phenyl}-pyridin-2-ylamine

Prepared as in Example 112, using N-cyclohexylpiperazine coupling with 2-(2,5-dimethylpyrrolyl)-6-(4-(carboxymethyl)phenyl)-pyridine in 100% yield followed by reduction using borane methyl sulfide in refluxing tetrahydrofuran in 97% yield, then deprotection using hydroxylamine hydrochloride in refluxing ethanol in 98% yield, as the hydrochloride salt.

$^1$H-NMR (CDCl$_3$, δ): 1.09 (m, 6H), 1.75 (m, 2H), 1.88 (m, 2H), 2.24 (m, 1H), 2.59 (m, 10H), 2.83 (m, 2H), 4.53 (bs, 2H), 6.38 (d, J=8, 1H), 7.02 (d, J=8, 1H), 7.22 (m, 2H), 7.43 (t, J=8, 1H), 7.81 (m, 2H). $^{13}$C-NMR (CDCl$_3$, δ): 25.5, 25.9, 28.5, 33.0, 48.5, 53.2, 60.0, 63.1, 106.5, 110.3, 126.4, 128.5, 137.2, 137.9, 140.5, 155.6, 157.8. APCI MS (%): 365 (parent+1, 100). Anal. Calc'd. for C$_{23}$H$_{32}$N$_4$.3HCl.1/4H$_2$O.1/4(C$_4$H$_{10}$O).1/4CH$_2$Cl$_2$: C, 56.21, H, 7.49, N, 10.81. Found: C, 56.12, H, 7.83, N, 10.44.

EXAMPLE 115

6-{4-[2-(Adamantan-1-ylamino)-ethyl]-phenyl}-pyridin-2-ylamine

Preparedas in Example 112, using 1-aminoadamantane for the coupling with 2-(2,5-dimethylpyrrolyl)-6-(4-(carboxymethyl)phenyl)-pyridine followed by deblocking with hydroxylamine hydrochloride and borane methyl sulfide reduction in 89.5% yield, mp 200–220° C. (dec.) as the hydrochloride salt.

$^1$H-NMR (CDCl$_3$, δ): 1.58 (bs, 12H), 2.02 (bs, 3H), 2.80 (m, 2H), 2.85 (m, 2H), 4.54 (bs, 2H), 6.40 (d, J=8, 1H), 7.03 (d, J=7, 1H), 7.25 (m, 2H), 7.45 (t, J=8, 1H), 7.83 (m, 2H). $^{13}$C-NMR (CDCl$_3$, δ): 29.6, 36.7, 36.8, 41.7, 42.6, 50.5, 106.9, 110.7, 126.9, 128.9, 137.7, 138.3, 140.7, 156.0, 158.3. FAB MS (%): 348 (parent+1, 44), 135 (100). Anal. Calc'd. for C$_{23}$H$_{29}$N$_3$.2HCl.3/2H$_2$O.1/2(C$_4$H$_{10}$O): C, 61.98, H, 8.11, N, 8.67. Found: C, 61.95, H, 7.90, N, 8.69.

EXAMPLE 116

6-{4-[2-(Adamantan-2-ylamino)-ethyl]-phenyl}-pyridin-2-ylamine

Prepared as in Example 112, using 2-aminoadamantane for the coupling with 2-(2,5-dimethylpyrrolyl)-6-(4-(carboxymethyl)phenyl)-pyridine followed by deblocking with hydroxylamine hydrochloride and borane methyl sulfide reduction in 98% yield, mp 215–230° C. (dec.) as the hydrochloride salt.

$^1$H-NMR (CDCl$_3$, δ): 1.43 (m, 2H), 1.67 (bs, 4H), 1.81 (m, 8H), 2.72 (bs, 1H), 2.85 (m, 4H), 4.53 (bs, 2H), 6.40 (d, J=8, 1H), 7.04 (d, J=7, 1H), 7.26 (m, 2H), 7.45 (t, J=8, 1H), 7.83 (m, 2H). $^{13}$C-NMR (CDCl$_3$, δ): 27.5, 27.8, 31.3, 32.0, 37.6, 37.9, 48.1, 106.8, 110.7, 126.8, 128.9, 137.6, 138.3, 141.0, 156.1, 158.2. FAB MS (%): 348 (parent+1, 80), 135 (100). Anal. Calc'd. for C$_{23}$H$_{29}$N$_3$.2HCl.7/4H$_2$O.3/4(C$_4$H$_{10}$O): C, 61.53, H, 8.34, N, 8.28. Found: C, 61.55, H, 8.12, N, 8.01.

EXAMPLE 117

6-{4-[2-(Indan-2-ylamino)-ethyl]-phenyl}-pyridin-2-ylamine

A. 6-(4-(2-Aminoethyl)phenyl-2-(2,5-dimethylpyrrolyl)pyridine:

To a 250 mL round-bottomed flask equipped with condenser and N2 inlet were added 3.04 g (10.59 mmol) 6-(4-(cyanomethyl)phenyl-2-(2,5-dimethylpyrrolyl) pyridine, 100 mL dry tetrahydrofuran, and 53 mL (53 mmol) of a 1.0 M solution of lithium aluminum hydride in tetrahydrofuran. The reaction was refluxed 40 h, with 20 mL lithium aluminum hydride reagent solution added after 24 h, cooled, and quenched carefully with water. The mixture was taken up in 0.5 N aqueous sodium hydroxide solution and ethyl acetate, and the organic layer was washed with water, then extracted with hydrochloric acid. The aqueous layer was washed with water, then adjusted to pH 10 with aqueous sodium hydroxide solution and extracted with ethyl acetate. The organic layer was washed with brine, dried over sodium sulfate, and evaporated to an oil, 1.37 g (43%), which was used without further purification.

$^1$H-NMR (d, CDCl$_3$): 1.6 (broad, 2H), 2.20 (s, 6H), 2.80 (m, 2H), 2.99 (m, 2H), 5.91 (s, 2H), 7.10 (d, J=8, 1H), 7.28 (m, 2H), 7.70 (m, 1H), 7.84 (m, 1H), 7.98 (m, 2H). MS (APCI) (%): 292 (100, parent+1).

B. 6-{4-[2-(Indan-2-ylamino)-ethyl]-phenyl}-pyridin-2-ylamine:

Prepared from the above oil by reductive amination with 2-indanone using sodium cyanoborohydride in methanol at room temperature in 17% yield, followed by deblocking with hydroxylamine hydrochloride in refluxing ethanol in 82.5% yield, mp 60–70° C. (dec.) as the hydrochloride salt.

$^1$H-NMR (CDCl$_3$, δ): 2.72 (AB pattern, 2H), 2.91 (ddd, J=6.6, 7, 38, 4H), 3.14 (AB pattern, 2H), 3.64 (quintet, J=7, 1H), 4.56 (bs, 2H), 6.40 (dd, J=0.4, 8, 1H), 7.04 (dd, J=0.6, 7, 1H), 7.15 (m, 4H), 7.27 (m, 2H), 7.46 (dt, J=0.4, 8, 1H), 7.85 (m, 2H). $^{13}$C-NMR (CDCl$_3$, δ): 36.1, 39.9, 49.4, 59.5, 107.0, 110.8, 124.7, 126.4, 127,0, 128.9, 137.8, 138.4, 140.4, 141.5, 156.0, 158.3. FAB MS (%): 330 (parent+1, 100), 197 (42), 132, (43), 117 (80). Anal. Calc'd. for C$_{22}$H$_{23}$N$_3$.2HCl.2H$_2$O: C, 60.27, H, 6.67, N, 9.58. Found: C, 60.35, H, 6.48, N, 10.00.

EXAMPLE 118

6-(4-(2-Aminoethyl)phenyl-pyridin-2-ylamine

Prepared by deblocking Example 117A above using hydroxylamine hydrochloride in refluxing ethanol in 56% yield, mp 73–83° C. (dec.) as the hydrochlo,ride salt.

$^1$H-NMR (DMSO-d$_6$, δ): 2.95 (m, 2H), 3.02 (m, 2H), 4.0 (bs, 4H), 6.96 (d, J=9, 1H), 7.21 (d, J=7, 1H), 7.45 (m, 2H), 7.8–8.0 (m, 3H). $^{13}$C-NMR (DMSO-d$_6$, δ): 25.4, 32.8, 40.4, 67.8, 110.0, 111.8, 127.5, 129.9, 140.3, 143.8, 146,3, 155.3. FAB MS (%): 214(parent+1, 54), 135 (49), 119 (100), 103 (49). HRMS Calc'd. for C$_{13}$H$_{16}$N$_3$ (parent+1): 214.1344. Found: 214.1351.

EXAMPLE 119

6-{4-[2-(Bis-pyridin-3-ylmethyl-amino)-ethyl]-phenyl}-pyridin-2-ylamine

Prepared from Example 117A by reductive amination with pyridine-3-carboxaldehyde using sodium cyanoborohydride in methanol followed by deblocking using hydroxylamine hydrochloride in refluxing ethanol in 63% yield as a hygroscopic solid as the hydrochloride salt.

$^1$H-NMR (CDCl$_3$, δ): 2.72 (m, 2H), 2.83 (m, 2H), 3.61 (s, 4H), 6.46 (d, J=8, 1H), 6.97 (d, J=7, 1H), 7.09 (m, 2H), 7.17 (m, 2H), 7.47 (t, J=8, 1H), 7.54 (m, 2H), 7.74 (m, 2H), 8.41 (m, 4H). $^{13}$C-NMR (CDCl$_3$, δ): 29.7, 53.4, 54.9, 107.7, 110.6, 123.6, 126.9, 129.0, 134.8, 136.6, 139.1, 140.9, 148.3, 149.6, 154.8, 158.0. MS (%): 396 (parent+1, 100). HRMS Calc'd. for C$_{25}$H$_{26}$N$_5$ (parent+1): C, 396.2188. Found: 396.2155.

EXAMPLE 120

6-{4-[2-(Bis-pyridin-4-ylmethyl-amino)-ethyl]-phenyl}-pyridin-2-ylamine

Prepared as in Example 119, using pyridine-4-carboxaldehyde, in 75% yield, mp 150–163° C. (dec.) as the hydrochloride salt.

$^1$H-NMR (CDCl$_3$, δ): 2.70 (m, 2H), 2.81 (m, 2H), 3.60 (s, 4H), 6.42 (d, J=8, 1H), 7.03 (d, J=7, 1H), 7.06 (m, 2H), 7.16 (m, 4H), 7.46 (t, J=8, 1H), 7.81 (m, 2H), 8.46 (m, 4H). $^{13}$C-NMR (CDCl$_3$, δ): 33.4, 55.4, 57.3, 107.0, 110.6, 123.3, 126.7, 128.9, 137.7, 138.3, 140.3, 148.4, 149.7, 155.7, 158.2. MS (%): 396 (parent+1, 100). HRMS. Calc'd. for C$_{25}$H$_{26}$N$_5$ (parent+1): C, 396.2188. Found: 396.2152.

EXAMPLE 121

N-{2-[4-(6-Amino-pyridin-2-yl)-phenyl]-ethyl}-N-(1-benzyl-piperidin-4-yl)-acetamide Prepared as in Example 117, using N-benzyl-4-piperidone with sodium cyanoborohydride in methanol, followed by acetylation with acetyl chloride and triethylamine in methylene chloride, followed by deblocking with hydroxylamine hydrochloride in refluxing ethanol in 44% yield, mp 60–70° C. (dec.) as the hydrochloride salt.

$^1$H-NMR (CDCl$_3$, δ): 1.8–1.9 (m, 4H), 2.12 (s, 3H), 2.84 (m, 2H), 2.96 (m, 2H), 3.40 (m, 4H), 3.50 (s, 2H), 4.59 (bs, 2H), 6.42 (t, J=8, 1H), 7.02 (d, J=7, 1H), 7.2–7.4 (m, 7H), 7.45 (dt, J=7,8, 1H), 7.82 (m, 2H). $^{13}$C-NMR (CDCl$_3$, δ): 14.2, 14.7, 22.1, 22.2, 30.0, 30.8, 35.5, 37.6, 43.8, 46.0, 53.0, 53.1, 62.9, 63.0, 107.1, 107.2, 110.8, 126.9, 128.1, 128.2, 128.7, 128.9, 129.2, 129.3, 137.0, 137.7, 137.8, 138.3, 138.4, 138.6, 140.2, 155.7, 156.1, 158.2, 158.3, 170.2, 170.7. FAB MS (%): 429 (parent+1, 44), 91 (100). HRMS Calc'd. for C$_{27}$H$_{33}$N$_4$O (parent+1): C, 429.2654. Found: 429.2669.

EXAMPLE 122

6-[4-(4-Methyl-piperazin-1-ylmethyl)-phenyl]-pyridin-2-ylamine

Prepared from (6-(4-formylphenyl)2-(2,5-dimethylpyrrolyl)-pyridine (Example 112), using N-methylpiperazine with sodium cyanoborohydride in methanol in 43% yield, followed by deblocking using hydroxylamine hydrochloride in refluxing ethanol in 78% yield, mp 240–250° C. (dec.) as the hydrochloride salt.

$^1$H-NMR (CDCl$_3$, δ): 2.24 (s, 3H), 2.4–2.5 (m, 8H), 3.49 (s, 2H), 4.66 (bs, 2H), 6.36 (d, J=8, 1H), 7.00 (d, J=7, 1H), 7.34 (m, 2H), 7.41 (t, J=8, 1H), 7.81 (m, 2H). $^{13}$C-NMR (CDCl$_3$, δ): 46.0, 53.0, 55.1, 62.7, 107.0, 110.7, 126.7, 129.4, 138.3, 138.6, 156.0, 158.4. FAB MS (%): 283 (parent+1, 82), 244 (45), 183 (100). Anal. Calc'd. for C$_{17}$H$_{22}$N$_4$.3HCl.2H$_2$O: C, 47.73, H, 6.83, N, 13.10. Found: C, 47.85, H, 6.78, N, 12.92.

EXAMPLE 123

3-[4-(6-Amino-pyridin-2-yl)-benzyl]-3-aza-bicyclo[3.1.0]hex-6-ylamine

Prepared as in Example 122, using 6-(t-butoxycarbonylamino)-3-aza-bicyclo[3.1.0]hexane in the reductive amination in 66% yield, and in 75% yield for the deblocking which included trifluoroacetic acid in methylene chloride to remove the t-butoxycarbonyl group, mp 189–192° C. (dec.) as the hydrochloride salt.

$^1$H-NMR (CDCl$_3$, δ): 1.28 (bs, 2H), 2.34 (m, 2H), 2.51 (bs, 1H), 2.85 (m, 2H), 3.48 (s, 2H), 3.61 (bs), 6.38 (d, J=8, 1H), 6.90 (d, J=7, 1H), 7.23 (m, 2H), 7.39 (t, J=8, 1H), 7.66 (m, 2H). $^{13}$C-NMR (MeOD$_4$, δ): 25.2, 32.1, 54.4, 58.9, 107.3, 110.9, 126.7, 128.8, 138.4, 138.5, 139.4, 156.0, 158.5. FAB MS (%): 281 (parent+1, 97), 212 (30), 183 (100). Anal. Calc'd. for C$_{17}$H$_{19}$N$_4$.3HCl.1/2H$_2$O: C, 70.56, H, 7.31, N, 19.36. Found: C, 70.76, H, 7.15, N, 19.17.

EXAMPLE 124

6-{4-[2-(Bis-cyclohexylmethyl-amino)-ethyl]-phenyl}-pyridin-2-ylamine Refer to Scheme 2

A. N,N-Dibenzyl(4-bromophenyl)acetamide:

To a 100 mL round-bottomed flask equipped with $N_2$ inlet were addied 1.075 g (5 mmol) 4-bromophenylacetic acid, 0.961 mL (5 mmol) dibenzylamine, 20 mL dry acetonitrile, 10 mg 1-hydroxybenzotriazole, 959 mg (5 mmol) EDAC, and 1.74 mL (12.5 mmol) triethylamine. The reaction was stirred at room temperature for 36 hr, poured into aqueous sodium bicarbonate solution, and extracted into ethyl acetate. The organic layer was washed with water aqueous citrate, water, and brine, dried over sodium sulfate, and evaporated to give 2.0 g (100%) of an oil which was used directly.

$^1$H-NMR (CDCl$_3$, δ): 3.705 (s, 2H), 4.43 (s, 2H), 4.61 (s, 2H), 7.1–7.4 (m, 14H). $^{13}$C-NMR (CDCl$_3$, δ): 40.1, 48.5, 50.2, 120.9, 126.3, 127.5, 127.8, 128.3, 128.6, 129.1, 130.7, 130.8, 131.7, 134.0, 136.2, 137.1, 171.1. MS (%): 393/395 (parent+1, 98/100).

B. N,N-Dibenzyl-2-(4-bromophenyl)ethaneamine:

To a 100 mL round-bottomed flask equipped with condenser and N2 inlet were added the above oil (5 mmol), 25 mL dry tetrahydrofuran, and 7.5 mL (15 mmol) of a 2.0M solution of borane methyl sulfide in tetrahydrofuran. The reaction was refluxed 18 hr, cooled, and evaporated. The residue wais taken up in 25 mL ethanol, and treated with 1 g sodium carbonate and 1 g cesium fluoride, then refluxed 18 hr. The reaction was cooled, evaporated, and the residue taken up in water/ethyl acetate. The organic layer was separated, washed with water and brine, dried over sodium sulfate, and evaporated. The resulting oil (175 g, 92%) was used directly.

$^1$H-NMR (CDCl$_3$, δ): 2.70 (m, 2H), 2.75 (m, 2H), 3.65 (s, 4H), 6.95 (d, J=8, 1H), 7.2–7.4 (m, 13H). $^{13}$C-NMR (CDCl$_3$, δ): 33.0, 54.8, 58.3, 119.6, 126.9, 128.2, 128.7, 130.7, 131.2, 139.563, 139.635. MS (%): 380/382 (parent+1, 95/100).

C. 2-(2,5-Dimethylpyrrol-1-yl)-6-(4-(2-(N,N-dibenzylamino)ethyl)phenyl)-pyridine:

To a 100 mL three-necked round-bottomed flask equipped with septum and N2 inlet were added 1.75 g (4.60 mmol) of N,N-dibenzyl-2-(4-bromophenyl)ethaneamine and 16 mL dry ether. The solution was cooled to −70° C., and 3.45 mL of a 1.6 M solution (5.53 mmol) of butyl lithium in hexanes added dropwise over 5 min. The reaction was stirred 5 min at −70° C., then warmed to room temperature, and a solution of 0.950 g (5.53 mmol) 2-(2,5-dimethylpyrrol-1-yl)-pyridine in 5 mL dry ether added over 3 min. The reaction turned to dark orange and then dark red as it was stirred at room temperature for 6 hr, then quenched with aqueous ammonium chloride. The organic layer was diluted with ethyl acetate and separated, washed with aqueous ammonium chloride and brine, dried over sodium sulfate for 14 hr in the air (to permit air oxidation to the pyridine) and evaporated. The residue was chromatographied on silica gel using 10% ethyl acetate in hexane as eluant to afford the product as an oil, 860 mg (40%).

$^1$H-NMR (CDCl$_3$, δ): 2.45 (s, 6H), 2.94 (m, 2H), 3.04 (m, 2H), 3.84 (s, 4H), 6.18 (s, 2H), 7.24 (d, J=8, 1H), 7.3–7.5 (m, 12H), 7.83 (d, J=8, 1H), 7.92 (t, J=8, 1H), 8.17 (m, 2H). $^{13}$C-NMR (CDCl$_3$, δ): 13.8, 33.5, 55.1, 58.5, 107.3, 118.2, 119.7, 127.0, 128.4, 128.8, 128.9, 129.1, 129.5, 138.7, 139.85, 142.4, 151.8, 157.0. MS (%): 472 (parent+1, 100).

D. 2-(2,5-Dimethylpyrrol-1-yl)-6-(4-(2-aminoethyl)phenyl)-pyridine:

To a 100 mL three-necked round-bottomed flask equipped with septum and N2 inlet were added 860 mg (1.826 inmol) 2-(2,5-dimethylpyrrol-1-yl)-6-(4-(2-(N,N-dibenzylamino)ethyl)phenyl)-pyridine, 576 mg (9.13 mmol, 5 eq.) ammonium formate, 20 mL ethanol, and 100 mg 10% Pd-C. The reaction was refluxed 2 hr, and additional portion of ammonium formate and palladium added, and refluxing continued another 1 hr. The icooled reaction was filtered through Celite using ethanol and methylene chloride, and the filtrate evaporated. The residue was taken up in aqueous sodium bicarbonate solution and ethyl acetate, the aqueous layer reextracted with ethyl acetate, and the organic layer separated and washed with brine, dried over sodium sulfate, and evaporated. The crude oil, 430 mg (81%) was used directly.

$^1$H-NMR (CDCl$_3$, δ): 2.20 (s, 6H), 2.4 (bs, 2H), 2.80 (m, 2H), 2.98 (m, 2H), 5.91 (s, 2H), 7.09 (d, J=8, 1H), 7.26 (m, 2H), 7.69 (d, J=8, 1H), 7.82 (t, J=8, 1H), 7.99 (m, 2H). $^{13}$C-NMR (CDCl$_3$, δ): 14.2, 39.3, 43.2, 60.4, 106.9, 118.1, 119.7, 127.0, 129.3, 136.5, 138.6, 141.0, 151.6, 156.7. MS (%): 292 (parent+1, 100).

E. 2-(2,5-Dimethylpyrrol-1-yl)-6-{4-[2-(bis-cyclohexylmethyl-amino)-ethyl]-phenyl}-pyridine:

To a 100 mL round-bottomed flask equipped with $N_2$ inlet were added 215 mg (0.739 mmol) 2-(2,5-dimethylpyrrol-1-yl)-6-(4-(2-aminoethyl)phenyl)-pyridine, 179 uL (1.48 mmol) cyclohexanecarboxaldehyde, 7 mL methanol, and 93 mg (1.48 mmol) sodium cyanoborohydride. The reaction was stirred at room temperature for 18 h, poured into dilute aqueous sodium bicarbonate solution, and extracted into ethyl acetate. The organic layer was washed with water and brine, dried over sodium sulfate, and evaporated. The residue was chromatographed on silica gel using ethyl acetate/hexane as eluant to afford the product, 134 mg (37.5%) as an oil.

$^1$H-NMR (CDCl$_3$, δ): 0.84 (m, 4H), 1.20 (m, 6H), 1.40 (m, 2H), 1.69 (m, 6H), 1.78 (m, 2H), 2.2 (m, 6H), 2.24 (s, 6H), 2.63 (m, 2H), 2.76 (m, 2H), 5.96 (s, 2H), 7.12 (d, J=8, 1H), 7.30 (m, 2H), 7.73 (d, J=8, 1H), 7.85 (t, J=8, 1H), 8.01 (m, 2H). $^{13}$C-NMR (CDCl$_3$, δ): 13.5, 26.3, 27.0, 31.9, 33.5, 36.4, 57.2, 62.4, 106.9, 118.0, 119.5, 126.8, 128.7, 129.3, 135.9, 138.5, 143.0, 151.6, 157.0. MS (%): 484 (parent+1, 100).

F. 6-{4-[2-(Bis-cyclohexylmethyl-amino)-ethyl]-phenyl}-pyridin-2-ylamine:

To a 100 mL round-bottomed flask equipped with condenser and $N_2$ inlet were added 134 mg (0.277 mmol) 2-(2,5-dimethylpyrrol-1-yl)-6-{4-[2-(bis-cyclohexylmethyl-amino)-ethyl]-phenyl}-pyridine, 96 mg (1.387 mmol) hydroxylamine hydrochloride, 1 mL water and 5 mL ethanol. The solution was heated at 80° C. for 35 h, cooled, and poured into dilute aqueous hydrochloric acid. The aqueous layer washed with ethyl acetate, the pH adjusted to 11 with 1 N sodium hydroxide solution, and extracted with ethyl acetate. The organic layer was washed with brine, dried over sodium sulfate, and evaporated. The resulting oil was taken up in ether and precipitated using 1 N HCl in ether. The product was collected as a tan solid, mp 75–85° C., 68 mg (51%).

$^1$H-NMR (CDCl$_3$, δ): 0.81 (m, 6H), 1.24 (m, 6H), 1.38 (m, 2H), 1.66 (m, 6H), 1.74 (m, 2H), 2.17 (d, J=7, 4H), 2.60 (m, 2H), 2.70 (m, 2H), 4.55 (bs, 2H), 6.40 (d, J=8, 1H), 7.04 (d, J=7, 1H), 7.23 (m, 2H), 7.45 (t, J=8, 1H), 7.81 (m, 2H). $^{13}$C-NMR (CDCl$_3$, δ): 26.3, 27.0, 31.9, 33.4, 36.4, 57.2, 62.4, 106.8, 110.7, 126.7, 129.0, 137.2, 138.3, 142.0, 156.2, 158.3. MS (%): 406 (parent+1, 100). Anal. Calc'd. for $C_{27}H_{39}N_3 \cdot 2HCl \cdot 2H_2O$: C, 63.02, H, 8.81, N, 8.17. Found: C, 62.54, H, 8.92, N, 8.56.

EXAMPLE 125

6-{4-[2-(4-Phenyl-butylamino)-ethyl]-phenyl}-pyridin-2-ylamine

A. N-(2-(2,5-Dimethylpyrrol-1-yl)-6-ethyl]-phenyl}-pyridyl)-(3-phenylbutyramide):

To a 100 mL round-bottomed flask equipped with $N_2$ inlet were added 200 mg (0.687 mmol) 2-(2,5-dimethylpyrrol-1-yl)-6-(4-(2-aminoethyl)phenyl)-pyridine (Example 100D), 113 mg (0.687 mmol) 3-phenylbutyric acid, 132 mg (0.687 mmol) EDAC, 10 mg N-hydroxybenzotriazole, 5 mL dry acetonitrile, and 211 uL (1.51 mmol) triethylamine. The reaction was stirred at room temperature for 12 h, poured into dilute aqueous citrate solution, and extracted into ethyl acetate. The organic layer was washed with water, aqueous sodium bicarbonate solution, and brine, dried over sodium sulfate, and evaporated. The resulting yellow oil, 300 mg (100%) was used directly.

$^1$H-NMR (CDCl$_3$, δ): 1.28 (m, 2H), 2.23 (s, 6H), 2.61 (m, 2H), 2.85 (m, 4H), 3.51 (m, 2H), 5.95 (s, 2H), 7.1–7.4 (m, 8H), 7.70 (d, J=8, 1H), 7.85 (t, J=8, 1H), 8.00 (m, 2H). $^{13}$C-NMR (CDCl$_3$, δ): 13.5, 27.1, 35.2, 35.5, 35.8, 40.4, 107.0, 118.2, 119.8, 125.9, 127.2, 128.4, 128.5, 128.6, 129.2, 136.7, 138.0, 140.5, 141.5, 151.7, 156.6, 172.8. MS (%): 438 (parent+1, 100).

B2-(2,5-Dimethylpyrrol-1-yl)-6-{4-[2-(4-phenylbutyl)-ethyl]-phenyl}-pyridine:

To a 100 mL round-bottomed flask equipped with condenser and $N_2$ inlet were added 300 mg (0.687 mmol) N-(2-(2,5-dimethylpyrrol-1-yl)-6-ethyl]-phenyl}-pyridyl)-(3-phenylbutyramide), 10 mL dry tetrahydrofuran, and 1.0 mL (2.06 mmol) of a 2.0 M solution of borane methyl sulfide in tetrahydrofuran. The reaction was refluxed 20 h, cooled, and evaporated. The riesidue was taken up in 40 mL ethanol, treated with 1 g sodium carbonate and 0.5 g cesium fluoride, and refluxed 40 h. The reaction was cooled and evaporate, and the residue taken up in ethyl acetate/water. The organic layer was separated, washed with water and brine, dried over sodium sulfate, and evaporated. The residue was chromatographed on silica gel using methanol/methylene chloride as eluant to afford the product as a low-melting solid, 13 mg (4.5%).

$^1$H-NMR (CDCl$_3$, δ): 1.67 (m, 2H), 1.97 (m, 2H), 2.18 (s, 6H), 2.58 (m, 2H), 2.93 (m, 2H), 3.14 (m, 2H), 3.25 (m, 2H), 5.91 (s, 2H), 7.1–7.3 (m, 8H), 7.66 (d, J=8, 1H), 7.82 (t, J=8, 1H), 7.96 (m, 2H). $^{13}$C-NMR (CDCl$_3$, δ): 13.4, 26.1, 28.6, 33.8, 35.3, 47.9, 49.0, 107.0, 118.2, 119.9, 126.0, 127.4, 128.3, 128.4, 129.1, 138.2, 138.6, 141.4, 151.7, 156.4. MS (%): 424 (parent+1, 100).

C. 6-{4-[2-(4-Phenyl-butylamino)-ethyl]-phenyl}-pyridin-2-ylamine:

To a 100 mL round-bottomed flask equipped with condenser and $N_2$ inlet were added 13 mg (0.0307 mmol) 2-(2,5-dimethylpyrrol-1-yl)-6-{4-[2-(4-phenylbutyl)-ethyl]-phenyl}-pyridine, 21 mg (0.307 mmol) hydroxylamine hydrochloride, 4 mL ethanol, and 1 mL water. The reaction was refluxed 40 h, cooled, and poured into water and extracted into ethyl acetate. The organic layer was separated, washed with water and brine, dried over sodium sulfate, and evaporated. The residue was taken up in ether and precipitated with 1 N HCl in ether to afford a hygroscopic solid, 3 mg (23%).

$^1$H-NMR (CDCl$_3$, δ): 1.49 (m, 2H), 1.59 (m, 2H), 2.59 (m, 4H), 2.84 (m, 4H), 4.54 (bs, 2H), 6.42 (d, J=8, 1H), 7.03 (d, J=7.5, 1H), 7.14 (m, 2H), 7.24 (m, 5H), 7.46 (t, J=8, 1H), 7.82 (m, 2H). $^{13}$C-NMR (CDCl$_3$, δ): 29.1, 29.6, 35.8, 35.9, 49.6, 50.9, 106.9, 110.8, 125.6, 126.9, 127.1, 128.2, 128.4, 128.9, 138.3, 140.5, 142.4, 156.1, 158.2. MS (%): 346 (parent+1, 100).

EXAMPLE 126

6-{4-[2-(5-Phenyl-pentylamino)-ethyl]-phenyl}-pyridin-2-ylamine

Prepared as in Example 100A, using 4-phenyl pentanoic acid, with a 45% yield in the final step, as a solid, mp 60–70° C.

$^1$H-NMR (CDCl$_3$, δ): 1.31 (m, 2H), 1.50 (m, 2H), 1.60 (m, 2H), 2.58 (m, 4H), 2.87 (m, 4H), 4.49 (bs, 2H), 6.42 (d, J=8, 1H), 7.04 (d, J=7, 1H), 7.14 (m, 2H), 7.24 (m, 5H), 7.47 (t, J=8, 1H), 7.83 (m, 2H). $^{13}$C-NMR (CDCl$_3$, δ): 26.9, 29.6, 31.3, 35.8, 49.6, 50.9, 106.9, 110.7, 125.6, 126.9, 128.2, 128.4, 128.9, 137.8, 138.3, 142.6, 158.2. MS (%): 360 (parent+1, 100).

EXAMPLE 127

6-{4-[3-(1,2,3,4-Tetrahydro-naphthalen-2-ylamino)-propyl]-phenyl}-pyridin-2-ylamine Prepared using 2-(2,5-dimethylpyrrol-1-yl)-6-(4-(3-aminopropyl)phenyl)-pyridine, which was prepared as in Example 100, starting from 3-(4-bromophenyl)-propionic acid, which was prepared as follows: To a 500 mL round-bottomed flask equipped with addition funnel ancl $N_2$ inlet were added 45 mL formic acid, which was cooled to 0° C., followed by dropwise addition of 67 mL triethylamine. The resulting solution was warmed to room temperature, followed by addition of 9.25 g (50 mmol) of 4-bromobenzaldehyde and 7.21 g (50 mmol) of Meldrum's acid. The reaction was heated to 95° C. over 1 h, then heated at 95–100° C. for 2 h. The reaction was cooled, poured into ice/water, arid the pH adjusted to 1 with 6 N hydrochloric acid. The mixture was let stand at 0° C. for 14 h, and the precipitate collected, washed with water, and taken up in ethyl acetate and extracted with aqueous sodium bicarbonate solution. The aqueous layer was washed with ethyl acetate, then the pH adjusted to 1 with 6 N hydrochloric acid followed by extraction with ethyl acetate. The organic layer was washed with brine, dried over sodium sulfate, and evaporated to a solid, 4.56 g (40%).

$^1$H-NMR (CDCl$_3$, δ): 2.66 (t, J=7, 2H), 2.92 (t, J=7, 2H), 7.1 (m, 2H), 7.45 (m, 2H). $^{13}$C-NMR (CDCl$_3$, δ): 29.9, 35.3, 120.2, 130.0, 131.6, 139.0, 178.8.

The remaining steps were carried out following Example 124 to make 2-(2,5-dimethylpyrrol-1-yl)-6-(4-(3-amincpropyl)phenyl)-pyridine, which was then converted as follows: To a 100 mL round-bottomed flask equipped with $N_2$ inlet were added 300 mg (0.984 mmol) 2-(2,5 dimethylpyrrol-1-yl)-6-(4-(3-aminopropyl)phenyl)-pyridine, 156 uL (1.18 mmol) 1,2,3,4-tetrahydronapthalen-2-one, 7 mL methanol, and 74 mg (1.18 mmol) sodium cyanoborohydride, followed by 3 mL of 1 N HCl in methanol. The reaction was stirred at room temperature for 6 h, poured into aqueous sodium bicarbonate solution, and extracted into ethyl acetate. The organic layer was washed with water and brine, dried over sodium sulfate, and evaporated. The residue was chromatographed on silica gel using methanol/methylene chloride as eluant to afford 2-(2,5-dimethylpyrrolyl)-6-{4-[3-(1,2,3,4-tetrahydro-naphthalen-2-ylamino)-propyl]-phenyl}-pyridine as an oil, 120 mg (28%).

$^1$H-NMR (CDCl$_3$, δ): 1.70 (m, 1H), 1.99 (m, 2H), 2.11 (m, 1H), 2.205 (s, 6H), 2.7–2.9 (m, 6H), 3.04 (m, 3H), 3.6 (bs, 1H), 5.92 (s, 2H), 7.0–7.2 (m, 5H), 7.27 (m, 2H), 7.69 (d, J=8, 1H), 7.84 (t, J=8, 1H), 7.96 (m, 2H). $^{13}$C-NMR (CDCl$_3$, δ): 13.5, 27.9, 28.4, 30.5, 33.2, 45.9, 54.0, 106.9, 118.1, 119.6, 125.8, 126.0, 127.0, 128.6, 128.8, 129.3, 134.2, 138.6, 142.9, 151.6, 156.8. MS (%): 436 (parent+1, 100).

The oil was taken up 5 mL ethanol and 1 mL water and treated with 96 mg (1.38 mmol, 5 eq.) hydroxylamine hydrochloride at 80° C. for 36 h. The reaction was cooled, poured into dilute aqueous hydrochloric acid, and washed with ethyl acetate. The pH of the aqueous layer was adjusted to 10 with 1 N sodium hydroxide solution followed by extraction with ethyl acetate. The organic layer was washed with brine, dried over sodium sulfate, and evaporated to afford an oil, 65 mg (66%), which was converted to the hydrochloride sailt using HCl in ether, mp 120–130° C.

$^1$H-NMR (CDCl$_3$, δ): 1.57 (m, 2H), 1.87 (m, 2H), 2.6–3.0 (m, 9H), 4.58 (bs, 2H), 6.40 (d, J=8, 1H), 7.0–7.1 (m, 5H), 7.25 (m, 2H), 7.46 9t, J=8, 1H), 7.83 (m, 2H). $^{13}$C-NMR (CDCl$_3$, δ): 28.1, 29.6, 31.9, 33.5, 36.8, 46.6, 53.6, 106.9, 110.7, 125.7, 125.8, 126.8, 128.6, 128.7, 129.4, 135.3, 136.3, 137.4, 138.4, 142.6, 156.1, 158.3. MS (%): 358 (parent+1, 100). Anal. Calc'd. for C$_{24}$H$_{27}$N$_3$.2HCl.2/3H$_2$O: C, 65.15, H, 6.91, N, 9.50. Found: C, 65.01, H, 7.10, N, 9.22.

EXAMPLE 128

6-{4-[2-(4-Phenethyl-piperazin-1-yl)-ethyl]-phenyl}-4-methyl-pyridin-2-ylamine Refer to Scheme 3

A. ((4-Iodophenyl)acetyl)-phenethylgiperazine:

To a 100 mL round-bottomed flask equipped with N$_2$ inlet were added 1.0 g (3.816 mmol) 4-iodophenylacetic acid, 725 mg (3.816 mmol) phenethylpiperazine, 10 mL dry acetonitrile, 10 mg 1-hydroxybenzotriazole, 732 mg (3.816 mmol) EDAC, and 1.17 mL (8.395 mmol) triethylamine. The reaction was sitirred at room temperature for 16 hr, evaporated, and chromatographed on silica gel using methanol/methylene chloride as eluant to afford 1.74 g (100%) of a low-melting solid.

$^1$H-NMR (CDCl$_3$, δ): 2.34 (m, 2H), 2.45 (m, 2H), 2.58 (m, 2H), 2.75 (m, 2H), 3.43 (m, 2H), 3.63 (s, 2H), 3.65 (m, 2H), 6.97 (m, 2H), 7.17 (m, 3H), 7.25 (m, 2H), 7.62 (m, 2H). $^{13}$C-NMR (CDCl$_3$, δ): 33.5, 40.2, 41.8, 46.0, 52.7, 53.2, 60.1, 92.2, 126.1, 128.4, 128.5, 128.7, 130.8, 134.8, 137.7, 139.95, 168.7. MS (%): 435 (parent+1, 100).

B. ((4-Iodophenyl)ethyl)-phenethylpiperazine:

To a 100 mL round-bottomed flask equipped with condenser and N2 inlet were added 1.66 g (3.8 mmol) ((4-iodophenyl)acetyl)-phenethylpiperazine, 15 mL dry tetrahydrofuran, and 5.73 mL (11.46 mmol) of a 2.0 M solution of borane methyl sulfide in tetrahydrofuran. The reaction was refluxed 18 hr, cooled, and evaporated. The residue was taken up in 25 mL ethanol, and treated with 1 g sodium carbonate and 1 g cesium fluoride, then refluxed 18 hr. The reaction was cooled, evaporated, and the residue taken up in water/ethyl acetate. The organic layer was separated, washed with water and brine, dried over sodium sulfate, and evaporated. The resulting solid, mp 91–93° C. (0.74 g, 46%) was used directly.

$^1$H-NMR (CDCl$_3$, δ): 2.5–2.7 (m, 12H), 2.71 (m, 2H), 2.77 (m, 2H), 6.94 (m, 2H), 7.19 (m, 3H), 7.26 (m, 2H), 7.58 (m, 2H). $^{13}$C-NMR (CDCl$_3$, δ): 33.1, 33.6, 53.2, 60.2, 60.6, 91.1, 126.0, 128.4, 128.7, 130.8, 137.4, 140.0, 140.3. MS (%): 420 (parent+1, 100).

C. 2-(2,5-Dimethylpyrrolyl)-4-methylpyridine:

To a 250 mL round-bottomed flask equipped with condenser were added 10.8 g (100 mmol) 2-aminopyridine, 11.7 mL (100 mmol) hexane-2,5-dione, and 0.5 mL concentrated hydrochloric acid. The reaction was heated slowly to 150° C. over 2 hr, then at 165–170° C. for 2 hr, and cooled. The residue was poured into aqueous sodium bicarbonate solution, extracted into ethyl acetate, and the organic layer washed with water and brine, dried over sodium sulfate, and evaporated. The residue was chromatographed on silica gel using ethyl acetate in hexane as elijant to afford a low-melting solid, 15.36 g (83%).

$^1$H-NMR (CDCl$_3$, δ): 2.11 (s, 6H), 2.41 (s, 3H), 5.87 (s, 2H), 7.02 (bs, 1H), 7.10 (m, 1H), 8.44 (d, J=5, 1H). $^{13}$C-NMR (CDCl$_3$, δ): 13.1, 21.0, 106.7, 122.75, 123.4, 128.5, 149.0, 149.4, 152.2. MS (%): 187 (parent+1, 100).

D. 2-(2,5-Dimethylpyrrol-1-yl)-4-methyl-6-(4-(2-(phenethylpiperazin-4-yl)ethyl)phenyl)-pyridine:

To a 100 mL three-necked round-bottomed flask equipped with septum and N$_2$ inlet were added 440 mg (1.05 mmol) of ((4-iodophenyl)ethyl)-phenethylpiperazine and 5 mL dry ether. The solution was cooled to −70° C., and 0.625 mL of a 1.6 M solution (1.0 mmol) of butyl lithium in hexanes added dropwise over 5 min. The reaction was stirred 5 min at −70° C., then warmed to room temperature, and a solution of 186 mg (1.0 mmol) 2-(2,5-dimethylpyrrol-1-yl)-4-methyl-pyridine in 5 mL dry ether added over 3 min. The reaction turned to dark orange and then dark red as it was stirred at room temperature for 5 hr, then quenched with aqueous ammonium chloride. The organic layer was diluted with ethyl acetate and separated, washed with aqueous ammonium chloride and brine, dried over sodium sulfate for 14 hr in the air (to permit air oxidation to the pyridine) and evaporated. The residue was chromatographed on silica gel using aqueous acetonitrile as eluant to afford the product as an oil, 165 mg (34.5%).

$^1$H-NMR (CDCl$_3$, δ): 2.19 (s, 6H), 2.45 (s, 3H), 2.6–2.9 (m, 16H), 5.90 (s, 2H), 6.93 (m, 2H), 7.20 (m, 3H), 7.27 (m, 3H), 7.57 (m, 2H), 7.96 (d, J=8, 1H). $^{13}$C-NMR (CDCl$_3$, δ): 13.5, 21.3, 33.0, 33.5, 53.0, 60.0, 60.4, 106.7, 119.2, 120.5, 126.1, 127.0, 128.4, 128.6, 128.7, 129.1, 130.8, 137.4, 139.8, 140.1, 151.8, 156.5. MS (%): 479 (parent+1, 100).

E. 6-(4-(2-(Phenethypiperazin-4-yl)ethyl)phenyl)-4-methyl-pyridinyl-2-amine:

To a 100 mL three-necked round-bottomed flask equipped with septum and N$_2$ inlet were added 165 mg (0.345 mmol) 2-(2,5-dimethylpyrrol-1-yl)-4-methyl-6-(4-(2-(phenethylpiperazin-4-yl)ethyl)phenyl)-pyridine, 120 mg (1.726 mmol) hydroxylamine hydrochloride, 1 mL water, and 5 mL ethanol. The reaction was refluxed 14 hr, cooled, evaporated, and taken up in ethyl acetate. The organic layer was washed with water and brine, dried over sodium sulfate, and evaporated. The residue was chromatographed on silica gel usirg methanol/methylene chloride as eluant to afford an oil, which was converted to thie hydrochloride salt using 1 N HCl in ether to give 18 mg (10%), mp 242–250° C.

$^1$H-NMR (CDCl$_3$, δ): 2.22 (s, 3H), 2.63 (m, 4H), 2.79 (m, 12H), 6.24 (s, 1H), 6.80 (s, 1H), 7.1–7.3 (m, 7H), 7.71 (m, 2H). $^{13}$C-NMR (CDCl$_3$, δ): 21.1, 32.8, 33.0, 52.6, 59.9, 60.1, 107.7, 112.6, 126.2, 127.0, 128.4, 128.6, 128.8, 139.5, 140.2, 149.8, 158.4. MS (%): 401 (parent+1, 100).

EXAMPLE 129

6-{4-[3-(4-Phenethyl-piperazin-1-yl)-propyl]-phenyl}-pyridin-2-ylamine

Prepared as in Example 128, starting from 3-(4-bromophenyl)-propionic acid, prepared in Example 125, concluding with deblocking with hydroxylamine hydrochloride, affording a residue which was purified by column chromatography using methanol/methylene chloride to give a 46% yield of an oil, which was converted to the hydrochloride salt using 1 N HCl in ether to give mp 125–140° C.

$^1$H-NMR (CDCl$_3$, δ): 1.87 (m, 2H), 2.40 (m, 4H), 2.5–2.7 (m, 10H), 2.81 (m, 2H), 4.73 (bs, 2H), 6.38 (d, J=8, 1H), 7.01 (d, J=7.5, 1H), 7.1–7.3 (m, 7H), 7.44 (t, J=8, 1H), 7.80 (m, 2H). $^{13}$C-NMR (CDCl$_3$, δ): 28.3, 32.7, 33.5, 53.0, 57.95, 60.5, 107.0, 110.7, 126.0, 126.9, 128.4, 128.6, 137.3, 138.0, 138.4, 140.3, 142.6, 156.2, 158.4. MS (%): 401 (parent+1, 100). Anal. Calc'd. for $C_{26}H_{32}N_4 \cdot 3HCl \cdot H_2O$: C, 59.15, H, 7.06, N, 10.61. Found: C, 58.67, H, 7.02, N, 11.23.

EXAMPLE 130

6-{3-[2-(4-Phenethyl-piperazin-1-yl)-ethyl]-phenyl}-pyridin-2-ylamine

Prepared using the procedures in Example 1, with 3-aminophenethyl alcohol as starting material, with the final condensation step proceeding in 25% yield after chromatography on silica gel using methanol/methylene chloride as eluant. The product was precipitated from ether as the hydrochloride salt using 1 N HCl in ether, mp 120° C. (dec.).

$^1$H-NMR (δ, CDCl$_3$): 2.5–2.7 (m, 12H), 2.80 (m, 2H), 2.87 (m, 2H), 4.54 (bs, 2H), 6.41 (d, J=8, 1H), 7.05 (d, J=7, 1H), 7.20 (m, 4H), 7.25 (m, 2H), 7.33 (t, J=8, 1H), 7.46 (t, J=8, 1H), 7.73 (m, 1H), 7.78 (s, 1H). $^{13}$C-NMR (δ, CDCl$_3$): 33.6, 33.7, 53.2, 60.5, 60.6, 107.1, 111.0, 124.6, 126.0, 127.2, 128.4, 128.6, 128.7, 129.0, 138.3, 139.8, 140.3, 140.6, 156.2, 158.3. MS (%): 387 (parent+1, 100). Anal. Calc'd. for $C_{25}H_{30}N_4 \cdot 2HCl \cdot 1/2CH_2Cl_2 \cdot H_2O$: C, 58.91, H, 6.19, N, 10.78. Found: C, 59.22, H, 6.64, N, 10.38.

EXAMPLE 131

6-{4-[2-(4-Amino-2,6-dimethyl-piperidin-1-yl)-ethyl]-phenyl}-pyridin-2-ylamine (cis diastereomer)

Prepared as in Example 108, using the trans isomer of N-benzyl-2,6-dimethylpiperidin-4-one from Example 108A, with the final step in 92% yield, as the hydrochloride salt.

$^1$H-NMR (CDCl$_3$, δ): 1.05 (m, 6H), 1.47 (m, 2H), 1.71 (m, 2H), 2.54 (m, 2H), 2.71 (m, 2H), 2.83 (m, 2H), 3.34 (m, 1H), 4.49 (bs, 2H), 6.41 (d, J=8, 1H), 7.05 (d, J=8, 1H), 7.25 (m, 2H), 7.46 (t, J=8, 1H), 7.82 (m, 2H). $^{13}$C-NMR (CDCl$_3$, δ): 11.3, 21.4, 35.6, 41.4, 44.1, 45.5, 48.8, 51.1, 51.2, 106.8, 110.7, 126.7, 128.9, 137.5, 138.3, 141.5, 156.1, 158.2. FAB MS (%): 325 (parent+1, 4), 279 (20), 167 (45), 149 (100), 113 (36). HRMS Calc'd. for $C_{20}H_{29}N_4$ (parent+1): 325.2392. Found: 325.2369.

EXAMPLE 132

6-{4-[2-(4-Amino-2,6-diisopropyl-piperidin-1-yl)-ethyl]-phenyl}-pyridin-2-ylamine (cis diastereomer)

Prepared as in Example 108 using isopropanal, to afford the product as an oil in 90% yield in the final step, which was converted to the hydrochloride salt-as an amorphous solid.

$^1$H-NMR (CDCl$_3$, δ): 0.8–1.0 (m, 12H), 1.60 (m, 4H), 1.84 (m, 2H), 2.13 (m, 1H), 2.37 (m, 1H), 2.51 (m, 1H), 2.65 (m, 2H), 2.76 (m, 2H), 4.54 (bs, 2H), 6.39 (d, J=8, 1H), 7.03 (d, J=8, 1H), 7.21 (m, 2H), 7.44 (t, J=8, 1H), 7.81 (m, 2H). $^{13}$C-NMR (CDCl$_3$, δ): 20.6, 20.8, 21.1, 27.1, 29.6, 29.9, 33.9, 36.6, 46.2, 47.8, 60.4, 63.0, 106.7, 110.6, 126.6, 128.9, 137.2, 138.2, 141.5, 156.0, 158.2. APCI MS (%): 381 (parent+1, 100).

EXAMPLE 133

6-{4-[2-(4-Isobutyl-piperazin-1-yl)-1-methyl-ethyl]-phenyl}-pyridin-2-ylamine

A. 2-(2,5-Dimethylpyrrolyl)-6-((4-(1-cyanoethyl)phenyl))-pyridine:

To a 100 mL round-bottomed flask equipped with septum and N$_2$ inlet were added 500 mg (1.74 mmol) 2-(2,5-dimethylpyrrolyl)-6-(4-(cyanomethyl)phenyl))-pyridine (Example 112) and 17 mL dry tetrahydrofuran. The solution was cooled to −78° C., and 1.92 mL (1.92 mmol) of a 1.0 M solution of lithium bistrimethylsilylamide was added dropwise over 3 minutes. After stirring for 15 minutes, 0.23 mL (3.66 mmol) methyl iodide was added, and stirring continued at −78° C. for another 15 minutes. The reaction was then poured into aqueous ammonium chloride and extracted into ethyl acetate. The organic layer was washed with brine, dried over sodium sulfate, and evaporated. The residue was chromatographed on silica gel with hexane/ethyl acetate as eluant to afford 404 mg (77%) of an oil.

$^1$H-NMR (CDCl$_3$, δ): 1.67 (d, J=7, 3H), 2.22 (s, 6H), 3.96 (q, J=7, 1H), 5.95 (s, 2H), 7.17 (d, J=8, 1H), 7.45 (m, 2H), 7.75 (d, J=8, 1H), 7.89 (t, J=8, 1H), 8.10 (m, 2H). $^{13}$C-NMR (CDCl$_3$, δ): 13.5, 21.4, 31.1, 107.1, 118.3, 120.2, 121.4, 127.2, 127.7, 128.7, 138.2, 138.3, 138.8, 141.8, 156.0. IR (neat, KBr): 2240 (CN). FAB MS (%): 302 (parent+1, 4), 279 (20), 167 (45), 149 (100), 113 (36).

B. 2-(2,5-Dimethylpyrrolyl)-6-((4-(1-carboxyethyl)phenyl))-pyridine:

To a 100 mL round-bottomed flask equipped with condenser and N$_2$ inlet were added 400 mg (1.33 mmol) 2-(2,5-dimethylpyrrolyl)-6-((4-(1-cyanoethyl)phenyl))-pyridine and 20 mL ethanol. After heating to reflux, 30 mL of a 10% aqueous solution of sodium hydroxide was added dropwise slowly, and refluxing was continued overnight. The reaction was cooled and the pH adjusted to 1 with 6 N hydrochloric acid, then extracted into ethyl acetate. The organic layer was washed with brine, dried over sodium sulfate, and evaporated to a brown solid, mp 149–155° C., 384 mg (90.5%).

$^1$H-NMR (CDCl$_3$, δ): 1.55 (d, J=7, 3H), 2.22 (s, 6H), 3.80 (q, J=7, 1H), 5.95 (s, 2H), 7.14 (d, J=8, 1H), 7.43 (m, 2H), 7.73 (d, J=8, 1H), 7.87 (t, J=8, 1H), 8.05 (m, 2H). $^{13}$C-NMR (CDCl$_3$, δ): 13.5, 18.1, 45.2, 107.0, 118.3, 119.9, 127.3, 128.1, 128.7, 137.5, 138.65, 141.1, 151.7, 156.5, 180.4. FAB MS (%): 321 (parent+1, 4), 279 (20), 167 (45), 149 (100), 113 (36). Anal. Calc'd. for $C_{20}H_{20}N_2O_2 \cdot 1/4H_2O$: C, 73.94, H, 6.36, N, 8.62. Found: C, 73.95, H, 6.18, N, 8.41.

C. 2-(2,5-Dimethylpyrrolyl)-6-((4-(1-(4-isobutylpiperazin-1-ylamido)ethyl)phenyl))-pyridine:

To a 100 mL round-bottomed flask equipped with condenser and N$_2$ inlet were added 187 mg (0.584 mmol) 2-(2,5-dimethylpyrrolyl)-6-((4-(1-carboxyethyl)phenyl))-pyridine, 124 mg (0.584 mmol) N-isobutylpiperazine hydrochloride, 112 mg (0.584 mmol) N-ethyl-N-3-dimethylaminopropyl-carbodiimide, 79 mg (0.584 mmol) 1-hydroxybenztriazole, 0.2 mL (1.461 mmol) triethylamine, and 6 mL acetonitrile. The reaction was stirred at room temperature for 24 h, poured into aqueous sodium bicarbonate solution and ethyl acetate. The organic layer was washed with brine, dried over sodium sulfate, and evaporated. The residue was chromatographed on silica gel using methanol/methylene chloride as eluant to afford 218 mg (84%) of an oil.

$^1$H-NMR (CDCl$_3$, δ): 0.82 (d, J=7, 6H), 1.45 (d, J=7, 3H), 1.68 (m, 1H), 1.88 (m, 1H), 1.96 (m, 2H), 2.20 (s, 6H), 2.2 (m, 2H), 2.37 (m, 1H), 3.33 (m, 1H), 3.42 (m, 1H), 3.54 (m, 1H), 3.74 (m, 1H), 3.93 (q, J=7, 1H), 5.92 (s, 2H), 7.12 (d, J=8, 1H), 7.24 (m, 2H), 7.72 (d, J=8, 1H), 7.85 (t, J=8, 1H), 8.01 (m, 2H). $^{13}$C-NMR (CDCl$_3$, δ): 13.5, 20.6, 20.7, 25.3, 42.0, 43.0, 45.5, 53.1, 53.3, 66.5, 107.0, 118.2, 119.8, 127.5, 127.7, 128.6, 136.9, 138.6, 143.5, 151.7, 156.5, 171.7. APCI MS (%): 445 (parent+1, 100).

D2-(2,5-Dimethylpyrrolyl)-6-{4-[2-(4-isobutyl-piperazin-1-yl)-1-methyl-ethyl]-phenyl}-pyridine:

To a 100 mL round-bottomed flask equipped with condenser and N$_2$ inlet were added 218 mg (0.491 mmol)

2-(2,5-dimethylpyrrolyl)-6-((4-(1-(4-isobutylpiperazin-1-ylamido)ethyl)phenyl))-pyridine, 20 mL dry tetrahydrofuran, and 10 mL (20 mmol) of a 2.0 M solution of borane methyl sulfide in tetrahydrofuran. The solution was refluxed 24 hr, cooled, and the tetrahydrofuran evaporated. The residue was treated with 25 mL ethanol, 1 g sodium carbonate, and 300 mg cesium fluoride, and refluxed 24 hr. The reaction was cooled, poured into 1 N hydrochloric acid, and washed with ethyl acetate. The aqueous layer was adjusted to pH, 10 with 6 N sodium hydroxide solution and extracted into ethyl acetate. The organic layer was washed with brine, dried over sodium sulfate, and evaporated. Both organic layers were collected, and the first one used subsequently.

APCI MS (%): 431 (parent+1, 100).

E. 6-{4-[2-(4-Isobutyl-piperazin-1-yl)-1-methyl-ethyl]-phenyl}-pyridin-2-ylamine:

Prepared using hydroxylamine hydrochloride as in Example 124F. Purification was effected by making the N-trityl derivative using triphenylmethyl chloride and triethylamine in methylene chloride at room temperature overnight, followed by chromatography on silica gel using methanol/methylene chloride as eluant, and then removal of the trityl group using 50% aqueous formic acid at 55° C. for 1 h, followed by filtration, adjustment of the filtrate to pH, 10 with 6 N sodium hydroxide solution, and extraction into ethyl acetate. The resulting material was converted to the hydrochloride salt using HCl in ethyl ether to give a white solid, mp 250–260° C., in 17% yield.

$^1$H-NMR (CDCl$_3$, δ): 0.86 (d, J=7, 6H), 1.26 (d, J=6, 3H), 1.74 (m, J=7, 1H), 2.04 (d, J=7, 2H), 2.37 (m, 6H), 2.47 (d, J=7, 2H), 2.97 (m, 1H), 4.48 (bs, 2H), 6.40 (d, J=8, 1H), 7.03 (d, J=7.5, 1H), 7.25 (m, 2H), 7.46 (t, J=8, 1H), 7.82 (m, 2H). $^{13}$C-NMR (CDCl$_3$, δ): 20.1, 20.9, 25.3, 37.2, 53.5, 66.0, 66.9, 106.7, 110.7, 126.7, 127.3, 127.8, 137.5, 138.2, 146.9, 156.1, 158.1. APCI MS (%): 353 (parent+1, 100). Anal. Calc'd. for C$_{22}$H$_{32}$N$_4$.3HCl.3/2H$_2$O.1/2(C$_4$H$_{10}$O): C, 55.12, H, 7.71, N, 10.71. Found: C, 55.47, H, 8.10, N, 10.52.

EXAMPLE 134

6-{4-[1-Benzyl-2-(4-isobutyl-piperazin-1-yl)-ethyl]-phenyl}-pyridin-2-ylamine

Prepared as in Example 133 using benzyl bromide in the alkylation analogous to Example 133A in 13% yield for the final deblocking step, converted to the hydrochloride salt in ether.

$^1$H-NMR (CDCl$_3$, δ): 0.86 (d, J=6, 6H), 1.73 (m, J=6, 1H), 2.03 (d, J=7, 2H), 2.37 (m, 6H), 2.53 (m, 3H), 2.69 (m, 1H), 2.83 (m, 1H), 3.14 (m, 2H), 4.465 (bs, 2H), 6.40 (d, J=8, 1H), 6.97 (m, 2H), 7.03 (d, J=7.5, 1H), 7.13 (m, 5H), 7.45 (t, J=8, 1H), 7.78 (m, 2H). $^{13}$C-NMR (CDCl$_3$, δ): 20.9, 25.3, 40.6, 45.1, 53.4, 53.5, 63.7, 66.8, 106.7, 110.7, 125.6, 126.5, 127.9, 128.1, 129.1, 137.4, 138.2, 140.4, 144.5, 156.0, 158.1. APCI MS (%): 429 (parent+1, 100). Anal. Calc'd. for C$_{28}$H$_{36}$N$_4$.3HCl.H$_2$O.1/2(C$_4$H$_{10}$O): C, 60.76, H, 7.82, N, 9.45, Found: C, 61.14, H, 7.93, N, 9.17.

EXAMPLE 135

6-[4-(Phenethylamino-methyl)-phenyl]-pyridin-2-ylamine

A. 2-(2,5-Dimethylpyrrolyl)-6-(4-carboxyphenyl)-pyridine:

Prepared as in Example 112A, using 4-carboxyphenyl boronic acid, in 22% yield, as a low-melting solid.

$^1$H-NMR (CDCl$_3$, δ): 2.22 (s, 6H), 5.94 (s, 2H), 7.21 (d, J=8, 1H), 7.81 (d, J=8, 1H), 7.92 (t, J=8, 1H), 8.18 (m, 4H). APCI MS (%): 293 (parent+1, 100).

B. 2-(2,5-Dimethylpyrrolyl)-6-(4-(N-phenethylcarboxamido)phenyl)-pyridine:

Prepared as in Example 108F, using the above and phenethylamine, in 70% yield, as a low-melting yellow solid.

$^1$H-NMR (CDCl$_3$, δ): 2.20 (s, 6H), 2.95 (t, J=7, 2H), 3.73 (dt, J=5,7, 2H), 5.925 (s, 2H), 6.17 (broad triplet, J=5, 1H), 7.17 (d, J=8, 1H), 7.24 (m, 3H), 7.31 (m, 2H), 7.78 (m, 3H), 7.89 (t, J=8, 1H), 8.10 (m, 2H). APCI MS (%): 396 (parent+1, 100).

C. 6-(4-(N-phenethylcarboxamido)phenyl)-pyridin-2-ylamine:

Prepared as in Example 1F, in 36% yield, as a low-melting tan solid.

$^1$H-NMR (CDCl$_3$, δ): 2.94 (t, J=7, 2H), 3.72 (dt, J=5,7, 2H), 4.93 (bs, 2H), 6.175 (m, 1H), 6.52 (d, J=8, 1H), 7.09 (d, J=7, 1H), 7.24 (m, 3H), 7.31 (m, 2H), 7.54 (t, J=8, 1H), 7.75 (m, 2H), 7.97 (m, 2H). APCI MS (%): 318 (parent+1, 100).

D. 6-[4-(Phenethylamino-methyl)-phenyl]-pyridin-2-ylamine:

Prepared as in Example 133D in 61% yield, mp 236–238° C., as the hydrochloride salt.

$^1$H-NMR (CDCl$_3$, δ): 2.81–2.85 (m, 2H), 2.88–2.92 (m, 2H), 3.84 (s, 2H), 4.47 (bs, 2H), 6.43 (d, J=8, 1H), 7.05 (d, J=8, 1H), 7.18–7.29 (m, 3H), 7.24–7.27 (m, 2H), 7.29–7.34 (m, 2H), 7.47 (t, J=8, 1H), 7.86 (d, J=8, 1H). $^{13}$C-NMR (CD$_3$OD, δ) 33.3, 49.4, 50.0, 51.7, 112.3, 113.4, 128.3, 129.1, 129.8, 130.0, 132.3, 136.1, 137.8, 145.8, 147.2, 157.4. MS (%): 304 (parent+1, 100).

EXAMPLE 136

6-{4-[(Cyclohexyl-methyl-amino)-methyl]-phenyl}-pyridin-2-ylamine

Prepared as in Example 135 in 43% yield, mp>250° C., as the hydrochloride salt.

$^1$H-NMR (CDCl$_3$, δ): 1.10–1.30 (m, 5H), 1.60–1.63 (m, 1H), 1.63–1.87 (m, 4H), 2.20 (s, 3H), 2.41–2.46 (m, 1H), 3.60 (bs, 2H), 4.48 (bs, 2H), 6.44 (d, J=8, 1H), 7.06 (d, J=8, 1H), 7.41–7.50 (m, 3H), 7.83–7.87 (m, 2H). MS(%): 296 (parent+1, 100).

EXAMPLE 137

6-[4-(4-Amino-piperidin-1-ylmethyl)-phenyl}-pyridin-2-ylamine

Prepared as in Example 135 as an amorphous solid in 25% yield.

$^1$H-NMR (CDCl$_3$, δ): 1.30–1.34 (m, 2H), 1.71–1.74 (m, 2H), 1.97–2.00 (m, 2H), 2.57–2.60 (m, 1H), 2.77–2.80 (m, 2H), 3.46 (s, 2H), 6.39 (d, J=8, 1H), 6.94 (d, J=8, 1H), 7.27–7.29 (m, 2H), 7.42 (t, J=8, 1H), 7.70–7.73 (m, 2H). MS (%): 283 (parent+1, 100).

EXAMPLE 138

6-(4-Piperidin-1-ylmethyl-phenyl)-pyridin-2-ylamine

Prepared as in Example 135 in 53% yield, mp>250° C., as the hydrochloride salt.

$^1$H-NMR (CDCl$_3$, δ): 1.40–1.42 (m, 2H), 1.54–1.59 (m, 4H), 2.39 (bs, 4H), 3.51 (s, 2H), 4.50 (bs, 2H), 6.42 (d, J=8, 1H), 7.05 (d, J=8, 1H), 7.36 (d, J=8, 2H), 7.47 (t, J=8, 1H), 7.84 (d, J=8, 2H). $^{13}$C-NMR (CDCl$_3$, δ): 24.2, 25.7, 54.3, 63.4, 106.9, 110.8, 126.5, 129.5, 138.3, 156.0. MS (%): 268 (parent+1, 100).

EXAMPLE 139

6-[4-(Indan-2-ylaminomethyl)-phenyl]-pyridin-2-ylamine

Prepared as in Example 135 in 35% yield, mp 185–187° C., as the hydrochloride salt.

$^1$H-NMR (CDCl$_3$, δ): 2.81 (dd, J$_1$=9, J$_2$=6, 2H), 3.16 (dd, J$_1$=9, J$_2$=6, 2H), 3.66–3.69 (m, 1H), 3.89 (s, 2H), 4.48 (bs, 2H), 6.42 (d, J=8, 1H), 7.06 (d, J=8, 1H), 7.11–7.20 (m, 2H), 7.40 (d, J=8, 1H), 7.49 (t, J=7, 1H), 7.88 (d, J=8, 1H). $^{13}$C-NMR (CDCl3, δ): 39.8, 51.9, 58.8, 107.0, 110.9, 124.7, 126.4, 126.9, 128.5, 138.4. MS (%): 316 (parent+1, 100).

EXAMPLE 140

6-{4-[(2-Thiophen-2-yl-ethylamino)-methyl]-phenyl}-pyridin-2-ylamine

Prepared as in Example 135 in 68% yield as an amorphous solid $^1$H-NMR (CDCl$_3$, δ): 2.92 (t, J=6, 2H), 3.04 (t, J=6, 2H), 3.84 (s, 2H), 4.48 (bs, 2H), 6.43 (d, J=8, 1H), 6.81–6.82 (m, 1H), 6.91–6.93 (m, 1H), 7.06 (d, J=8, 1H), 7.13 (m, 1H), 7.34 (d, J=8, 2H), 7.48 (t, J=7, 1H), 7.86 (d, J=8, 2H). $^{13}$C-NMR (CDCl$_3$, δ): 30.4, 50.3, 53.3, 106.9, 110.8, 123.5, 124.9, 126.8, 128.2, 138.3, 140.6, 142.9, 155.7, 158.2. MS (%): 310 (parent+1, 100).

EXAMPLE 141

6-[2-Methoxy-4-(phenethylamino-methyl)-phenyl]-pyridin-2-ylamine Refer to Scheme 5

A. 2-Methoxy-4-methylphenylboronic acid:

To a 125 mL three-necked round-bottomed flask equipped with septum and N$_2$ inlet were added 2.3 g (11.4 mmol) 2-bromo-5-methylanisole (prepared as described in EP 470794 A1, see Chem. Abs., 116:193935) and 25 mL dry tetrahydrofuran. The solution was cooled to –70° C., and 5.5 mL (13.7 mmol) of a 2.5 M solution of butyl lithium in hexane added over 3 min. The reaction was stirred 1 h at –70° C., then 2.34 mL (13.7 mmol) triethyl borate was added, and stirring continued for 2 h at –70° C. The reaction was warmed to room temperature and stirred for 60 h, quenched with aqueous ammonium chloride solution and dilute hydrochloric acid solution, and extracted with ethyl acetate. The organic layer was washed with brine, dried over sodium sulfate and evaporated to a dark oil, which was triturated with hexane to afford 630 mg (33%) of an oil.

$^1$H-NMR (CDCl$_3$, δ): 2.37 (s, 3H), 3.89 (s, 3H), 6.715 (s, 1H), 6.84 (d, J=7, 1H), 7.70 (d, J=7, 1H).

B. 2-(2,5-Dimethylpyrrolyl)-6-(2-methoxy-4-methylphenyl)-pyridine:

Prepared as in Example 112A, using 953 mg (3.795 mmol) 2-(2,5-dimethyl)-6-bromopyridine, 630 mg (3.795 mmol) 2-methoxy-4-methylphenylboronic acid, 1.61 g (15.18 mmol) sodium carbonate, 44 mg (0.038 mmol) tetrakis-triphenylphosphine palladium, 18 mL ethanol, and 2 mL water, to give 670 mg (60%) of an oil.

$^1$H-NMR (CDCl$_3$, δ): 2.28 (s, 6H), 2.45 (s, 3H), 3.93 (s, 3H), 5.98 (s, 2H), 6.87 (s, 1H), 6.94 (d, J=8, 1H), 7.14 (d, J=8, 1H), 7.84 (t, J=8, 1H), 7.91 (d, J=8, 1H), 7.98 (d, J=8, 1H). $^{13}$C-NMR (CDCl$_3$, δ): 13.4, 21.7, 55.4, 106.7, 112.2, 119.2, 121.8, 123.1, 125.1, 128.6, 131.2, 137.6, 140.6, 151.3, 155.6, 157.1. APCI MS (%): 293 (parent+1, 100).

C. 6-(2-Methoxy-4-methylphenyl)-pyridin-2-ylamine:

Prepared as in Example 1F in 90% yield, as an oil.

$^1$H-NMR (CDCl$_3$, δ): 2.365 (s, 3H), 3.785 (s, 3H), 4.67 (bs, 2H), 6.34 (d, J=8, 1H), 6.76 (s, 1H), 6.84 (d, J=8, 1H), 7.09 (d, J=7.5, 1H), 7.39 (t, J=8, 1H), 7.57 (d, J=8, 1H). $^{13}$C-NMR (CDCl$_3$, δ): 21.6, 55.4, 106.5, 112.15, 114.95, 121.5, 126.5, 130.6, 137.4, 139.5, 154.3, 156.7, 158.2. APCI MS (%): 215 (parent+1, 100).

D. 2-Phthalimido-6-(2-methoxy-4-methylphenyl)-pyridine:

To a 100 mL round-bottomed flask eiquipped with condenser and N$_2$ inlet were added 440 mg (2.15 mmol) 6-(2-methoxy-4-methylphenyl)-pyridin-2-ylamine, 502 mg (2.29 mmol) N-carbethoxyphthalimide, and 20 mL dry toluene. The solution was refluxed 14 h, cooled, and purified by chromatography on silica gel using hexane/ethyl acetate as eluant to afford 710 mg (90%) of a low-melting solid.

$^1$H-NMR (CDCl$_3$, δ): 2.355 (s, 3H), 3.84 (s, 3H), 6.775 (s, 1H), 6.85 (d, J=8, 1H), 7.27 (m, 1H), 7.76 (m, 3H), 7.83 (t, J=8, 1H), 7.92 (m, 3H). $^{13}$C-NMR (CDCl$_3$, δ): 21.3, 55.2, 112.0, 119.6, 121.6, 123.5, 124.7, 131.0, 131.5, 133.9, 134.4, 135.3, 137.8, 140.6, 156.0, 156.8, 166.8. APCI MS (%): 345 (parent+1, 100).

E. 2-Phthalimido-6-(2-methoxy-4-bromomethylphenyl)-pyridine:

To a 100 mL round-bottomed flask equipped with condenser and N$_2$ inlet were added 0.7 g (2.03 mmol) 2-phthalimido-6-(2-methoxy-4-methylphenyl)-pyridine, 0.36 g (2.03 mmol) N-bromosuccinimide, 10 mg azobisisobutyronitrile, and 30 mL carbon tetrachloride. The reaction was heated at 50° C. for 24 h, cooled, diluted with methylene chloride, and washed with aqueous sodium bicarbonate solution, dried over magnesium sulfate, and evaporated. The crude residue, 0.81 g, was used directly.

APCI MS (%): 423/425 (parent+1, 100).

F. 2-Phthalimido-6-[2-methoxy-4-(phenethylamino-methyl) phenyl]-pyridine:

To a 100 mL round-bottomed flask, equipped with condenser and N$_2$ inlet were added 120 mg (0.28 mmol) 2-phthalimido-6-(2-methoxy-4-bromomethylphenyl)-pyridine, 0.04 mL (0.3 mmol) phenethylamine, 29 mg (0.35 mmol) sodium bicarbonate, and 6 mL acetonitrile. The reaction wAas heated at 50° C. for 8 h, cooled, and extracted into ethyl acetate. The organic layer was washed with brine, dried over magnesium sulfate, and evaporated. The residue was chromatographed on silica gel using methanol/methylene chloride to afford 40 mg (31%) of an oil.

$^1$H-NMR (CDCl$_3$, δ): 2.85 (m, 2H), 2.89 (m, 2H), 3.84 (s, 2H), 3.85 (s, 3H), 6.96 (m, 2H), 7.2–7.4 (m, 7H), 7.8–8.0 (m, 6H). APCI MS (%): 464 (parent+1, 100).

G. 6-[2-Methoxy-4-(phenethylamino-methyl)-phenyl]-pyridin-2-ylamine:

To a 100 mL round-bottomed flask equipped with condenser and N$_2$ inlet were added 30 mg (0.065 mmol) 2-phthalimide-6-[2-methoxy-4-(phenethylamino-methyl) phenyl)-pyridine, 7 uL (0.2 mmol) hydrazine, and 3 mL methanol. The reaction was heated at 50° C. for 3.5 h, cooled, arid concentrated. The residue was dissolved in methylene chloride, washed with aqueous sodium bicarbonate solution, dried over magnesium sulfate, and evaporated. The residue was chromatographed on silica gel using methanol/methylene chloride as eluant to afford 10 mg (46%) of an oil, which was converted to the hydrochloride salt.

$^1$H-NMR (CDCl$_3$, δ): 2.88–2.95 (m, 4H), 3.82 (s, 3H), 3.87 (s, 2H), 6.43 (d, J=8, 1H), 6.94 (bs, 1H), 7.10 (d, J=8, 1H), 7.18–7.20 (m, 3H), 7.25–7.29 (m, 2H), 7.45 (t, J=8, 1H), 7.61 (d, J=8, 1H). MS(%): 334 (parent+1, 100).

EXAMPLE 142

6-{4-[(Cyclohexyl-methyl-amino)-methyl]-2-methoxy-phenyl}-pyridin-2-ylamine

Prepared as in Example 141, using N-methyl-cyclohexylamine, with an 86% yield in the final step.

¹H-NMR (CDCl₃, δ): 1.07–1.34 (m, 5H), 1.60–1.63 (m, 1H), 1.77–1.87 (m, 4H), 2.22 (s, 3H), 2.42–2.47 (m, 1H), 3.59 (s, 2H), 3.83 (s, 3H), 4.44 (bs, 2H), 6.41 (d, J=8, 1H), 7.95–7.98 (m, 2H), 7.13 (d, J=8, 1H), 7.44 (t, J=8, 1H), 7.59 (d, J=8, 1H). ¹³C-NMR (CDCl₃, δ): 26.0, 26.5, 28.6, 37.8, 55.7, 57.9, 62.0, 106.6, 111.6, 115.4, 121.3, 130.5, 137.5, 152.5, 157.0, 159.0. MS (%): 326 (parent+1, 100).

EXAMPLE 143

6-{4-[1-Cinnamyl-2-(4-isobutyl-piperazin-1-yl)-ethyl]-phenyl}-pyridin-2-ylamine

Prepared as in Example 133 using cinnamyl bromide in the alkylation analogous to Example 133A, in 98% yield for the final deblocking step, converted to the hydrochloride salt in ether.

¹H-NMR (CDCl₃, δ): 0.85 (d, J=7, 6H), 1.73 (m, J=6, 1H), 2.03 (d, J=7, 2H), 2.36 (m, 6H), 2.49 (m, 5H), 2.67 (m, 2H), 2.97 (m, 1H), 4.50 (bs, 2H), 6.08 (m, 1H), 6.30 (m, 1H), 6.39 (d, J=8, 1H), 7.04 (d, J=7, 1H), 7.12 (m, 1H), 7.21 (m, 7H), 7.45 (t, J=8, 1H), 7.82 (m, 2H). ¹³C-NMR (CDCl₃, δ): 21.0, 25.3, 38.1, 43.7, 53.6, 64.1, 66.9, 106.9, 110.8, 126.0, 126.8, 128.1, 128., 128.8, 131.2, 137.7, 138.3, 144.8, 156.1, 158.2. APCI MS (%): 455 (parent+1, 100).

EXAMPLE 144

6-{4-[(Cyclohexyl-methyl-amino)-methyl]-2-fluoro-phenyl}-pyridin-2-ylamine

A. 2-Fluoro-4-methylphenylboronic Acid:

Prepared as in Example 141A, using 2-fluoro-4-methylbromobenzene, in 97% yield, as a low-melting solid.

¹H-NMR (CDCl₃, δ): 2.37 (s, 3H), 6.86 (d, J=8, 1H), 7.00 (d, J=8, 1H), 7.685 (m, 1H).

B. 2-(2,5-Dimethylpyrrolyl)-3-(2-fluoro-4-methylphenyl)-pyridine:

Prepared as in Example 141B, in 73% yield as a low-melting, yellow solid.

¹H-NMR (CDCl₃, δ): 2.20 (s, 6H), 2.37 (s, 3H), 5.91 (s, 2H), 6.97 (d, J=8, 1H), 7.04 (d, J=8, 1H), 7.13 (d, J=7, 1H), 7.84 (m, 2H), 7.98 (t, J=8, 1H). APCI MS (%): 281 (parent+1, 100).

C. 6-(2-Fluoro-4-methylphenyl)-pyridin-2-ylamine:

Prepared as in Example 141C in 68% yield, as an oil.

¹H-NMR (CDCl₃, δ): 2.35 (s, 3H), 6.43 (d, J=8, 1H), 6.92 (d, J=8, 1H), 7.01 (m, 1H), 7.09 (m, 1H), 7.46 (t, J=8, 1H), 7.76 (t, J=8, 1H). APCI MS (%): 203 (parent+1, 100).

D. 2-Phthalimido-6-(2-fluoro-4-methylphenyl)-pyridine:

Prepared as in Example 141D in 73% yield as a low-melting solid.

¹H-NMR (CDCl₃, δ): 2.37 (s, 3H), 6.96 (d, J=8, 1H), 7.04 (m, 1H), 7.35 (dd, J=1,8, 1H), 7.8–8.0 (m, 7H). APCI MS (%): 333 (parent+1, 100).

E. 2-Phthalimido-6-(2-fluoro)-4-bromomethylphenyl)-pyridine:

Prepared as in Example 141E in 62% yield as a crude solid, which was used directly in the following step.

APCI MS (%): 411/413 (parent+1, 45/42), remaining peaks due to impurities.

F. 2-Phthalimido-6-[2-fluoro-4-(N-cyclohexyl-N-methylamino-methyl]phenyl)-pyridine:

Prepared as in Example 141F in 8% yield as an oil.

¹H-NMR (CDCl₃, δ): 1.22 (m, 6H), 1.6–1.8 (m, 4H), 2.22 (s, 3H), 2.45 (m, 1H), 3.62 (s, 2H), 7.19 (d, J=7, 1H), 7.35 (dd, J=1,8, 1H), 7.8–8.0 (m, 8H). APCI MS (%): 444 (parent+1, 100).

G. 6-{4-[(Cyclohexyl-methyl-amino)-methyl]-2-fluoro-phenyl}-pyridin-2-ylamine:

Prepared as in Example 141G in 57% yield as an oil, which was converted to the hydrochloride salt.

¹H-NMR (hydrochloride sail: in CD₃OD, δ): 1.16–1.48 (m, 7H), 1.57–1.77 (m, 3H), 1.89–2.05 (m, 2H), 2.09–2.22 (m, 2H), 2.76 (s, 2H), 7.05 (d, J=8, 1H), 7.16 (s, J=8, 1H), 7.58–7.66 (m, 2H), 7.83 (t, J=8, 1H), 7.99 (t, J=8, 1H). APCI MS(%): 314 (parent+1, 100).

EXAMPLE 145

6-[4-((N-Phenethyl-N-methylamino-methyl)-phenyl]-pyridin-2-ylamine

Prepared as in Example 133D in 57% yield, mp>250° C., as the hydrochloride salt.

¹H-NMR (CDCl₃, δ): 2.30 (s, 3H), 2.67 (m, 2H), 2.83 (m, 2H), 3.60 (s, 2H), 4.51 (bs, 2H), 6.43 (d, J=8, 1H), 7.08 (d, J=7, 1H), 7.19 (m, 3H), 7.25 (m, 2H), 7.35 (m, 2H), 7.48 (t, J=8, 1H), 7.87 (m, 2H). ¹³C-NMR (CD₃OD, δ) 33.8, 42.2, 59.1, 61.85, 107.0, 110.7, 125.9, 126.7, 128.3, 128.7, 129.2, 138.3, 138.4, 139.3, 140.4, 156.0, 158.3. MS (%): 318 (parent+1, 100).

EXAMPLE 146

6-{4-[2-(4-(Isoquinolin-1-yl)-piperazin-1-yl)-ethyl]-phenyl}-pyridin-2-ylamine

Prepared as in Example 1, using N-isoquinolin-1-yl-piperazine, in 30% yield.

¹H-NMR (CDCl₃, δ): 2.63 (m, 2H), 2.75 (bs, 4H), 2.85 (m, 2H), 3.38 (bs, 4H), 5.95 (bs, 2H), 6.39 (d, J=8, 1H), 7.02 (d, J=7, 1H), 7.31 (m, 2H), 7.39 (d, J=4, 1H), 7.45 (t, J=8, 1H), 7.60 (t, J=6, 1H), 7.71 (t, J=6, 1H), 7.89 (m, 3H), 8.09 (m, 2H). MS (%): 410 (parent+1, 100), 216 (38), 145 (45). Anal. (after conversion to the hydrochloride salt) Calc'd. for C₂₆H₂₇N₅·4HCl·2H₂O: C, 52.79, H, 5.92, N, 11.83. Found: C, 53.11, H, 6.06, N, 11.53.

What is claimed is:

1. A compound of the formula

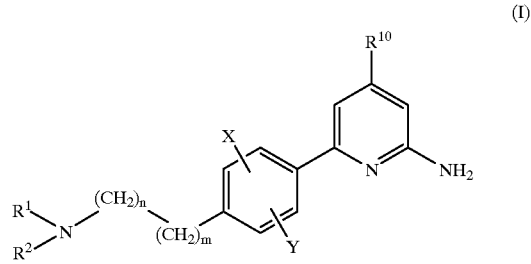

(I)

and the pharmaceutically acceptable salts thereof, wherein $R^1$ and $R^2$ form, together with the nitrogen to which they are attached, an azabicyclic ring containing from 6 to 14 ring members, from 1 to 3 of which are nitrogen and the rest of which are carbon;

n is 0,1 or 2; and each carbon of said $(CH_2)_n$ can optionally be substituted with a substituent $R^8$;

m is 0,1, or 2; and each carbon of said $(CH_2)_m$ can optionally be substituted with a substituent $R^9$;

each $R^8$ and each $R^9$ is selected, independently, from $(C_1-C_4)$alkyl, aryl-$(C_1-C_4)$alkyl wherein said aryl is selected from phenyl and naphthyl; allyl and phenallyl;

X and Y are selected, independently, from methyl, methoxy, hydroxy and hydrogen; and $R^{10}$ is hydrogen or $(C_1-C_6)$ alkyl;

with the proviso that $R^8$ is absent when n is zero and $R^9$ is absent when m is zero;
or a pharmaceutically acceptable salt of such compound.

2. A compound according to claim 1 wherein $NR^1R^2$ is a group of the formula

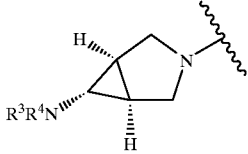

wherein $NR^3R^4$ is $NH_2$.

3. A compound according to claim 1 wherein $NR^1R^2$ is a group of the formula

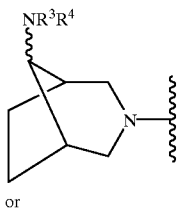

or

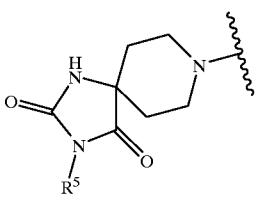

wherein $R^5$ is aralkyl and $R^6$ is (4-fluoro)phenylacetyl.

4. A pharmaceutical composition comprising a compound according to claim 1, and a pharmaceutically acceptable carrier.

5. A method of inhibiting NOS in a mammal, comprising administering to said mammal a NOS inhibiting effective amount of a compound according to claim 1.

6. A method according to claim 4, wherein the mammal is suffering from a condition selected from the group consisting of migraine, inflammatory diseases, stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions, emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer in a mammal, comprising administering to said mammal a NOS inhibiting effective amount of a compound according to claim 1.

7. A compound selected from the following:

6-((2-(6-(t-butoxycarbonylamino)-3-azabicyclo[3.1.0]hex-3-yl)ethyl)phenyl)-pyridin-2-ylamine;

3-{2-[4-(6-Amino-pyridin-2-yl)-phenyl]-ethyl}-3-azabicyclo[3.1.0]hex-6-ylamine;

6-{4-[2-(3,4-Dihydro-1H-isoquinolin-2-yl)-ethyl]-phenyl}-pyridin-2-ylamine;

6-{4-[2-(5-Methyl-2,5-diaza-bicyclo[2.2.1]hept-2-yl)-ethyl]-phenyl}-pyridin-2-ylamine;

6-{4-[2-(8-Aza-spiro[4.5]dec-8-yl)-ethyl]-phenyl}-pyridin-2-ylamine;

6-{4-[2-(1,3-Dihydro-isoindol-2-yl)-ethyl]-phenyl}-pyridin-2-ylamine;

2-{2-[4-(6-Amino-pyridin-2-yl)-phenyl]-ethyl}-1,2,3,4-tetrahydro-isoquinoline-3-carboxylic acid;

1-(3-{2-[4-(6-Amino-pyridin-2-yl)-phenyl]-ethyl}-3-aza-bicyclo[3.1.0]hex-6-yl)-3-phenyl-urea;

(3-{2-[4-(6-Amino-pyridin-2-yl)-phenyl]-ethyl}-3-aza-bicyclo[3.1.0]hex-6-yl)-dimethyl-amine;

N-(3-{2-[4-(6-Amino-pyridin-2-yl)-phenyl]-ethyl}-3-aza-bicyclo[3.1.0]hex-6-yl)-2-(4-fluoro-phenyl)-acetamide;

8-{2-[4-(6-Amino-pyridin-2-yl)-phenyl]-ethyl}-3-benzyl-1,3,8-triaza-spiro[4.5]decane-2,4-dione;

3-{2-[4-(6-Amino-pyridin-2-yl)-phenyl]-ethyl}-3-azabicyclo[3.2.1]oct-8-ylamine;

(3-{2-[4-(6-Amino-pyridin-2-yl)-phenyl]-ethyl}-3-aza-bicyclo[3.1.0]hex-6-yl)-phenethyl-amine;

(3-{2-[4-(6-Amino-pyridin-2-yl)-phenyl]-ethyl}-3-aza-bicyclo[3.1.0]hex-6-yl)-(3-phenyl-propyl)-amine hydrochloride salt;

2-(3-{2-[4-(6-Amino-pyridin-2-yl)-phenyl]-ethyl}-3-aza-bicyclo[3.1.0]hex-6-ylamino)-acetamide;

8-{2-[4-(6-Amino-pyridin-2-yl)-phenyl]-ethyl}-3-phenethyl-1,3,8-triaza-spiro[4.5]decane-2,4-dione;

8-{2-[4-(6-Amino-pyridin-2-yl)-phenyl]-ethyl}-8-aza-bicyclo[3.2.1]oct-3-ylamine;

{2-[4-(6-Amino-pyridin-2-yl)-phenyl]-ethyl}-(8-benzyl-8-aza-bicyclo[3.2.1]oct-3-yl)-amine;

{2-[4-(6-Amino-pyridin-2-yl)-phenyl]-ethyl}-(8-aza-bicyclo[3.2.1]oct-3-yl)-amine;

1-(3-{2-[4-(6-Amino-pyridin-2-yl)-phenyl]-ethylamino}-8-aza-bicyclo[3.2.1]oct-8-yl)-2-(4-fluoro-phenyl)-ethanone;

{2-[4-(6-Amino-pyridin-2-yl)-phenyl]-ethyl}-(8-methyl-8-aza-bicyclo[3.2.1]oct-3-yl)-amine;

{2-[4-(6-Amino-pyridin-2-yl)-phenyl]-ethyl}-(3-benzyl-3-aza-bicyclo[3.1.0]hex-6-yl)-amine;

{2-[4-(6-Amino-pyridin-2-yl)-phenyl]-ethyl}-[8-(4-fluoro-benzyl)-8-aza-bicyclo[3.2.1]oct-3-yl]-amine;

{2-[4-(6-Amino-pyridin-2-yl)-phenyl]-ethyl}-[8-(4-chloro-benzyl)-8-aza-bicyclo[3.2.1]oct-3-yl]-amine;

N-(8-{2-[4-(6-Amino-pyridin-2-yl)-phenyl]-ethyl}-8-aza-bicyclo[3.2.1]oct-3-yl)-benzamide;

{2-[4-(6-Amino-pyridin-2-yl)-phenyl]-ethyl}-(3-benzyl-3-aza-bicyclo[3.3.1]non-9-yl)-amine;

N-(8-{2-[4-(6-Amino-pyridin-2-yl)-phenyl]-ethyl}-8-aza-bicyclo[3.2.1]oct-3-yl)-2-(4-fluoro-phenyl)-acetamide;

N-(3-{2-[4-(6-Amino-pyridin-2-yl)-phenyl]-ethyl}-3-aza-bicyclo[3.3.1]non-9-yl)-benzamide (anti-isomer);

N-(3-{2-[4-(6-Amino-pyridin-2-yl)-phenyl]-ethyl}-3-aza-bicyclo[3.3.1]non-9-yl)-benzamide (syn-isomer);

3-{2-[4-(6-Amino-pyridin-2-yl)-phenyl]-ethyl}-3-aza-bicyclo[3.3.1]non-9-ylamine;

3-{2-[4-(6-Amino-pyridin-2-yl)-phenyl]-ethyl}-3-aza-bicyclo[3.1.0]hexane-6-carboxylic acid ethyl ester;

3-{2-[4-(6-Amino-pyridin-2-yl)-phenyl]-ethyl}-3-aza-bicyclo[3.1.0]hexane-6-carboxylic acid;

3-{2-[4-(6-Amino-pyridin-2-yl)-phenyl]-ethyl}-3-aza-bicyclo[3.1.0]hex-6-ylamine (anti-isomer);

(3-{2-[4-(6-Amino-pyridin-2-yl)-phenyl]-ethyl}-3-aza-bicyclo[3.1.0]hex-6-yl)-(4-methyl-piperazin-1-yl)-methanone;

{2-[4-(6-Amino-pyridin-2-yl)-phenyl]-ethyl}-(9-benzyl-3-oxa-9-benzyl-3-oxa-9-aza-bicyclo[3.3.1]non-7-yl)-amine (more polar diastereomer);

{2-[4-(6-Amino-pyridin-2-yl)-phenyl]-ethyl}-(9-benzyl-3-oxa-9-aza-bicyclo[3.3.1]non-7-yl)-amine (less polar diastereomer);

{2-[4-(6-Amino-pyridin-2-yl)-phenyl]-ethyl}-(3-oxa-9-aza-bicyclo[3.3.1]non-7-yl)-amine;

9-{2-[4-(6-Amino-pyridin-2-yl)-phenyl]-ethyl}-3-oxa-9-aza-bicyclo[3.3.1]non-7-ylamine;

{2-[4-(6-Amino-pyridin-2-yl)-phenyl]-ethyl}-(3-oxa-9-aza-bicyclo[3.3.1]non-7-yl)-amine; and 6-{4-[2-(4-(Isoquinolin-1-yl)-piperazin-1-yl)-ethyl]-phenyl}-pyridin-2-ylamine;

or a pharmaceutically acceptable salt thereof.

8. A compound according to claim 1, wherein $R^1$ and $R^2$, together with the nitrogen to which they are attached, form an azabicyclic ring selected from the following:

-continued wherein $R^3$ and $R^4$ are selected from hydrogen, $(C_1-C_6)$ alkyl, phenyl, naphthyl, $(C_1-C_6)$alkyl-C(=O)—, HC(=O)—, $(C_1-C_6)$alkoxy-(C=O)—, phenyl-C(=O)—, naphthyl-C(=O)—, and $(R^7)_2NC(=O)$— wherein each $R^7$ is selected, independently, from hydrogen and $(C_1-C_6)$alkyl; and $R^5$ is selected from hydrogen, $(C_1-C_6)$alkyl, phenyl, naphthyl, phenyl-$(C_1-C_6)$alkyl- and naphthyl$(C_1-C_6)$alkyl-.

9. A compound according to claim 1, wherein such compound is selected from:

3-{2-[4-(6-Amino-pyridin-2-yl)-phenyl]-ethyl}-3-aza-bicyclo[3.1.0]hex-6-ylamine;

{2-[4-(6-Amino-pyridin-2-yl)-plenyl]-ethyl}-(3-oxa-9-aza-bicyclo[3.3.1]non-7-yl)-amine;

(3-{2-[4-(6-Amino-pyridin-2-yl)-phenyl]-ethyl}-3-aza-bicyclo[3.1.0]hex-6-yl)-dimethyl-amine;

8-{2-[4-(6-Amino-pyridin-2-yl)-phenyl]-ethyl}-3-benzyl-1,3,8-triaza-spiro[4.5]decane-2,4-dione;

8-{2-[4-(6-Amino-pyridin-2-yl)-phenyl]-ethyl}-8-aza-bicyclo[3.2.1]oct-3-ylamine;

3-{2-[4-(6-Amino-pyridin-2-yl)-phenyl]-ethyl}-3-aza-bicyclo[3.2.1]oct-8-ylamine; and 6-{4-[2-(8-Aza-spiro[4.5]dec-8-yl)-ethyl]-phenyl}-pyridin-2-ylamine;

and the pharmaceutically acceptable salts of these compounds.

* * * * *